(12) United States Patent
Whitman et al.

(10) Patent No.: US 9,579,101 B2
(45) Date of Patent: Feb. 28, 2017

(54) SURGICAL STAPLING DEVICE AND METHOD

(71) Applicant: NEW HOPE VENTURES, LP, Newtown, PA (US)

(72) Inventors: Michael P. Whitman, Newtown, PA (US); David Johnston, Robbinsville, NJ (US); Peter Datcuk, Quakertown, PA (US)

(73) Assignee: NEW HOPE VENTURES, LP, Newtown, PA (US)

( * ) Notice: Subject to any disclaimer, the term of this patent is extended or adjusted under 35 U.S.C. 154(b) by 4 days.

(21) Appl. No.: 14/604,501

(22) Filed: Jan. 23, 2015

(65) Prior Publication Data

US 2015/0209040 A1  Jul. 30, 2015

Related U.S. Application Data

(63) Continuation of application No. 14/301,080, filed on Jun. 10, 2014, now abandoned, which is a continuation-in-part of application No. 13/350,718, filed on Jan. 13, 2012, now Pat. No. 8,746,533.

(60) Provisional application No. 61/461,196, filed on Jan. 14, 2011.

(51) Int. Cl.
*A61B 17/068* (2006.01)
*A61B 17/072* (2006.01)
(Continued)

(52) U.S. Cl.
CPC ....... *A61B 17/07207* (2013.01); *A61B 17/068* (2013.01); *A61B 17/115* (2013.01);
(Continued)

(58) Field of Classification Search
CPC ............... A61B 17/068; A61B 17/072; A61B 17/07207; A61B 17/115; A61B 17/1155; A61B 2017/07214
(Continued)

(56) References Cited

U.S. PATENT DOCUMENTS 4,520,817 A * 6/1985 Green ............... A61B 17/07207
206/339
5,632,432 A * 5/1997 Schulze ........... A61B 17/07207
227/176.1
(Continued)

OTHER PUBLICATIONS

PCT International Search Report issued May 10, 2012, in International application No. PCT/US2012/021380 (2 pages).

*Primary Examiner* — Scott A. Smith
(74) *Attorney, Agent, or Firm* — Andrews Kurth Kenyon LLP

(57) ABSTRACT

A surgical device comprises a base unit having a hydraulic controller and at least one control piston, a surgical end effector including at least one actuator piston, and a flexible shaft having at least one tube containing hydraulic fluid in hydraulic communication with the base unit and the surgical end effector. The hydraulic controller includes an electric motor configured to drive the control piston to generate hydraulic force. The hydraulic force is transferable from the base unit to the actuator piston of the surgical end effector through the hydraulic fluid in the at least one tube in the flexible shaft, such that the driving of the control piston by the electric motor under the control of the hydraulic controller transfers the hydraulic force from the control piston of the base unit to the actuator piston of the end effector in proportion to the ratio of the area of the control piston and the area of the actuator piston by metering the hydraulic fluid transferred by the control piston.

10 Claims, 72 Drawing Sheets

(51) Int. Cl.
*A61B 17/115* (2006.01)
*A61B 17/00* (2006.01)
*A61B 17/29* (2006.01)

(52) U.S. Cl.
CPC .... *A61B 17/29* (2013.01); *A61B 2017/00199* (2013.01); *A61B 2017/00473* (2013.01); *A61B 2017/00539* (2013.01); *A61B 2017/07214* (2013.01); *A61B 2017/07257* (2013.01); *A61B 2017/07278* (2013.01); *A61B 2017/07285* (2013.01); *A61B 2017/2943* (2013.01)

(58) Field of Classification Search
USPC .............. 227/19, 175.1, 176.1, 175.2, 180.1; 606/139, 153, 219
See application file for complete search history.

(56) References Cited

U.S. PATENT DOCUMENTS

| | | | | |
|---|---|---|---|---|
| 5,897,562 | A * | 4/1999 | Bolanos | A61B 17/07207 227/176.1 |
| 5,937,951 | A * | 8/1999 | Izuchukwu | A61B 17/0684 173/91 |
| 7,121,446 | B2 * | 10/2006 | Arad | A61B 17/07207 227/175.4 |
| 7,225,964 | B2 * | 6/2007 | Mastri | A61B 17/0684 227/176.1 |
| 7,303,108 | B2 * | 12/2007 | Shelton, IV | A61B 17/0682 227/176.1 |
| 7,380,696 | B2 * | 6/2008 | Shelton, IV | A61B 17/0686 227/175.1 |
| 7,832,408 | B2 * | 11/2010 | Shelton, IV | A61B 17/072 128/898 |
| 8,424,738 | B2 * | 4/2013 | Kasvikis | A61B 17/072 227/176.1 |
| 8,499,993 | B2 * | 8/2013 | Shelton, IV | A61B 17/0644 227/176.1 |
| 8,746,533 | B2 * | 6/2014 | Whitman | A61B 17/07207 227/176.1 |
| 8,991,678 | B2 * | 3/2015 | Wellman | A61B 17/07207 227/175.1 |
| 2007/0068990 | A1 | 3/2007 | Shelton et al. | |
| 2007/0125826 | A1 | 6/2007 | Shelton | |
| 2008/0110958 | A1 | 5/2008 | McKenna et al. | |
| 2008/0287977 | A1 | 11/2008 | Viola | |

* cited by examiner

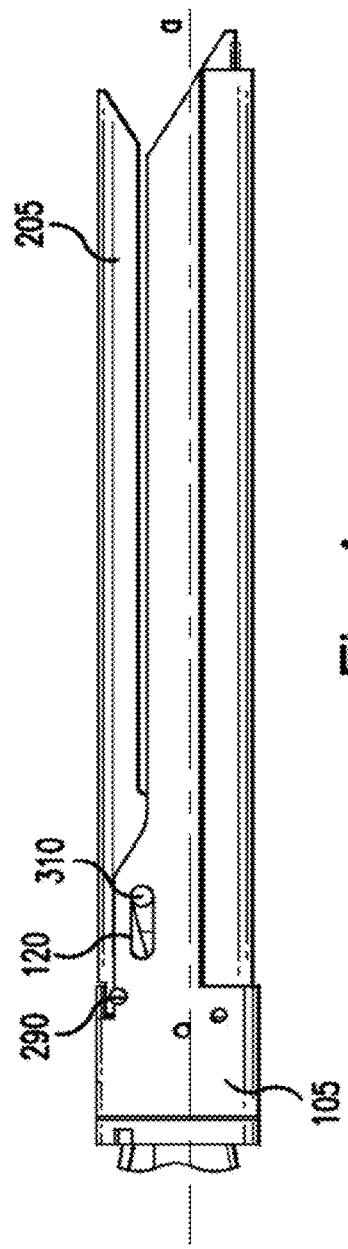
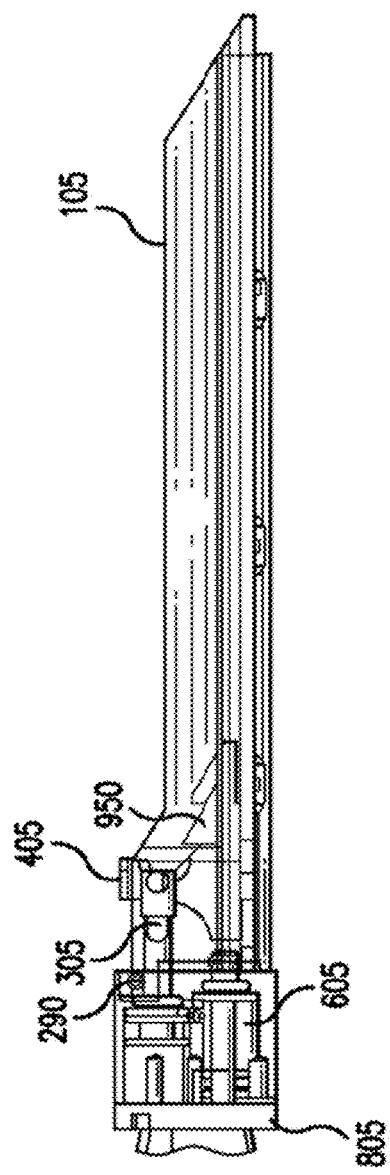

(SECTION A-A)

(SECTION B-B)

(SECTION C-C)

(SECTION D)

(DETAIL E)

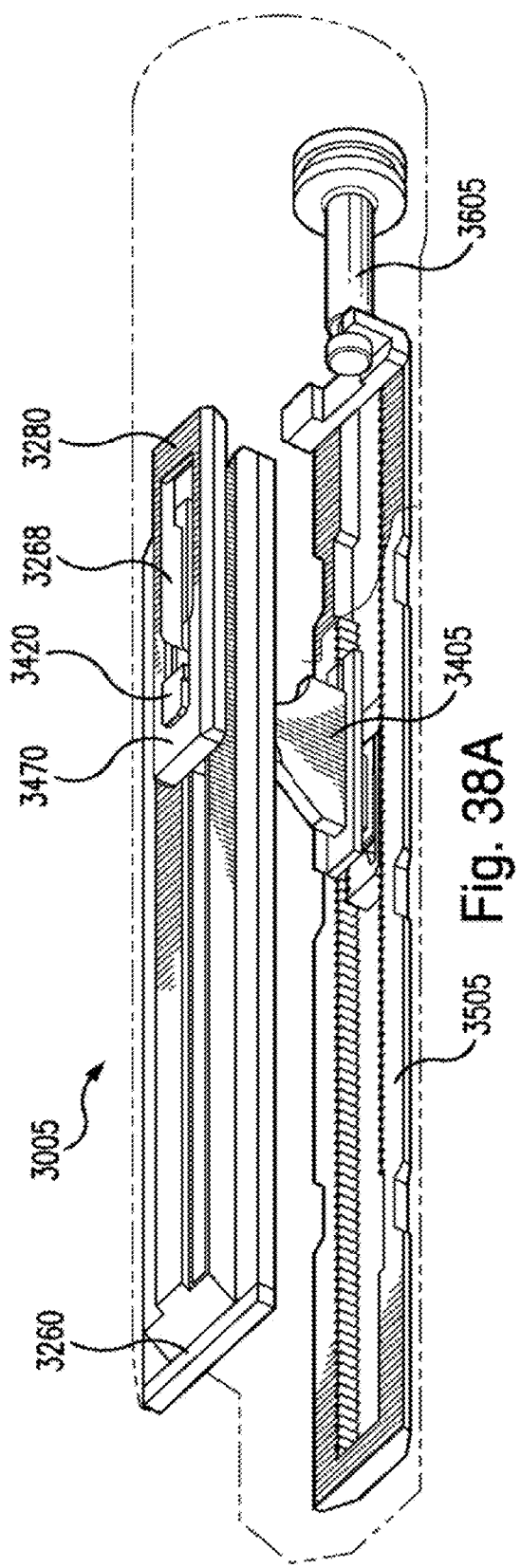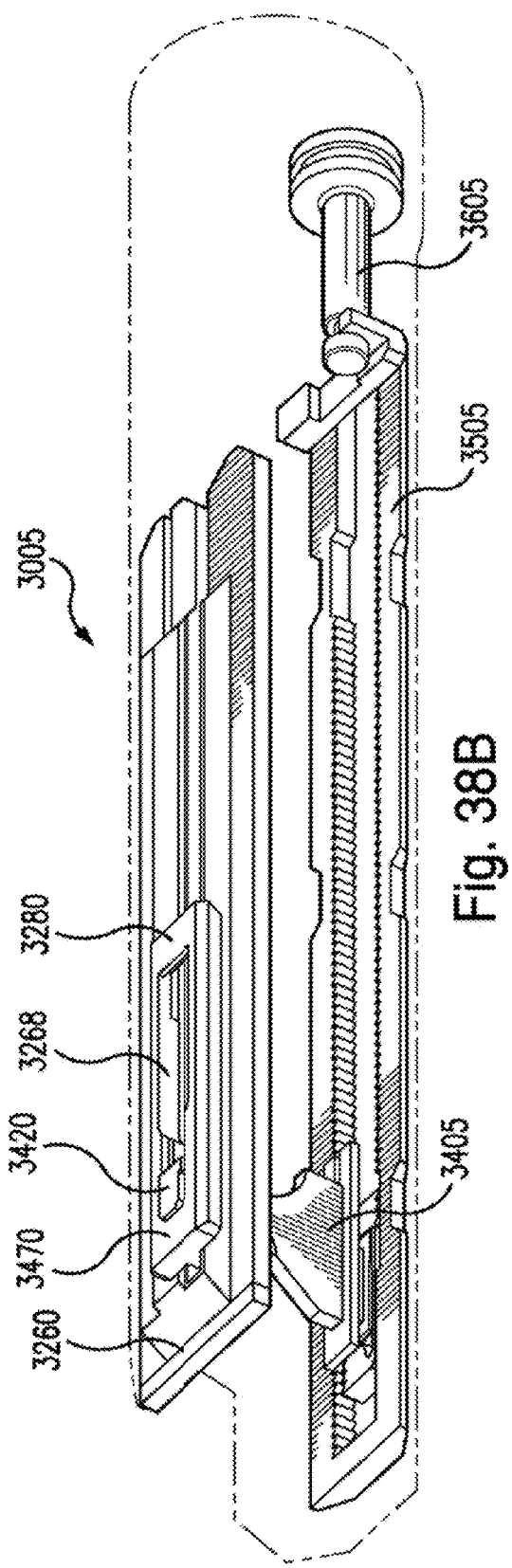

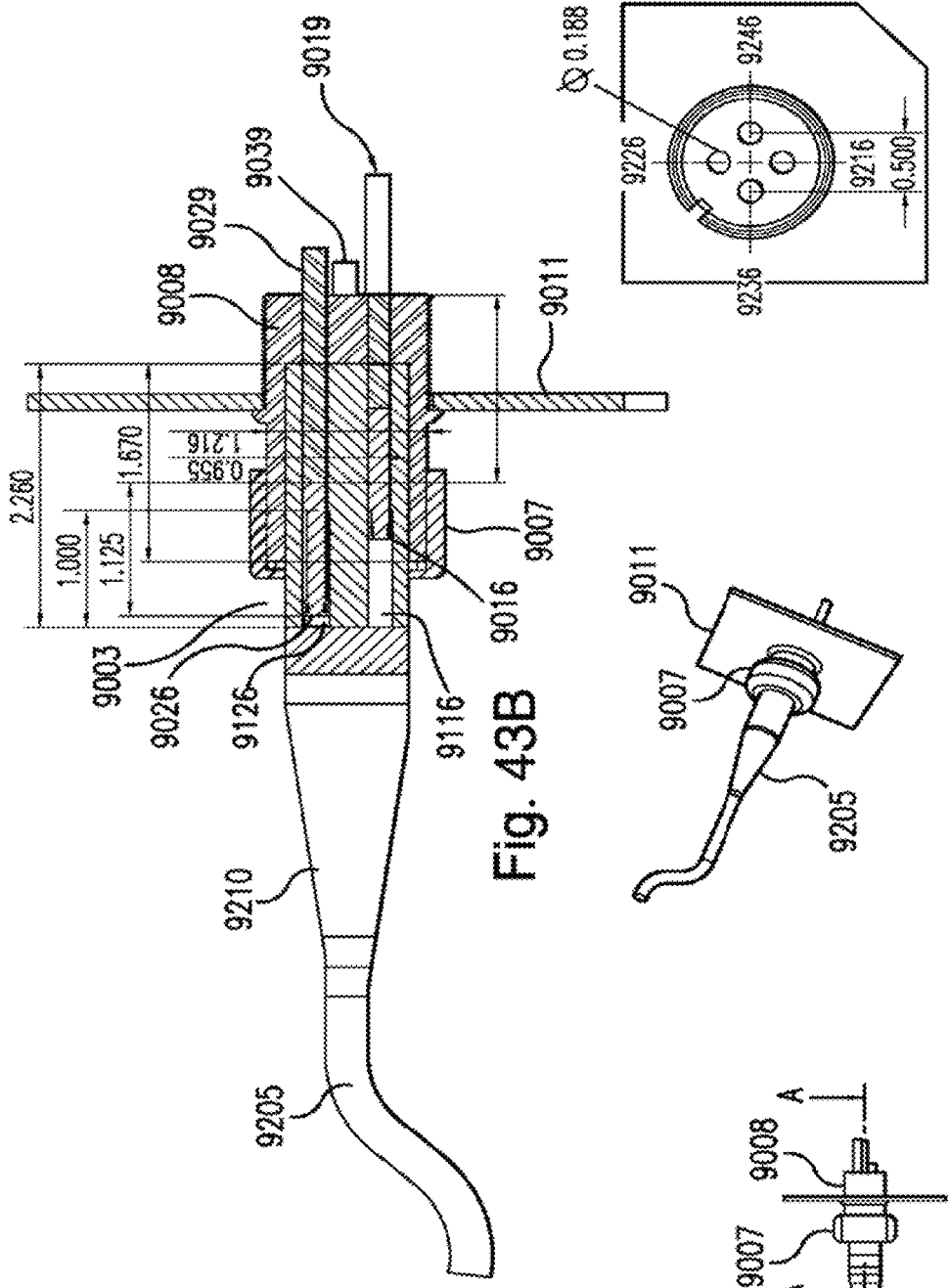

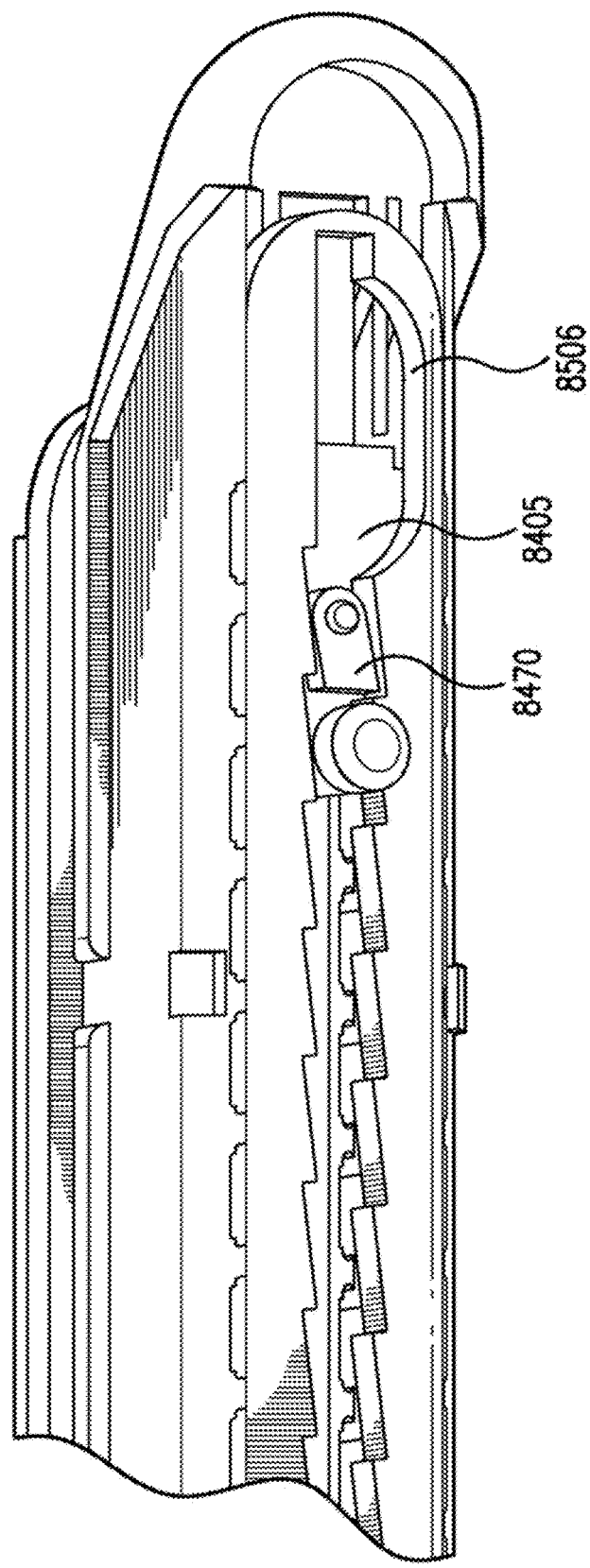

SURGICAL STAPLING DEVICE AND METHOD

CROSS-REFERENCE TO RELATED APPLICATIONS

This application is a continuation of U.S. patent application Ser. No. 14/301,080, filed on Jun. 10, 2014, now abandoned which is a continuation-in-part of U.S. patent application Ser. No. 13/350,718, filed on Jan. 13, 2012, now U.S. Pat. No. 8,746,533 and claims the benefit of U.S. Provisional Patent Application Ser. No. 61/461,196, filed on Jan. 14, 2011, each of which is expressly incorporated herein in its entirety by reference thereto.

FIELD OF THE INVENTION

The present invention relates to a surgical stapling device and method.

BACKGROUND

Some surgical procedures require the tissue to be transected and closed. This is often the case in gastrointestinal tract surgery when a tumor or injury to the tract occurs. Typically transections are made both proximally and distally on opposite sides of the tumor or injured section. For example, a cancerous tumor located on a patient's colon may be removed by transecting the colon on the proximal side of the tumor and then a second transectoin on the distal side of the tumor. Thus, the anomalous tissue section may be removed while leaving two remnant limbs of the colon, which are subsequently anastomosed or rejoined. Since exposing the surrounding tissues to the interior contents of the colon or other organ may greatly increase the risk of infection and associated complications, it is desirable for the remnant limbs to remain closed until the limbs are anastomosed or rejoined.

A linear cutter is a surgical device that clamps tissue, typically between two opposed jaws, and staples and cuts the clamped tissue. Some arrangements include a stapling mechanism, which drives rows of staples into the tissue, typically before or simultaneous to the cutting. These rows of staples serve to transect and close the open ends of the cut organ, thereby limiting any exposure of surrounding tissue to the contents of the organ. Advantageously one or more rows of staples are driven on each side of each cut.

In the stapling procedures described above, staples are typically driven with a staple pusher disposed in one of the clamping jaws. The staple pusher forms the staples by pressing the staples from the first clamping jaw, into and through the clamped tissue, and into an anvil in the opposed clamping jaw configured to bend or otherwise form the staple closure. In order to effectively staple the tissue, it is advantageous to clamp the tissue such that a small thickness, e.g., one millimeter, is disposed between the two clamping jaws. To achieve this result, the clamping jaws must exert and maintain a substantial amount of clamping force. A difficulty may then arise when the staples are driven into the clamped tissue, since the driving of the staples from one of the jaws into an anvil in the other of the jaws applies a force between the jaws that is opposite the clamping force. Thus, during the stapling, even greater clamping force is required to be exerted by the clamping jaws. That is, the clamping jaws must apply sufficient force to both maintain the desired tissue gap between the jaws and to form the staples into their fastened configuration. High clamping forces can be problematic in that the proximally supported jaws may deflect or splay outwardly, thereby making it difficult to achieve a uniform tissue gap along the length of the jaws.

U.S. Pat. No. 4,520,817 discloses a mechanism to potentially alleviate the aforementioned problems by providing a block carrying the staple pusher and cutter with a plurality of lateral projections that ride in slots in the opposed jaws as the cutter and pusher are moved distally. These projection/slot engagements may assist with maintaining a clamping force by providing local support between the jaws in the region of the staple pusher. However, a substantial amount of distally directed force must be applied to the stapler pusher in order to simultaneously cut the tissue, press and form the staples, and overcome the additional resistance due to the projection/slot arrangement. Since the device of U.S. Pat. No. 4,520,817 is a handheld unit requiring full access to the surgical site, the operator is able to manually apply the substantial force, by pushing a knob, at a location that is very close to the jaws.

Some of the aforementioned procedures may be performed endoscopically, which is generally less invasive and allows for more rapid healing as compared to open surgery, which may require large incisions to allow for the access required to utilize manual surgical instruments. Endoscopic procedures typically entail insertion of instruments through a small incision point, e.g., through a cannula. The surgical tools required to perform these procedures generally have elongated shafts that extend from a handpiece or other base unit to an end effector.

The end effectors of endoscopic surgical instruments are commonly referred to as the "business end" of the instrument. They contain components such as fasteners, which are often in the form of surgical staples. These end effectors may transect, form anastomoses in, and occlude viscera and vessels in the human body.

Since the end effector and shaft have relatively small diameters, the end effector and shaft may be inserted through the cannula to perform the procedure while the operator controls the instrument from outside the surgical site. A drawback of such devices is that they generally require the transfer of mechanical force generated manually by the operator from the handpiece or base to the end effector. This is accomplished by drive shafts, pushrods, cables, and the like extending through the shaft. The transfer of power through these mechanisms results in substantial power losses and makes precise control extremely difficult. Further, these drawbacks may be amplified in systems that utilize flexible shafts.

Due to the mechanical inefficiencies of these endoscopic instruments, the projection/slot arrangement of U.S. Pat. No. 4,520,817, which requires a substantial amount of distally applied manual force to drive the staple pusher and cutter, is not well suited for endoscopic end effectors. U.S. Pat. No. 4,520,817 discloses a handheld unit requiring full access to the surgical site, whereby the operator is able to apply the substantial force, by pushing a knob, at a location that is very close to the jaws. This is not feasible for endoscopic or natural orifice procedures which are inherently superior procedures to open and/or endoscopic procedures due to minimized patient trauma and operating room time.

Thus, there is a need for devices and methods that provide an improved power transmission to the end effector. Further there is a need for devices and methods that provide improved clamping in an end effector.

Further, for surgical instruments where an end effector is attached to a flexible shaft, there is known a difficulty in effectively transferring force to the end effector via the flexible shaft. In this regard, an effective flexible stapler would allow surgeons to utilize natural orifices or an umbilical approach to surgery. An effective flexible shafted stapler would allow advances in surgery through a single port approach which would lead to a reduction in pain, elimination of incisions, and reduced operating room time for the patient.

Further, many surgical staplers utilize actuation mechanisms that utilize a drive band which is most often manually operated. These manually operated devices require an operator to manually pull a lever to either provide a one-to-one stroke or to manually repeatedly pull a trigger to achieve a desired actuation. Such devices rely on the force applied by the operator (e.g., a force between the operator's fingers and thumb) for actuation. In this regard, there is a need for a device that does not require a drive band and is powered by means other than manual manipulation.

SUMMARY

Example embodiments of the present invention utilize a reciprocating drive mechanism that allows force transfer from a control assembly to an end effector while eliminating the need for a drive band altogether.

Example embodiments of the present invention improve upon one-to-one input/output relationships of known drive mechanisms. Instead of providing a one-to-one stroke, or a mechanism that requires manually pulling a trigger multiple times to achieve the same effect as a single full stroke, example embodiments of the present invention provide an oscillating drive mechanism. The oscillating mechanism may function at high speed and receives input and output from a piston within a cylinder which moves back and forth rapidly. Since this input/output force is achieved hydraulically, there is no manual input required and the forces generated are greater than manual devices. Since the distance spanned by this back-and-forth is contained with a given distance, movement may be less than, and in some cases, substantially less than, a relative distance that must be traversed in order to actuate the end effector of a given surgical device, especially manually operated devices.

Hydraulic systems may be advantageous over mechanical systems. In a hydraulic system, force from a remote hydraulic control device maybe transferred through a flexible tube, hose, or shaft, which may be of particular importance in endoscopic surgical procedures. Force generated in a remote device or system may be transferred to a distal end effector, used to apply the hydraulic force in surgical applications. Hydraulic forces transferred along a flexible shaft may minimize displacement of the shaft, as compared to mechanical systems. Mechanical systems using cables, gears, or other mechanical elements to transfer force may experience power losses as the mechanical elements experience the transferred force. For example, cables may be wound up, affecting cable length and therefore affecting accurate transfer of force. Gears may lose power during gear reduction. Mechanical systems may therefore require sensor systems to monitor such power losses and changes in the mechanical elements. Hydraulic systems that do not experience these losses do not require the same monitoring devices. Example embodiments of the present invention may have one or more reciprocating pistons, which may carry out one or more discrete steps of activating the surgical instrument. In this regard, a reciprocating piston may move back and forth rapidly in a distance less than 100% of the intended travel of either a clamping feature or firing mechanism in any given example surgical device.

According to example embodiments of the present invention, a surgical device comprises a first jaw, a second jaw having an open position and a closed position with respect to the first jaw, a carriage, a driver, and an actuator configured to reciprocate the driver, e.g., at a high rate with respect to the first and second jaws to translate the carriage with respect to the first and second jaws.

The driver may be hydraulically actuated. Further, the hydraulic actuation may include the hydraulic transfer of force from a control module to an end effector. The hydraulic transfer of force may be provided by a hydraulic fluid disposed in a flexible shaft.

The driver may include an actuation bar.

The actuating bar may include a first plurality of ratchet teeth selectably engagable with the carriage in order to translate the carriage in a first direction.

The actuating bar may include a second plurality of ratchet teeth selectably engagable with the carriage in order to translate the carriage in a second direction.

The first direction may be a distal direction with respect to the first and second jaws and the second direction may be a proximal direction with respect to the first and second jaws.

The carriage may include a first plurality of carriage teeth configured to ratchet with the first set of ratchet teeth when the actuating bar is engaged with the carriage in order to translate the carriage in the first direction.

The carriage may include a second plurality of carriage teeth configured to ratchet with the second set of ratchet teeth when the actuating bar is engaged with the carriage in order to translate the carriage in the second direction.

The carriage may include a spring-loaded bidirectional latching mechanism, e.g., a pawl, configured to ratchet with the first set of ratchet teeth when the actuating bar is engaged with the carriage in order to translate the carriage in the first direction, and to ratchet with the second set of ratchet teeth when the actuating bar is engaged with the carriage in order to translate the carriage in the second direction. This arrangement has the benefit of providing full tooth purchase between the pawl and the first and second sets of ratchet teeth, and preventing side-loading of the carriage. Further, switching the motion of the carriage from the distal direction to the proximal direction requires no user action, and minimal mechanical action, as the spring-loading causes the bidirectional latching mechanism to switch its engagement from the first set of ratchet teeth to the second set of ratchet teeth. The spring load on the bidirectional latching mechanism may be the same, or substantially the same, before and after the bidirectional latching mechanism switches its engagement from the first set of ratchet teeth to the second set of ratchet teeth.

Example embodiments of the present invention eliminate the need for strokes required in the context of other devices. This may be achieved, e.g., by providing an actuation mechanism that oscillates in a confined physical range. This oscillation may be driven by the corresponding oscillation of a control element disposed, e.g., in a control module.

Further, the oscillation of the control element may transfer oscillating forces to a corresponding driver in an end effector of the device via hydraulic fluid. The hydraulic fluid may extend from the control module to the end effector via flexible shaft.

The oscillating control element and/or the oscillating driver may be as one or more reciprocating pistons, e.g., hydraulic pistons.

In accordance with example methods of the present invention, a tissue is clamped between opposed jaws and a carriage is advanced with respect to the opposed jaws via an oscillating actuator in order to cut and/or staple the clamped tissue.

The carriage may comprise a force transfer bar.

The carriage may be configured to exert a clamping force between the first and second jaws as the carriage is advanced to cut and/or staple the tissue. The clamping force exerted by the carriage may be the only clamping force applied between the opposed jaws. Thus, there may be no need for additional pistons, e.g., to close the jaws, therefore eliminating excess materials, reducing costs of manufacture, reducing the risks of malfunction, and simplifying operation.

The oscillating actuation may be performed in response to an operator input signal. For example, the oscillation may occur in response to the operation of a switch or other input. For instance, the input may be a digital, wireless digital, and/or wired digital input mechanism. Further, the device may be configured to continuously oscillate the actuator when the switch is in a first position. Moreover, the device may be configured to cease oscillation of the actuator in response to the switch being in a second position. Further, the oscillating actuation may be controlled via one or more digital, wireless digital, and/or wired digital control signals or any other suitable control system.

According to example embodiments of the present invention, a surgical stapling device comprises a first jaw, a second jaw having an open position and a closed position with respect to the first jaw, an actuating bar arranged in the first jaw and including a first set of ratchet teeth, a ratchet piston configured to oscillatingly displace the actuating bar along a longitudinal direction of the first jaw, a housing, having at least one staple and at least one staple driving slot, situated in the first jaw, and a carriage, including at least one staple-driving wedge, selectively engageable with the first set of ratchet teeth of the actuating bar to translate the carriage in a distal direction through the housing from a proximal terminal position to a distal terminal position, a distance between the distal terminal position and the proximal terminal position greater than a stroke length of the oscillating displacement of the ratchet bar, wherein the staple driving wedge is adapted to drive the staple through the staple driving slot against the second jaw during distal movement of the carriage through the housing.

The actuating bar may further include a second set of ratchet teeth, and the carriage may further be selectively engageable with the second set of ratchet teeth to translate the carriage in a proximal direction through the housing from the distal terminal position to the proximal terminal position.

The ratchet piston may be hydraulically actuated.

The surgical stapling device may further comprise a bidirectional latching mechanism adapted to engage with the first set of ratchet teeth to translate the carriage in the distal direction and to engage with the second sent of ratchet teeth to translate the carriage in the proximal direction.

The bidirectional latching mechanism may be engaged with the carriage via a spring force transfer pin, and may be spring-loaded about the spring force transfer pin.

The actuating bar may include an enlarged opening at a distal end, the enlarged opening sized to allow the spring-loaded bidirectional latching mechanism to rotate about the spring force transfer pin to disengage with the first set of ratchet teeth and engage with the second set of ratchet teeth.

The ratchet piston man include a ratchet piston shaft having a circumferential recess situated at a distal end of the ratchet piston shaft, the actuating bar having a force transfer rib situated at a proximal end of the actuating bar, the force transfer rib configured to fit into the circumferential recess, the ratchet piston shaft configured to transfer force to the ratchet via the circumferential recess and the force transfer rib, to oscillate the actuating bar.

The ratchet piston may be a double-action piston. The surgical stapling device may further comprise a base unit including at least two single-action pistons, wherein one of the at least two single-action pistons is in fluid communication with a distal side of the ratchet piston, and one of the at least two single-action pistons is in fluid communication with a proximal side of the ratchet piston, and wherein each of the at least two single-action pistons exacts positive or negative hydraulic pressure on the distal or the proximal side of the ratchet piston.

The second jaw may be moveable from the open position to the closed position by a clamping force exerted on the second jaw by the carriage.

The carriage may include a first set of carriage teeth and a second set of carriage teeth, the carriage engageable with the actuating bar via one of (i) the first set of carriage teeth being engaged with the first set of ratchet teeth to translate the carriage in the distal direction through the housing and (ii) the second set of carriage teeth being engaged with the second set of ratchet teeth to translate the carriage in the proximal direction through the housing.

The ratchet piston may include a ratchet piston shaft and a force transfer pin situated at a distal end of the ratchet piston shaft, the actuating bar having a force transfer slot situated at a proximal end of the actuating bar, the force transfer pin adapted to fit into the force transfer slot, the ratchet piston shaft adapted to transfer force to the actuating bar via the force transfer pin and the force transfer slot, to oscillate the actuating bar.

The surgical stapling device may further comprise an anvil pivot piston situated in a first anvil pin slot of the first jaw and a second anvil pin slot of the second jaw, and an anvil piston configured to drive the anvil pivot pin in the distal direction to exert a clamping force in the second jaw to move the second jaw from the open position to the closed position, and to drive the anvil pivot pin in the proximal direction to release the clamping for in the second jaw to move the second jaw from the closed position to the open position.

The surgical stapling device may further comprise a piston housing to house the ratchet piston, and a head release latch adapted to releasably engage the piston housing with the first jaw, wherein the ratchet piston is engaged with the actuating bar when the piston housing is engaged with the first jaw.

The surgical stapling device may further comprise a base unit having a hydraulic pump, a flexible shaft in hydraulic communication with the base unit and the ratchet piston, wherein a hydraulic force generated by the hydraulic pump is transferrable from the base unit to the ratchet piston. The base unit may include at least two single-action pistons; one of the at least two single-action pistons being in fluid communication with a distal side of the ratchet piston, and one of the at least two single-action pistons being in fluid communication with a proximal side of the ratchet piston, and each of the at least two single-action pistons may exact positive or negative hydraulic pressure on the distal or the proximal side of the ratchet piston. The surgical stapling device may further comprise a control device, including a switch, situated between the base unit and the ratchet piston, and the switch may be operable to selectively initiate transfer of hydraulic force from the base unit to the ratchet piston, and to selectively terminate transfer of hydraulic force from the base unit to the ratchet piston.

According to example embodiments of the present invention, a method for surgically stapling comprises clamping a second jaw into a closed position with respect to a first jaw from an open position with respect to the first jaw, oscillatingly driving a ratchet piston, oscillating an actuating bar situated in the first jaw by the driving of the ratchet piston, the actuating bar oscillating a stroke length along a longitudinal direction of the first jaw, the actuating bar having a first set of ratchet teeth, ratcheting a carriage in a distal direction from a proximal terminal position to a distal terminal position through a housing situated in the first jaw by the oscillating of the actuating bar, the housing having at least one staple and at least one staple driving slot, by ratcheting engagement with the first set of teeth, and driving the at least one staple through the at least one staple driving slot by the ratcheting of the carriage in the distal direction, wherein a distance between the distal terminal position and the proximal terminal position is greater than the stroke length.

According to example embodiments of the present invention, a surgical device comprises a base unit having a hydraulic controller and at least one control piston, a surgical end effector including at least one actuator piston, and a flexible shaft having at least one tube containing hydraulic fluid in hydraulic communication with the base unit and the surgical end effector, wherein the hydraulic controller includes an electric motor configured to drive the control piston to generate a hydraulic force, and wherein the hydraulic force is transferable from the base unit to the actuator piston of the surgical end effector through the hydraulic fluid in the at least one tube in the flexible shaft, such that the driving of the control piston by the electric motor under the control of the hydraulic controller transfers the hydraulic force from the control piston of the base unit to the actuator piston of the end effector in proportion to the ratio of the area of the control piston and the area of the actuator piston by metering the hydraulic fluid transferred by the control piston.

A first side of the control piston may be in fluid communication with a distal side of the actuator piston, and a second side of the control piston may be in fluid communication with a proximal side of the actuator piston. The control piston may exact positive or negative hydraulic pressure on the distal or the proximal side of the actuator piston.

The hydraulic controller may include a shaft coupled to the electric motor and the control piston, and the shaft may be configured to be linearly moved by electric motor, and to translate the motion to the control piston.

The surgical device may further comprise a control device, including a switch, situated between the base unit and the surgical end effector. The switch may be operable to selectively initiate transfer of the hydraulic force from the base unit to the actuator piston, and to selectively terminate transfer of the hydraulic force from the base unit to the actuator piston.

The hydraulic controller may include at least two control pistons, one of the at least two control pistons may be in fluid communication with a distal side of the actuator piston, and one of the at least two control pistons may be in fluid communication with a proximal side of the actuator piston. Each of the at least two control pistons may exact positive or negative hydraulic pressure on the distal or the proximal side of the actuator piston.

The hydraulic controller may further include a shaft coupled to the electric motor and one of the at least two control pistons, the shaft configured to be linearly moved by electric motor, and to translate the motion to move the control piston.

The surgical end effector may comprise a first jaw, a second jaw having an open position and a closed position with respect to the first jaw, an actuating bar arranged in the first jaw and including a first set of ratchet teeth, a housing; having at least one staple and at least one staple driving slot, situated in the first jaw, and a carriage including a force transfer bar, a sled base, and a release pin, the force transfer bar having a protrusion for engagement with a locking tang of the sled base, the release pin configured to hold the protrusion of the force transfer bar in approximation with the locking tang of the sled base. One of the at least one actuating piston may be configured to oscillatingly displace the actuating bar along a longitudinal direction of the first jaw. The carriage may be selectively engageable with the first set of ratchet teeth of the actuating bar to translate the carriage in a distal direction through the housing from a proximal terminal position to a distal terminal position, and may be engageable with the first and second jaw to exert a clamping force to move the second jaw from the open position to the closed position. The release pin may be configured, upon removal, to permit the force transfer bar to release from the locking tang of the sled base.

According to exemplary embodiments of the present invention, a surgical stapling device, comprises a first jaw, a second jaw having an open position and a closed position with respect to the first jaw, an actuating bar arranged in the first jaw and including a first set of ratchet teeth, a ratchet piston configured to oscillatingly displace the actuating bar along a longitudinal direction of the first jaw, a housing, having at least one staple and at least one staple driving slot, situated in the first jaw, and a carriage including a force transfer bar, a sled base, and a release pin, the force transfer bar having a protrusion for engagement with a locking tang of the sled base, the release pin configured to hold the protrusion of the force transfer bar in approximation with the locking tang of the sled base. The carriage may be selectively engageable with the first set of ratchet teeth of the actuating bar to translate the carriage in a distal direction through the housing from a proximal terminal position to a distal terminal position, and may be engageable with the first and second jaw to exert a clamping force to move the second jaw from the open position to the closed position. The release pin may be configured, upon removal, to permit the force transfer bar to release from the locking tang of the sled base.

The surgical stapling device may further comprise a base unit having a hydraulic controller and at least one control piston, and a flexible shaft having at least one tube containing hydraulic fluid in hydraulic communication with the base unit and the ratchet piston. The hydraulic controller may include an electric motor configured drive the control piston to generate a hydraulic force. The hydraulic force may be transferable from the base unit to the ratchet piston through the hydraulic fluid in the at least one tube in the flexible shaft, such that the driving of the control piston by the electric motor under the control of the hydraulic controller transfers the hydraulic force from the control piston of the base unit to the ratchet piston of the end effector in proportion to the ratio of the area of the control piston and the area of the ratchet piston by metering the hydraulic fluid transferred by the control piston.

The carriage may include at least one staple-driving wedge adapted to drive the staple through the staple driving slot against the second jaw during distal movement of the carriage through the housing.

Further features and aspects of example embodiments of the present invention are described in more detail below with reference to the appended Figures.

BRIEF DESCRIPTION OF THE DRAWINGS

FIG. 4 is a side view of the device of FIG. 1 with the jaws in a closed position.

FIG. 5 is a side view of a housing or body assembly of the device of FIG. 1.

FIG. 38A shows a perspective view of a carriage actuation and guidance assembly of the device of FIG. 32A with the carriage and the anvil sled assembly in a proximal region of the jaws.

FIG. 38B shows a carriage actuation and guidance assembly of the device of FIG. 32A with the carriage and the anvil sled assembly advanced to a distal region of the jaws.

FIGS. 43A, 43B, 43C, 43D, and 43E show hydraulic control hardware.

FIGS. 47A to 47C show a partial bottom view of the device of FIG. 45.

DETAILED DESCRIPTION

Figure 1:
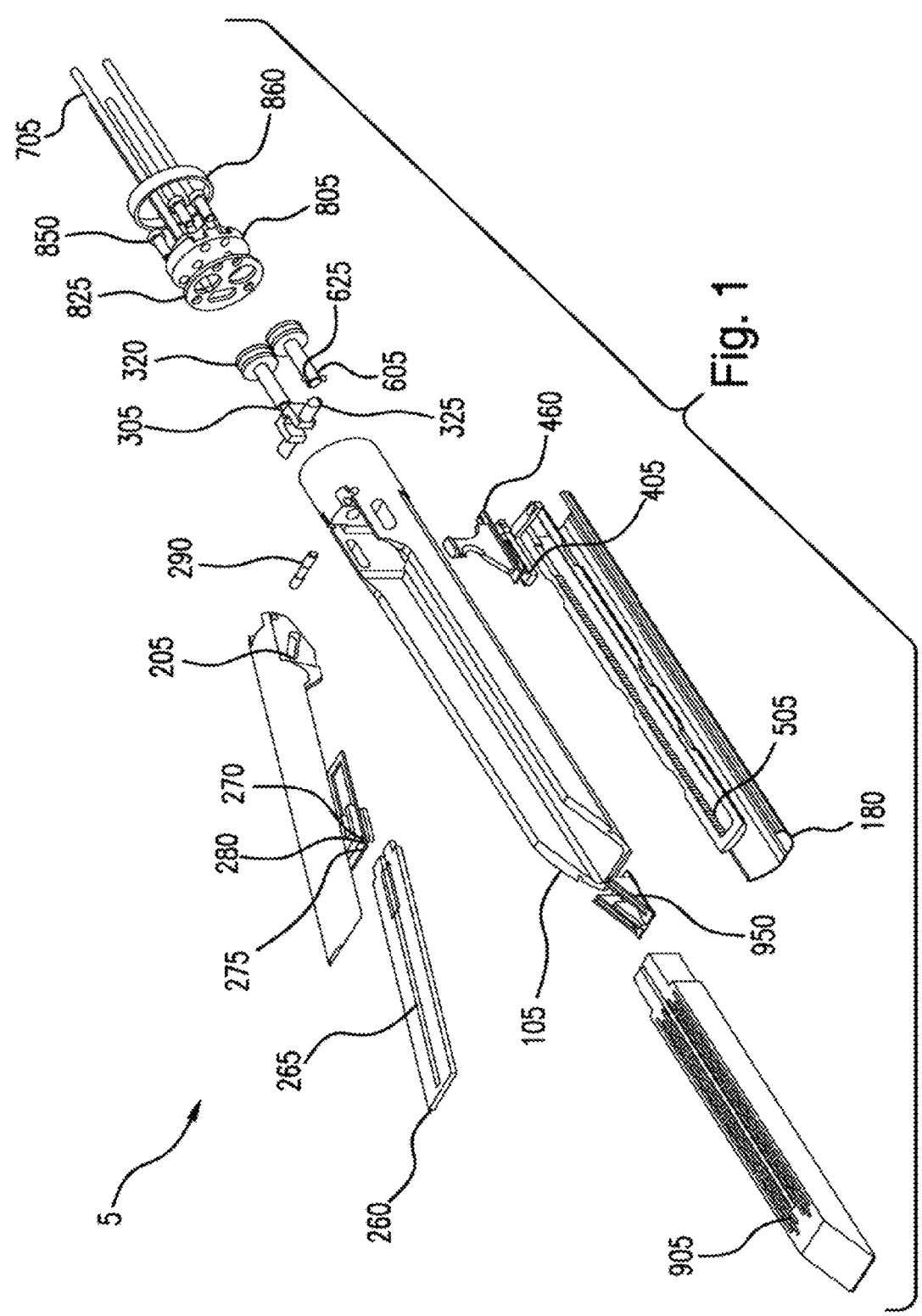
FIG. 1 is an exploded perspective view of a surgical device according to an example embodiment of the present invention.

FIGS. 1 to 13E illustrate a surgical device 5 that is an exploded view of a surgical device 5 in accordance with an example embodiment of the present invention. In accordance with example methods of the present invention, the device 5 cuts and staples a clamped tissue utilizing an oscillating actuator 505, in the exemplary form of a hydraulically driven actuation bar 505, to advance a carriage 405 along at least one of a first jaw and a second jaw. In the exemplary device 5, the first jaw includes the housing 105 and the second jaw includes the anvil 205. In the illustrated example, the carriage 405 is configured to engage both the first jaw 105 and the second jaw 205 in order to exert a localized clamping force at the axial location of the carriage 405 as it is advanced along the first and second jaws 105, 205. The exemplary carriage 405 drives staples into the clamped tissue and cuts the clamped tissue as it is advanced along the jaws by the oscillating actuator 505. The axial location of the clamping force exerted by the carriage 405 is substantially aligned with the axial location of the concurrently-driven staple, to effect a robust staple driving action. The carriage 405 may be moved in a reversed direction with respect to the jaws by further oscillation of the actuation element 505 after changing a state of the oscillating actuation element 505. In the exemplary device 5, the state of the actuation bar 505 is changed by laterally shifting the actuation bar with respect to the carriage 405.

Referring to the exploded view of FIG. 1, the surgical device 5 includes the housing 105, a cover 180, the anvil 205, a staple form plate 260, an anvil pivot pin 290, an anvil piston 305, carriage 405, actuation/ratchet bar 505, a ratchet actuation piston 605, tubes 705, rear cap 805, a cylindrical gasket 825, screws 850, crimp ring 860, reload housing 905 and reload sled 950.

Figure 2:
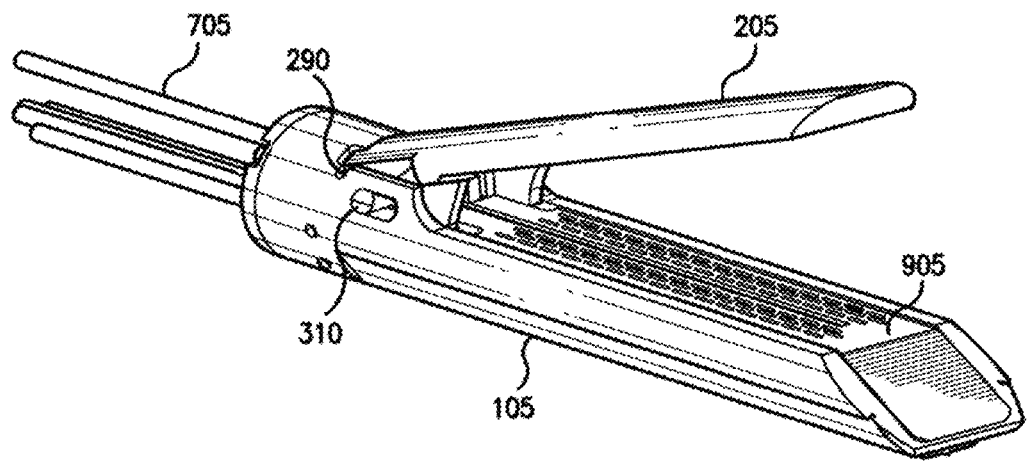
FIG. 2 shows the device of FIG. 1 in an assembled state.
Figure 3:
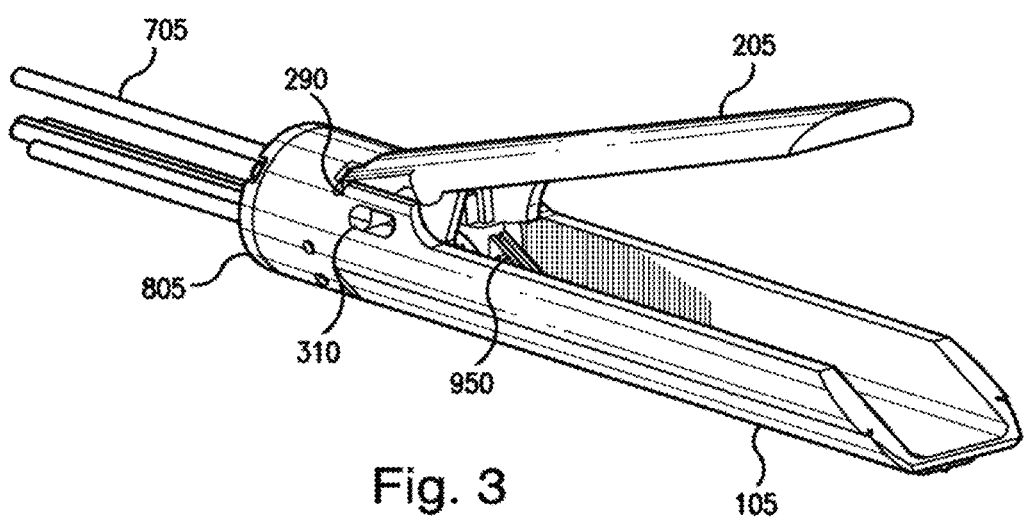
FIG. 3 shows the device of FIG. 1 without a staple cartridge.
Figure 6:
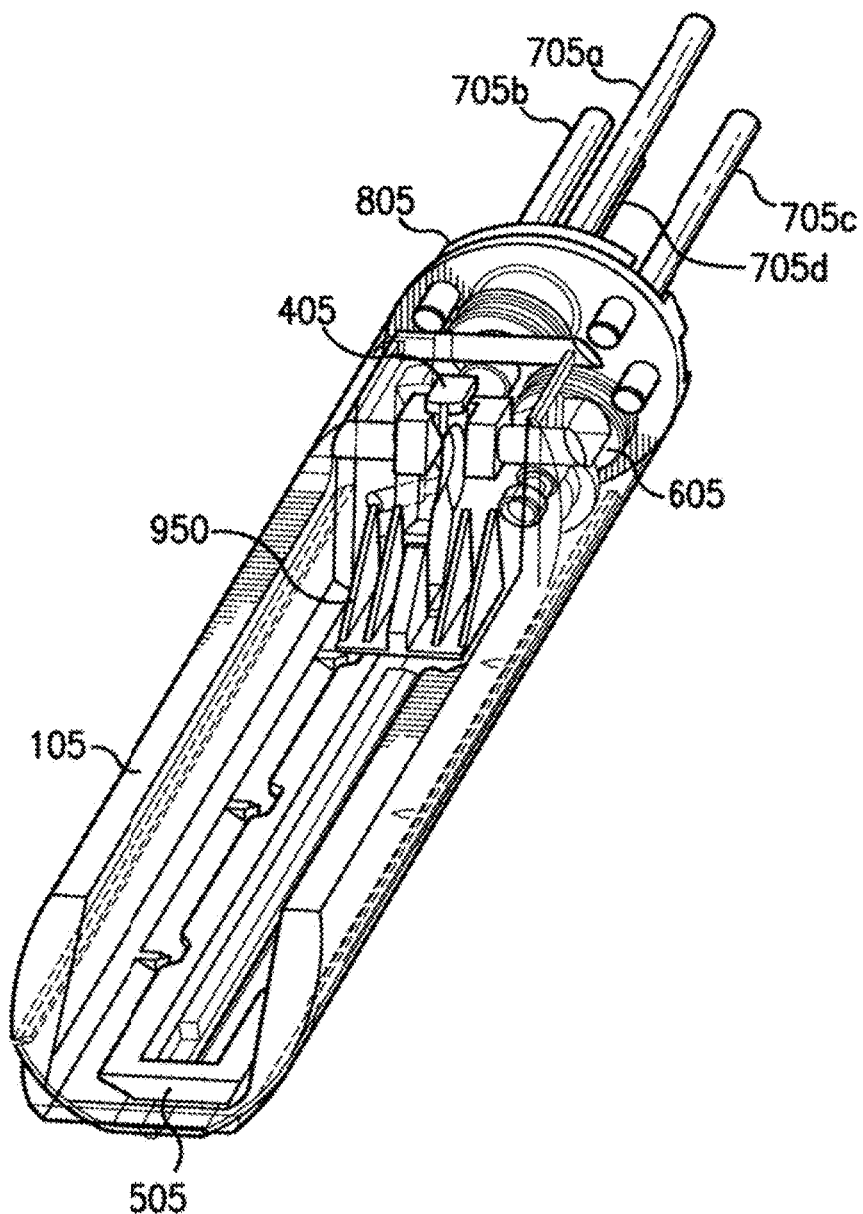
FIG. 6 shows the body assembly of the device of FIG. 1.

Referring to assembled device 5 as illustrated in FIG. 2, the anvil 205 is in an open orientation with respect to the housing 105 and the reload housing 905. The reload housing 905 may itself constitute a replaceable staple cartridge, or the reload housing 905 and the reload sled 950 may in combination form a replaceable staple cartridge. In other words, the reload sled 950 may remain with the housing 105 when the reload housing 905 is removed (as illustrated in FIG. 3), or the reload sled 950 may be mounted to the reload housing 905 such that the reload sled 950 is removed along with the reload housing 905. In accordance with the latter configuration, each reload housing 905 may have its own reload sled 950, or the reload sled 905 may be interchangeable between different reload housings 905.

Figure 9A:
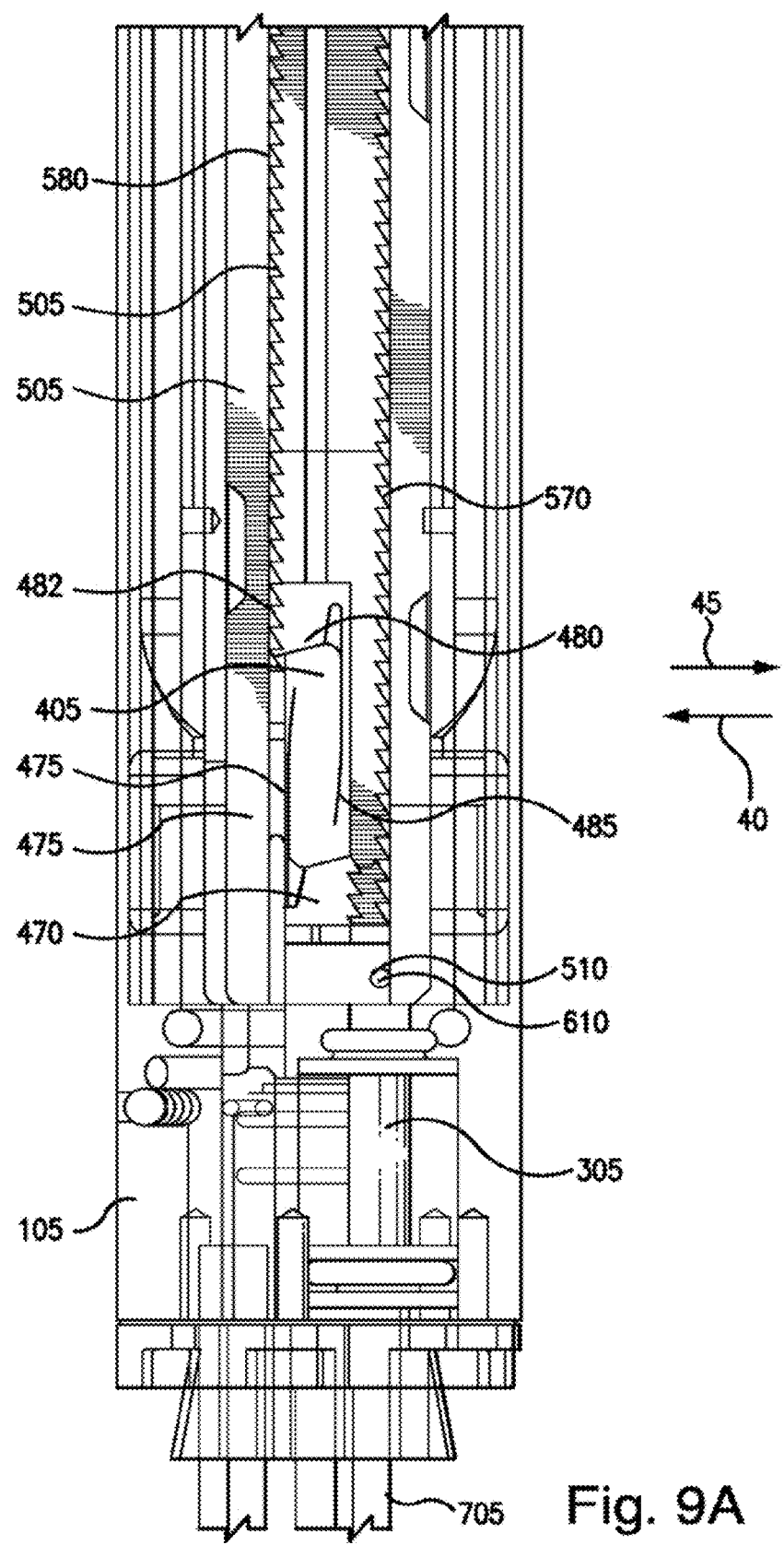
FIG. 9A is a partial top view of the device of FIG. 1.
Figure 9B:
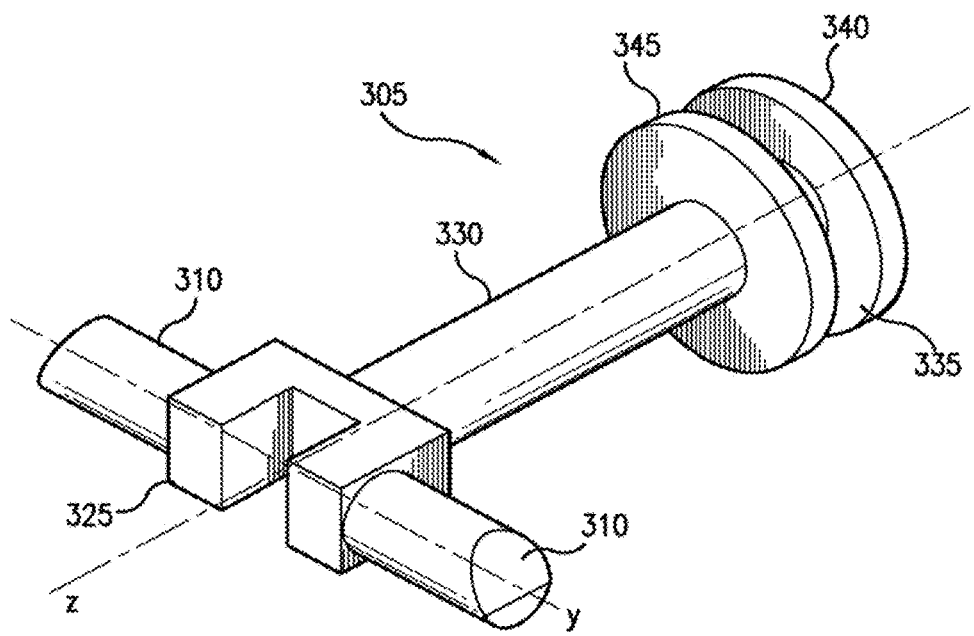
FIG. 9B shows an anvil piston of the device of FIG. 1.

The anvil 205 is rotatable about the anvil pivot pin 290 between the open orientation illustrated in FIG. 2 to a closed orientation illustrated in FIG. 4. The rotation of the anvil 205 from the open orientation to the closed orientation is actuated by a pin-in-slot arrangement. The pin elements are embodied in the device 5 as pins 310 that extend laterally from the anvil piston 305, as illustrated, e.g., in FIG. 9B. Each of the pins 310 extend from its respective base at anvil piston clevis 325 laterally outwardly to a free end. Referring to FIG. 9B, the pins 310 lie along a common axis y that is parallel to the longitudinal axis z of the anvil pivot pin 290 and perpendicular to a plane in which the anvil 205 rotates with respect to the body 105.

The anvil piston clevis 325 is coupled to an anvil piston shaft 330 having a longitudinal axis z that lies within the plane of rotation of the anvil 205 and perpendicular to the pin axis y at a proximal end portion of the anvil piston shaft 330 is an o-ring groove 335 formed between a proximal o-ring retention wall 340 and a distal o-ring retention wall 345.

Figure 7:
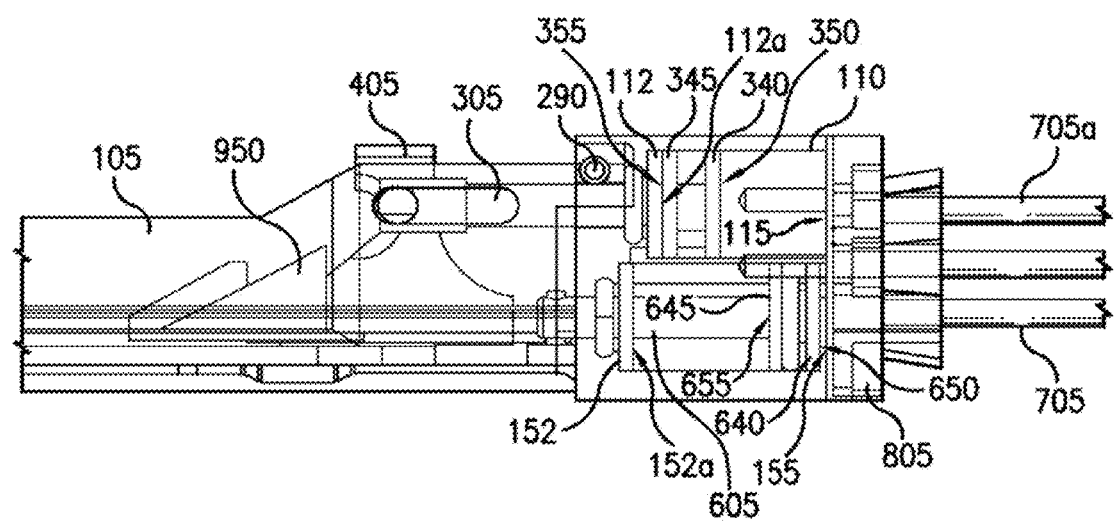
FIG. 7 is a partial side view of the body assembly of the device of FIG. 1.
Figure 8:
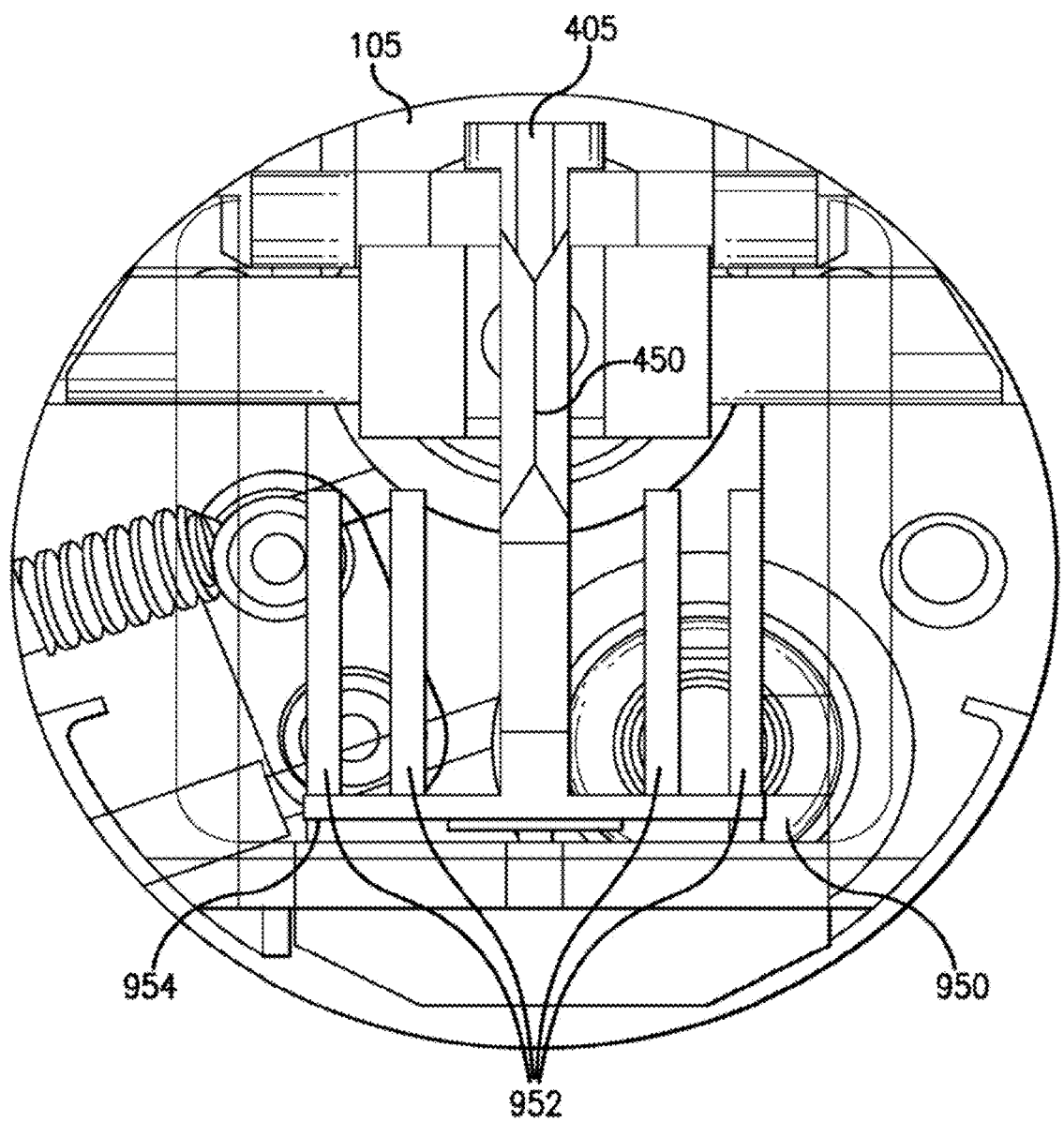
FIG. 8 is sectional front view of the device of FIG. 1.

Referring, e.g., to FIG. 7, the anvil piston 305 is disposed in the housing 105 such that the proximal portion of the anvil piston 305, including proximal and distal o-ring retention walls 340 and 345, is disposed in a first hydraulic chamber 110 of the housing 105.

The proximal and distal o-ring retention walls 340 and 345 have cylindrical outer surfaces dimensioned to have a slightly smaller diameter than the diameter of the cylindrical inner surface of the first hydraulic chamber 110 such that the anvil piston 305 is slidable between proximal and distal positions with respect to the first hydraulic chamber 110.

Figure 10A:
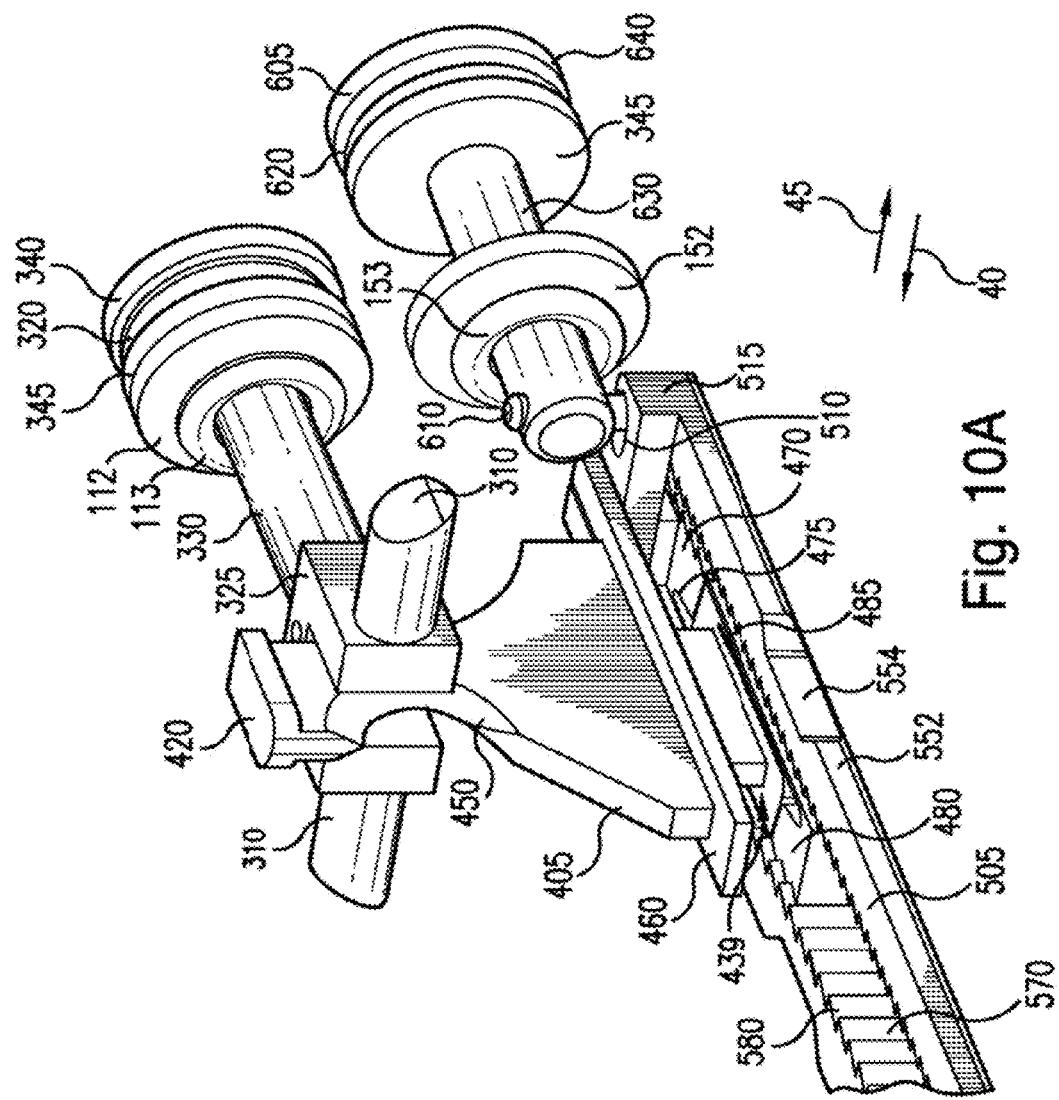
FIG. 10A shows an actuation assembly of the device of FIG. 1.

A seal is formed between the anvil piston 305 and the inner surface of the first hydraulic chamber 110 by an o-ring 320, illustrated in FIG. 10A, which is retained in the o-ring groove 335 between the proximal and distal o-ring retention walls 340 and 345. Thus, a hydraulic space or volume is defined between the proximal surface 350 of the anvil piston 305, the cylindrical side walls of the first hydraulic chamber 110 and a proximal surface 115 of the first hydraulic chamber 110. Likewise, a hydraulic space or volume is defined between the distal surface 355 of the piston anvil 305, the cylindrical side walls of the first hydraulic chamber 110 and a proximally directed surface 112a of a washer or plate 112 at the distal end of the hydraulic chamber 110. The two hydraulic volumes defined in the first hydraulic chamber 110 are sealed from each other by the anvil piston 305, including the o-ring 320. These hydraulic volumes vary inversely to each other depending on the axial position of the anvil piston 305. In particular, as the anvil piston moves distally, the volume of the distal hydraulic volume decreases and the volume of the proximal hydraulic volume increases. Similarly, as the anvil piston moves proximally, the volume of the distal hydraulic volume increases and the volume of the proximal hydraulic volume decreases.

Further, the hydraulic volume disposed proximally to the seal formed by the o-ring 320 of the anvil piston 305 is in fluid communication with a hydraulic supply tube 705a, and the hydraulic volume disposed distally to the seal formed by the o-ring 320 of the anvil piston 305 is in fluid communication with a hydraulic supply tube 705b.

The hydraulic supply tubes 705a, 705b extend proximally, e.g., in a flexible shaft, to a hand piece and/or other appropriate control unit where one or more hydraulic control units are disposed. In response to a control signal, the hydraulic control units are configured to transmit hydraulic fluid, e.g., saline, at a controlled pressure and/or flow rate into or out of the hydraulic volumes. Generally, the hydraulic drive system uses positive pressure to generate most, if not all, of the force exerted on the anvil piston 305 during both distal and proximal actuation of the anvil piston 305. In this regard, the positive pressure is applied via the first hydraulic supply tube 705a during the distal actuation of the anvil piston 305, and the positive pressure is applied via the hydraulic supply tube 705b during the proximal actuation of the anvil piston 305. It should be appreciated however, that a negative pressure may be utilized in addition to or instead of the positive pressure. However, negative pressure may be beneficial, particularly in arrangements where the pressure is transmitted by elongated tubes. Generally, as hydraulic fluid is added to one of hydraulic fluid volumes via one of the supply tubes 705a, 705b, the same amount of hydraulic fluid is withdrawn from the other hydraulic fluid volume via the other supply tube 705b, 705a, thereby providing a complementary relationship between the first and second hydraulic fluid volumes and an analogous complementary relationship between the hydraulic supply tubes 705a, 705b.

Thus, by precisely controlling the hydraulic fluid conveyed via the supply tubes 705a, 705b, the hydraulic control units are able to precisely control the movement and position of the anvil piston 305 by controlling the sealed hydraulic volumes of the first hydraulic chamber 110. This double-action piston arrangement, wherein the first and second hydraulic fluid volumes can be separately, albeit complementarily, adjusted, allows for a closed fluid system that limits the interaction of the surgical device with outside elements.

The anvil piston shaft 330 axially slides within the washer or plate 112 and an o-ring 113 disposed at the distal end of the first hydraulic chamber 110. The o-ring acts to radially support the distal portion of the anvil piston shaft 330 and forms a sliding seal between the anvil piston shaft 330 and the housing 105 to prevent any hydraulic fluid from escaping the first hydraulic chamber and to prevent any undesired fluids or other contaminants from entering the first hydraulic chamber 110. The washer 112 provides a protective layer of material between the piston 305 and the distal end of the cylinder 110.

Referring to FIG. 4, as the anvil piston 305 is distally and proximally actuated, the laterally extending pins 310 axially slide within an anvil pin slot 120, which extends parallel to the longitudinal axis a of the housing 105. Thus, the pins 310 are actuated in a direction parallel to the longitudinal axis a of the housing 105.

Figure 13A:
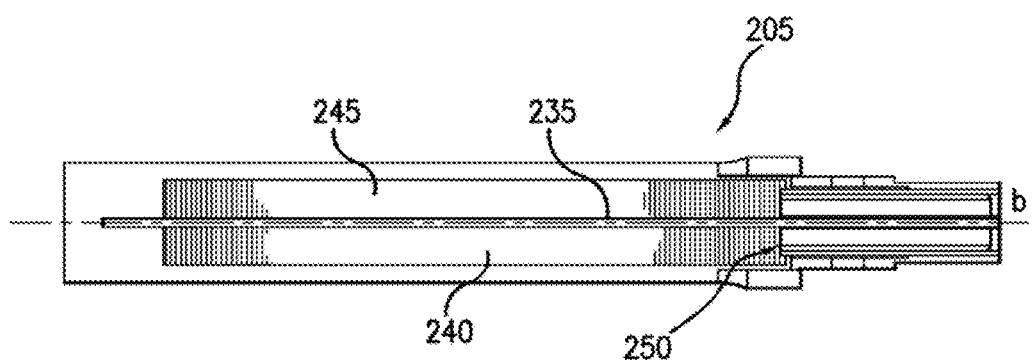
FIG. 13A is a bottom view of an anvil of the device of FIG. 1.
Figure 13B:
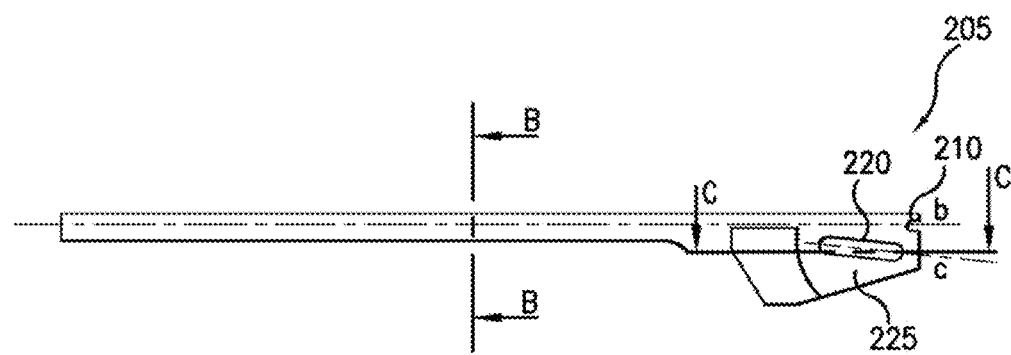
FIG. 13B is a side view of the anvil of the device of FIG. 1.
Figure 13C:
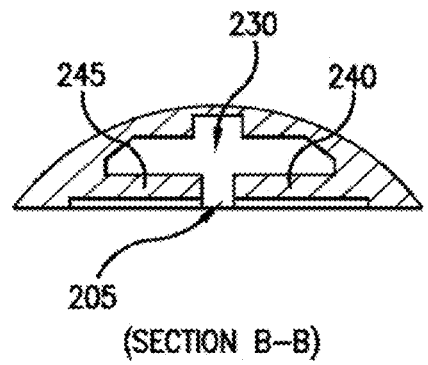
FIG. 13C is a sectional view corresponding to section B-B of FIG. 13B.
Figure 13D:
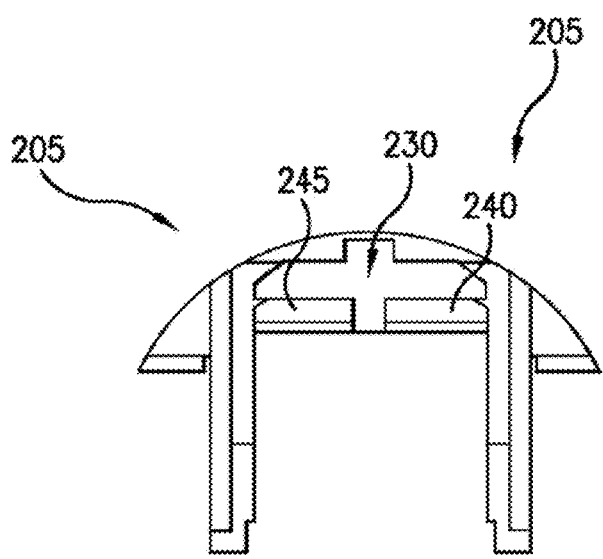
FIG. 13D is a rear view of the anvil of the device of FIG. 1.
Figure 13E:
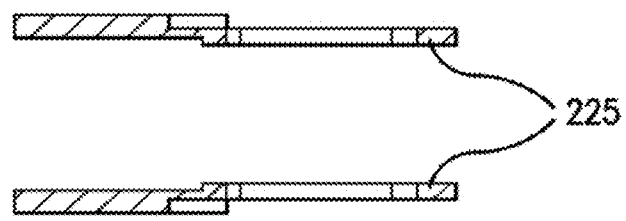
FIG. 13E is a sectional view corresponding to section C-C of FIG. 13B.
Figure 14:
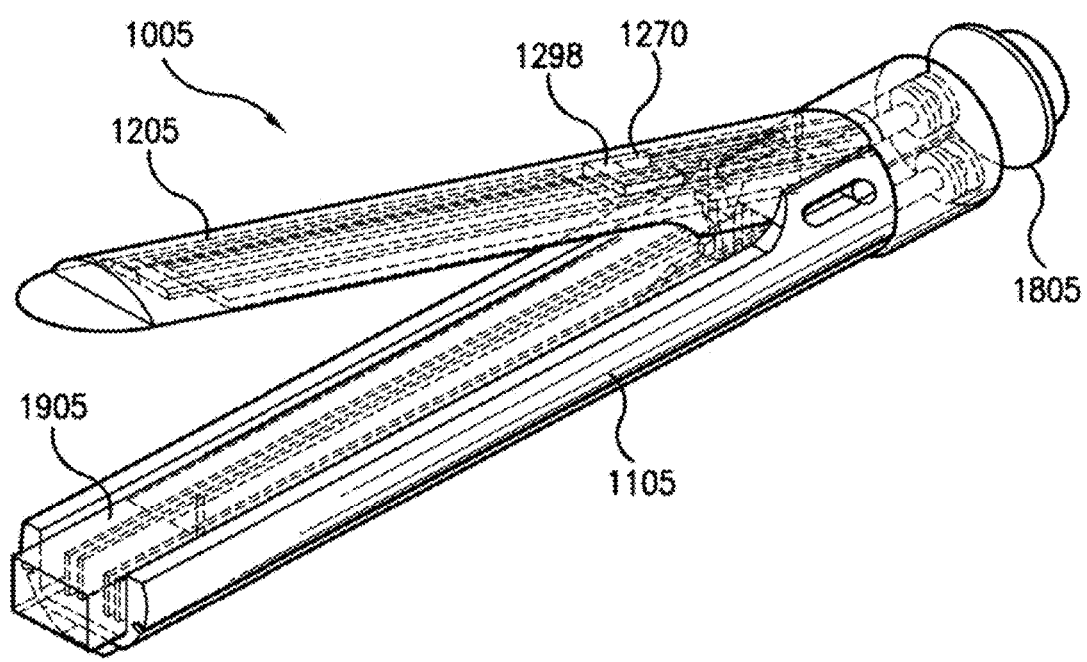
FIG. 14 is a perspective view of a surgical device according to an example embodiment of the present invention.
Figure 15:
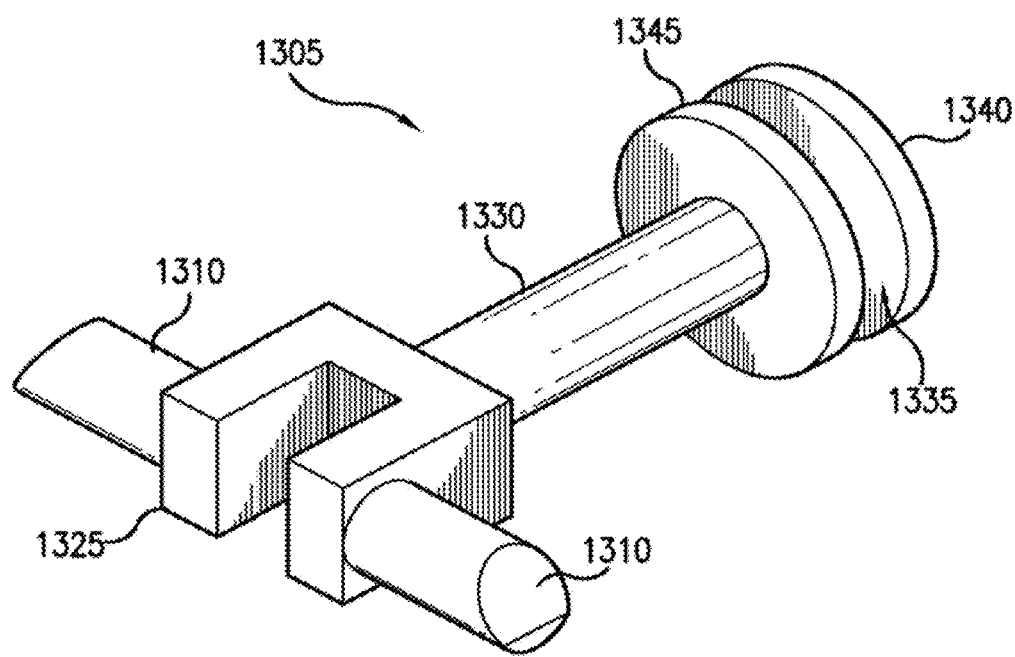
FIG. 15 shows an anvil piston of the device of FIG. 14.

Referring to FIG. 13B, the anvil 205 includes a bore 210 for receiving the anvil pivot pin 290, about which the anvil 205 rotates with respect to the housing 105 and the reload housing 905 supported by the housing 105. The anvil 205 has a longitudinal axis b that intersects the axis of rotation about the anvil pivot pin 290. The anvil 205 also includes a pair of anvil actuation slots 220 disposed on respective wings 225 of the anvil 205. Each of the anvil actuation slots 220 extends along a respective axis c that is offset from the axis of the pivot pin 290 and angled with respect to the longitudinal axis b when viewed along the rotation axis defined by anvil pivot pin 290. When the device 5 is assembled, each pin 310 extends sequentially from the anvil piston clevis 325 through the anvil actuation slot 220 of the anvil 205 and into the anvil pin slot 120 of the housing 105.

Since each of the pins 310 extend through both the anvil activation slot 220 and the anvil pin slot 120 and since the axis c of the anvil actuation slot 220 is offset from the rotation axis of the anvil 205 and angled with respect to the longitudinal axis b of the anvil 205, the distal sliding of the pins 310 within the anvil pin slots 120 causes the anvil 205 to rotate from the open position to the closed position, and the proximal sliding of the pins 310 within the anvil pin slots 120 causes the anvil 205 to rotate from the closed position to the open position. Thus, by precisely and accurately controlling the movement and position of the anvil piston 305, the hydraulic control units are able to precisely and accurately control the motion, position, and force exerted by the anvil 205.

Although distal movement of the pins 310 actuates closure of the anvil 205, it should be understood that the angle of the axis c of the anvil activation slot 220 may be provided such that proximal sliding of the pins 310 causes closure of the anvil 205 and distal sliding of the pins 310 causes opening of the anvil 205.

When the anvil 205 is in the closed position, as illustrated, e.g., in FIG. 4, the carriage 405, which is provided in the form of a force transfer bar, may be distally advanced along the longitudinal axis a of the housing 105.

Figure 10B:
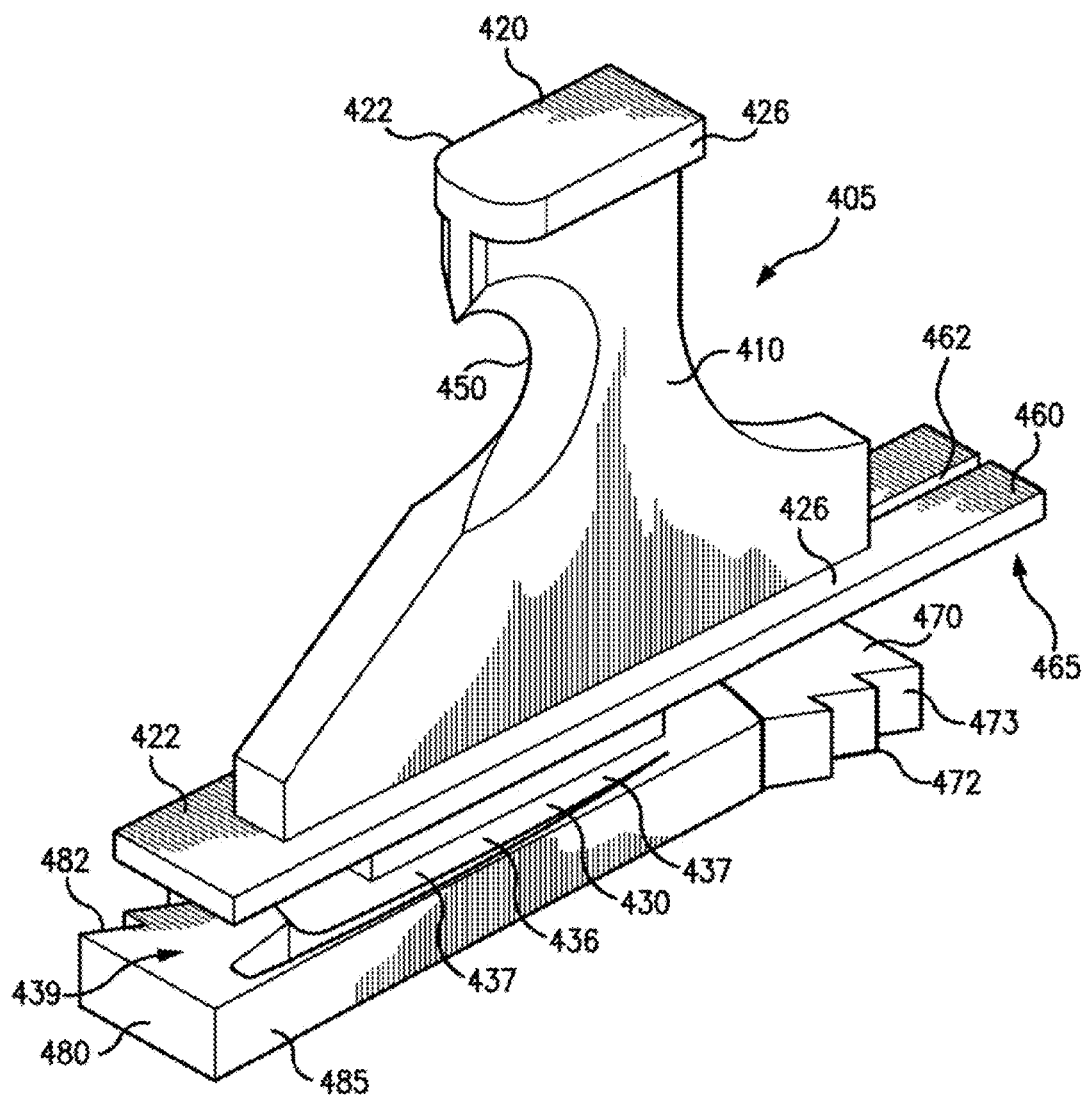
FIG. 10B shows a carriage of the device of FIG. 1.

Referring to FIGS. 10A and 10B, the carriage 405 includes a plate 410 extending between a first jaw-engagement portion 420 and a second jaw-engagement portion 430. The first jaw-engagement portion 420 is shaped as a plate oriented perpendicularly to the plate 410 and including a pair of opposed flanges 422, 426, and the second jaw-engagement portion 430 is also shaped as a plate oriented perpendicularly to the plate 410 and including a pair of opposed flanges 432, 433. Each of the flanges 422, 426, 432, 436 of the first and second jaw-engagement portions 420, 430 project transversely with respect to the plate 410 and extend longitudinally in a direction parallel to the longitudinal axis a of the housing 105 when the surgical device 5 is in its assembled configuration, as illustrated, e.g., in FIG. 4.

The second jaw-engagement portion 430 is configured to engage the lower jaw, which comprises the housing 105 and the reload housing 905 such that the carriage 405 is slidable along the longitudinal axis a of the housing 105 while being constrained from movement transverse to the longitudinal axis a of the housing 105. In this regard, the carriage 405 is configured to be coupled to the housing 105 such that the second jaw-engagement portion 430 slides below a lower plate or wall 130, illustrated, e.g., in FIGS. 11E and 11F, while the retention plate 460 is disposed above the wall 130. The wall 130 includes a guide slot 135 extending along the longitudinal axis a of the housing 105 and configured to slidably receive a guide rib 440 of the carriage 405, which extends between the second jaw-engagement portion 430 and the retention plate 460. The retention plate 460 is a removable component of the carriage 405 and includes a slot 462 that facilitates removal. It should be understood, however, that the retention plate 460 may be non-removable and/or formed as a single monolithic piece with the main body of the carriage 405.

When the guide rib 440 is received by the guide slot 135, the lower wall 130 is disposed in a gap or region 439 between opposed surfaces 437, 465 defined by the second jaw-engagement portion 430 and the retainer plate 460, thereby restraining movement of the carriage 405 transverse to the longitudinal axis a of the housing 105, as the carriage 405 slides along the guide slot 135. In particular, the surface 437 of the second jaw-engagement portion 430 and a lower surface 131 of the lower wall 130 engage each other to form a first positive stop against movement of the carriage 405 with respect to the housing 105 in a first direction transverse to the longitudinal axis a of the housing 105. Likewise, the lower surface 465 of the retainer plate 460 and a lower surface 131 of the lower wall 130 engage each other to form a second positive stop against movement of the carriage 405 in a second direction transverse to the longitudinal axis a of the housing 105, the first and second directions being within the plane in which the anvil 205 rotates between the opened and closed positions with respect to the housing 105.

Figure 11A:
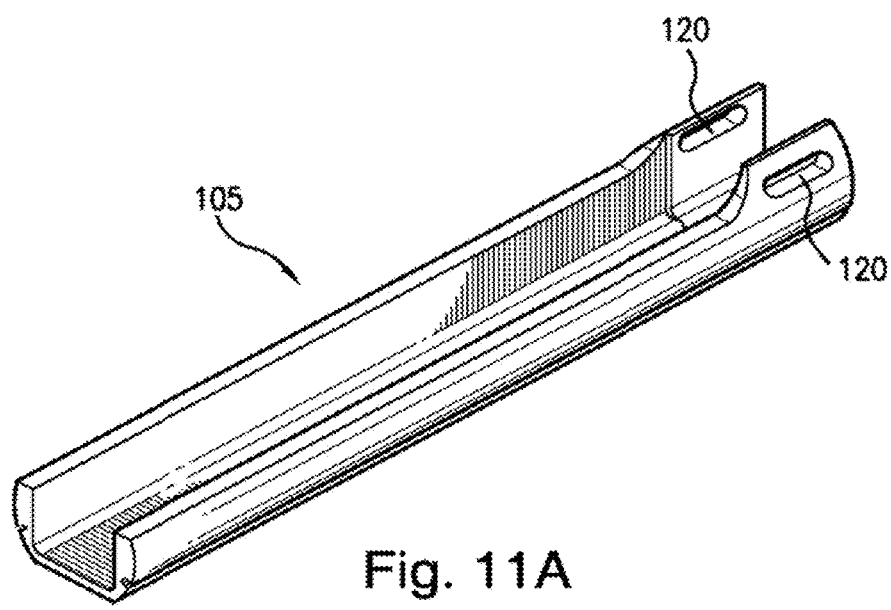
FIG. 11A shows the housing of the device of the device of FIG. 1.
Figure 11B:
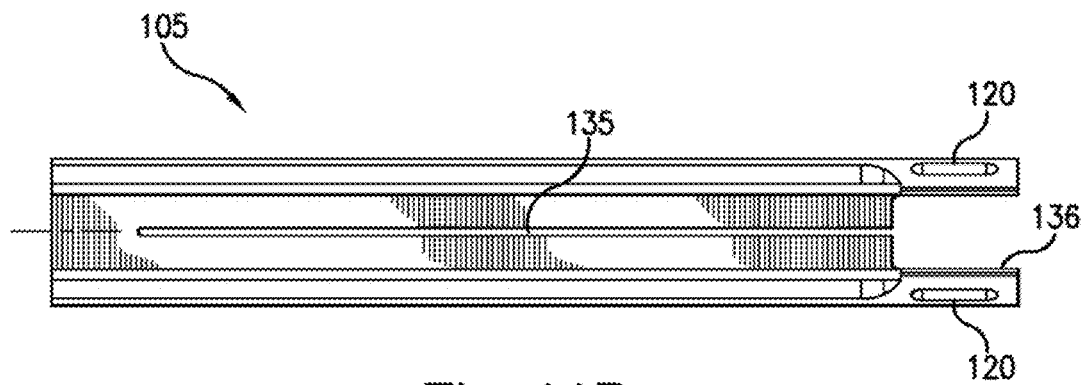
FIG. 11B is a top view of the housing of the device of FIG. 1.
Figure 11C:
FIG. 11C is a side view of the housing of the device of FIG. 1.
Figure 11D:
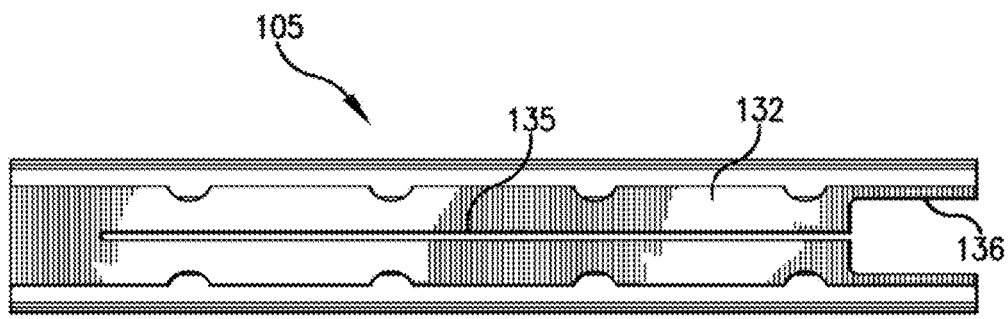
FIG. 11D is a bottom view of the housing of the device of FIG. 1.
Figure 11E:
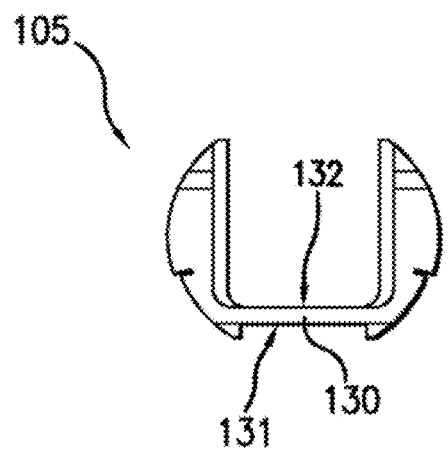
FIG. 11E is a front view of the housing of the device of FIG. 1.
Figure 11F:
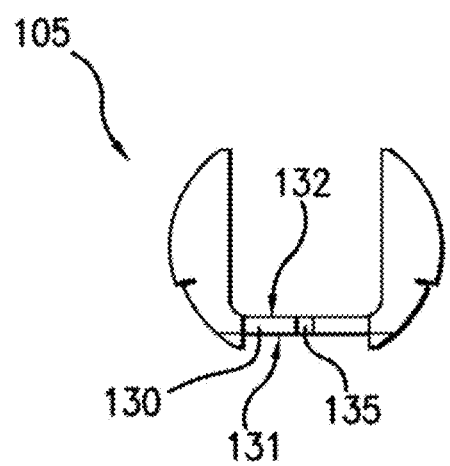
FIG. 11F is a rear view of the housing of the device of FIG. 1.

Referring to FIG. 11D, the guide slot 135 proximally extends into an enlarged opening 136 having a width in the bottom wall 130 that is greater than the width of the guide slot, thereby allowing the carriage 405 to be disengaged from the guide slot 135 when the carriage 405 is positioned in the region of the enlarged opening 136.

Figure 9C:
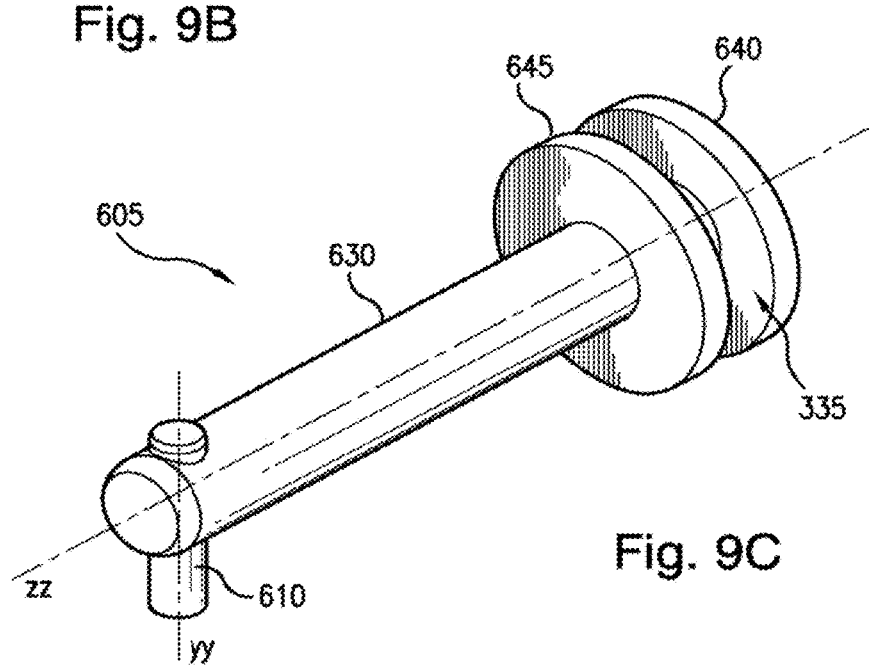
FIG. 9C shows a ratchet piston of the device of FIG. 1.
Figure 9D:
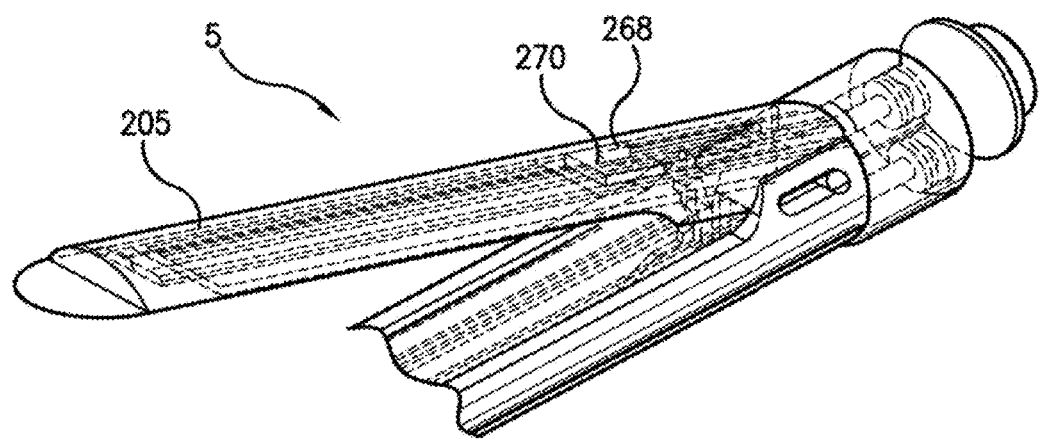
FIG. 9D is a partial view of the device of FIG. 1 showing and anvil sled assembly disposed in the anvil.
Figure 9E:
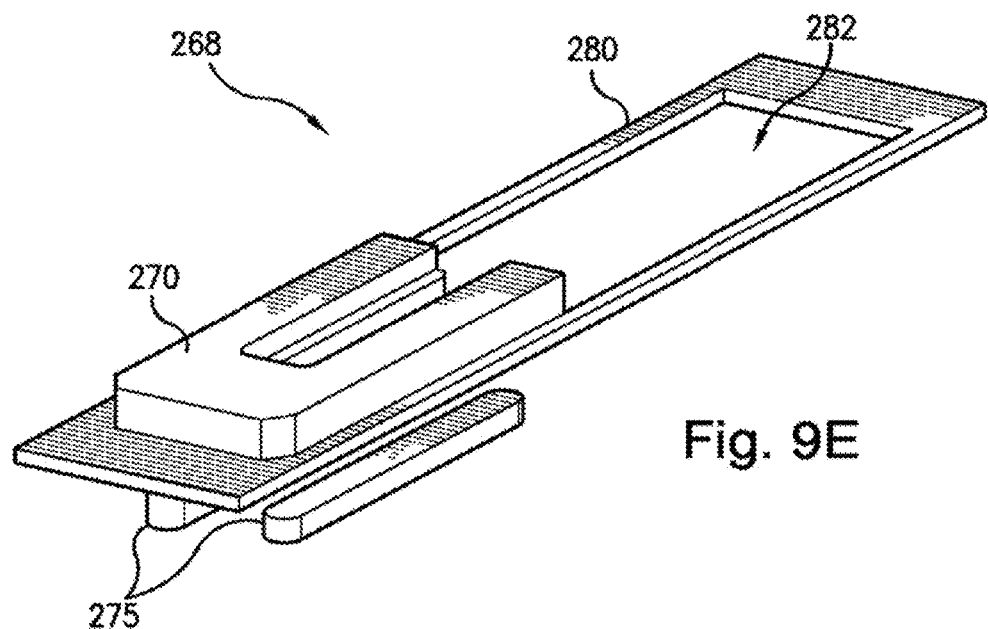
FIG. 9E is an exploded view of the anvil sled assembly of the device of claim 1.

Referring to FIGS. 13A to 13E, the anvil 205 includes a guide channel 230 that extends in the direction of the longitudinal axis b of the anvil 205, which is parallel to the longitudinal axis a of the housing 105 when the anvil 205 is in a closed state with respect to the housing 105, as illustrated in FIG. 4. Referring to FIGS. 1, 9D, and 9E, when the device 5 is assembled, the guide channel 230 receives an anvil sled assembly 268, which includes an anvil latch plate 270, a low friction insert 275, and a return link 280. The anvil sled assembly 268 is slidable within the guide channel 230 between a proximal position and a distal position. The distal and proximal directions of sliding are along the longitudinal axis b of the anvil 205, and parallel to the longitudinal axis a of the housing 105 when the anvil 205 is in the closed state with respect to the housing 105, as illustrated in FIG. 4. In FIG. 11A, the anvil sled assembly 268 is in the proximal position.

The anvil 205 includes a guide slot 235 formed between two guide flanges 240, 245 and opening proximally into an enlarged recess 240. Thus, the guide slot 235 begins at the proximal ends of the guide flanges 240, 245, as illustrated in FIG. 13A.

When the anvil sled assembly 268 and the carriage 405 are in their respective proximal positions with respect to the housing 105, the anvil 205 is rotatable to transition between its open and closed states with respect to the housing 105. When the anvil 205 rotates from the open state to the closed state, the upper jaw-engagement portion 420 of the carriage passes through an enlarged opening 282 in the return link 280 of the anvil carriage 468 and into the enlarged recess 250 of the anvil 205. In this regard, the enlarged opening 282 and the enlarged recess 250 are laterally dimensioned to allow clearance between the carriage 405 and any structure of the anvil 205 or the anvil sled assembly 268 during opening and closing of the anvil with respect to the housing 105 when the anvil sled assembly 268 and the carriage 405 are in their respective proximal positions.

During a surgical procedure, the anvil sled assembly 268 and the carriage 405 are in their respective initial proximal positions whenever the anvil 205 is closed and opened with respect to the housing 105 to thereby respectively clamp and release tissue between the anvil 205 and the housing 105 via actuation of the anvil piston 305 as set forth in greater detail above.

After the anvil 205 is closed with respect to the housing 105 to clamp a portion of tissue between the anvil 205 and the housing 105, the carriage 405 is distally advanced in order to cut and staple the clamped portion of tissue.

In order to distally advance the carriage 405, which at this stage is in its proximal position with respect to the housing 105 with the first jaw-engagement portion extending through the enlarged opening 282 in the return link 280 and into the recess 250 of the anvil 205, a reciprocating arrangement, in the form of a ratcheting arrangement, is actuated via the ratchet actuation piston 605.

The ratchet actuation piston 605 includes features analogous to the anvil piston 305 described above and is proximally and distally actuated functions in the same general manner as the anvil piston 305 described above. Referring to FIG. 9C, the ratchet actuation piston 605 includes a ratchet actuation piston shaft 630 having a longitudinal axis zz that is parallel to the longitudinal axes a, z of the housing 105 and the anvil piston 305. At a proximal end portion of the ratchet piston shaft 630 is an o-ring groove 635 formed between a proximal o-ring retention wall 640 and a distal o-ring retention wall 645.

Referring, for example, to FIG. 7, the ratchet actuation piston 605 is disposed in the housing 105 such that the proximal portion of the ratchet actuation piston 605, including proximal and distal o-ring retention walls 640 and 645, is disposed in a second hydraulic chamber 150 of the housing 105. The proximal and distal o-ring retention walls 640 and 645 have cylindrical outer surfaces dimensioned to have a slightly smaller diameter than the diameter of the cylindrical inner surface of the second hydraulic chamber 150 such that the ratchet actuation piston 605 is slidable between proximal and distal positions with respect to the second hydraulic chamber 150.

A seal is formed between the ratchet actuation piston 605 and the inner surface of the second hydraulic chamber 150 by an o-ring 620, illustrated, e.g., in FIG. 10A, which is retained in the o-ring groove 635 between the proximal and distal o-ring retention walls 640 and 645. Thus, a hydraulic space or volume is defined between the proximal surface 650 of the ratchet actuation piston 605, the cylindrical side walls of the second hydraulic chamber 150 and a proximal surface 155 of the second hydraulic chamber 150. Likewise, a hydraulic space or volume is defined between the distal surface 655 of the ratchet actuation piston 605, the cylindrical side walls of the second hydraulic chamber 150 and a proximally directed surface 152a of a washer or plate 152 at the distal end of the hydraulic chamber 150. The two hydraulic volumes defined in the second hydraulic chamber 150 are sealed from each other by the ratchet piston 605, including the o-ring 620. These hydraulic volumes vary inversely to each other depending on the axial position of the ratchet piston 605. In particular, as the ratchet piston moves distally, the volume of the distal hydraulic volume decreases and the volume of the proximal hydraulic volume increases. Similarly, as the ratchet piston 605 moves proximally, the volume of the distal hydraulic volume increases and the volume of the proximal hydraulic volume decreases.

Since the proximal walls 115, 155 of the hydraulic chambers 110, 150 are part of the rear cap 805, a cylinder gasket 825 is provided at an interface between the housing 105 and the rear cap 805 to form a seal therebetween when the housing 105 and the end cap are joined (e.g., via screws 850). Further, the cylinder gasket 825 is partially exposed to the interior of each of the hydraulic chambers 110, 150, thereby providing a barrier between the proximal surfaces 350, 650 of the cylinders 305, 605 and the respective proximal walls 115, 155 to thereby protect the respective components 305, 605, 805 against damage or wear that would otherwise be due to direct impact between the proximal surfaces 350, 650 of the cylinders 305, 605 and the respective proximal walls 115, 155 by absorbing energy. Likewise, the washers 112, 152 provide analogous protection to the cylinders 305, 605 and the housing 105 by preventing direct impact between the distal surfaces 355, 655 of the pistons 305, 605 and the housing 105 during distal or forward strokes of the pistons 305, 605. These elements 805, 112, 152 may be made of any suitable materials, including, e.g., one or more elastomers.

Moreover, these elements 805, 112, 152 may be formed of the same material, or one or more of these elements 805, 112, 152 may be formed of a different material than one or more of the other elements 805, 112, 152.

Further, the hydraulic volume disposed proximally to the seal formed by the o-ring 620 of the ratchet piston 605 is in fluid communication with a hydraulic supply tube 705c. The hydraulic supply tubes 705c, 705d extend proximally, e.g., in a flexible shaft, to the hand piece or other appropriate control unit where hydraulic control units are disposed. In response to a control signal, the hydraulic control units are configured to transmit hydraulic fluid, e.g., saline, at a controlled pressure and/or flow rate into or out of the hydraulic volumes of the second hydraulic chamber 150. As with the driving of the anvil piston 305 described above, the hydraulic drive system generally uses positive pressure to generate most, if not all, of the force exerted on the ratchet piston 605 during both distal and proximal actuation of the ratchet piston 605. In this regard, the positive pressure is applied via the first hydraulic supply tube 705c during the distal actuation of the ratchet piston 605, and the positive pressure is applied via the hydraulic supply tube 705d during the proximal actuation of the ratchet piston 605. However, as with the actuation of the anvil piston 305 described above, it should be appreciated that a negative pressure may be utilized in addition to or instead of the positive pressure. Generally, as hydraulic fluid is added to one of hydraulic fluid volumes via one of the supply tubes 705c, 705d, the same amount of hydraulic fluid is withdrawn from the other hydraulic fluid volume via the other supply tube 705d, 705c, thereby providing a complementary relationship between the first and second hydraulic fluid volumes and an analogous complementary relationship between the hydraulic supply tubes 705c, 705d.

Thus, by precisely controlling the hydraulic fluid conveyed via the supply tubes 705c, 705d, the hydraulic control units are able to precisely control the movement and position of the ratchet piston 605 by controlling the sealed hydraulic volumes of the second hydraulic chamber 150.

Figure 12A:
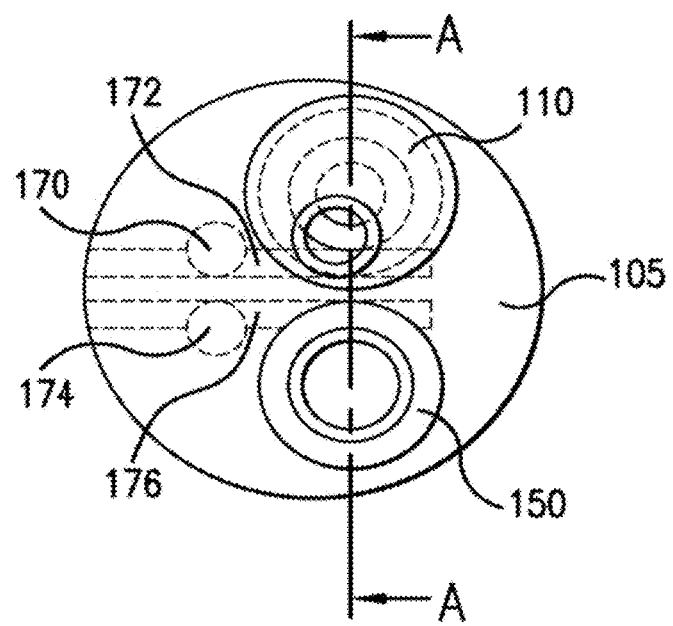
FIG. 12A is a front view of a body cylinder block of the body assembly of the device of FIG. 1.
Figure 12B:
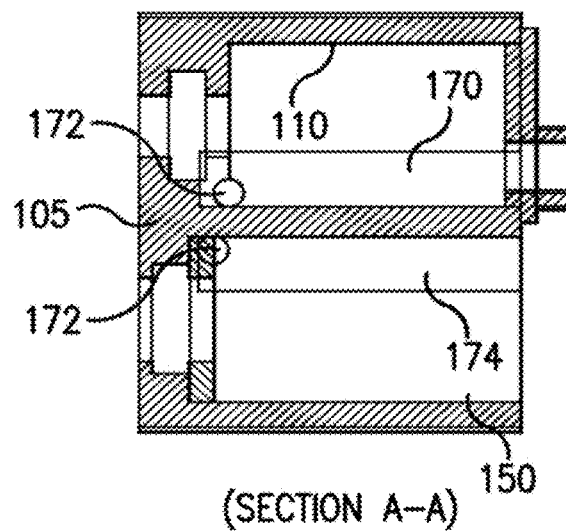
FIG. 12B is a sectional view corresponding to section A-A of FIG. 12A.

Referring to FIGS. 12A and 12B, the hydraulic fluid from the tube 705b is transmitted between the chamber 110 and the tube 705b via a set of interconnected bores 170, 172. In this regard, the fluid would travel along an axial supply bore 170, which extends parallel to and spaced apart from the cylinder 110, to a distal transverse supply bore 172, which connects the axial supply bore 170 and the distal end region first cylinder 110. Thus, the tube 705b is able to supply and remove hydraulic fluid to and from the distal end region of the cylinder 110.

Likewise, the hydraulic fluid from the tube 705d is transmitted between the chamber 150 and the tube 705d in a set of interconnected bores 174, 176. The fluid would travel along an axial supply bore 174, which extends parallel to and spaced apart from the cylinder 150, to a distal transverse supply bore 176, which connects the axial supply bore 172 and the distal end region first cylinder 150. Thus, the tube 705d is able to supply and remove hydraulic fluid to and from the distal end region of the cylinder 150.

Referring to FIG. 12A the bores 172, 176 are shown as providing an opening from the housing on the left side of the illustration. However, the extension of the bores 174 and 176 to the left of the bores 172, 174 in FIG. 4 is due to the formation of the bores 172, 176 by drilling two respective transverse holes into the side of the housing 105, one that extends into both the bore 170 and the cylinder 150, and another that extends into both the bore 174 and the cylinder 150. If either bore 174, 176 is formed in this manner, the portion of the bore 174, 176 that extends through the outer surface of the housing 105 may be sealed in any appropriate manner, e.g., filling the bore with a pin, dowel, filler, adhesive and/or other suitable material.

The tubes 705a and 705c provide hydraulic fluid to the respective cylinders 110, 150 via respective proximal bores in the rear cap 805 of the housing assembly. These bores are concentric with the respective tubes 705a, 705c. It should be understood, however, that the delivery mechanism between the tubes 705a, 705b, 705c, 705d and the respective regions of the cylinders 110, 150 may vary from the example embodiments.

The ratchet actuation piston shaft 630 axially slides within the washer 152 and an o-ring 153 disposed at the distal end of the second hydraulic chamber 150. The o-ring 152 acts to radially support the distal portion of the ratchet actuation piston shaft 630 and forms a sliding seal between the ratchet actuation piston shaft 630 and the housing 605 to prevent any undesired fluids or other contaminants from entering the second hydraulic chamber 150. The washer 152 provides a protective layer of material between the piston 605 and the distal end of the cylinder 150.

Referring to FIG. 9C, the ratchet actuation piston 605 includes a force transfer pin 610 extending through a transverse bore in the ratchet actuation piston shaft 630. Thus, the longitudinal axis yy of the force transfer pin 610 that received in the bore as illustrated in FIG. 9C is transverse and perpendicular to the longitudinal axis zz of the ratchet actuation piston 605.

When the device 5 is assembled, the force transfer pin 610 of the ratchet actuation piston 605 is received in a force transfer slot 510 in a proximal transversely extending member 515 of the actuating bar 505. The engagement between the force transfer pin 610 and the force transfer slot 510 is shown, for example, in FIG. 10A. The force transfer pin 601 is dimensioned slightly smaller that the width of the force transfer slot 510, which extends transversely and perpendicularly with respect to the longitudinal axis zz, and therefore the reciprocating strokes, of the oscillating ratchet actuation piston 605. Thus, the longitudinally directed reciprocating strokes of the ratchet actuation piston 605 also cause corresponding longitudinally directed strokes of the actuating bar 505, while the actuating bar 505 remains slidable with respect to the force transfer pin 610 along the length of the force transfer slot 510, regardless of where along the length of the slot 510 the force transfer pin 610 is located. For example, in FIG. 10A the actuating bar 505 has been moved in a first lateral direction 40 with respect to the ratchet actuation piston 605 so that the force transfer pin 610 is disposed at a first end of the force transfer slot 510. FIG. 9A shows the actuating bar 505 after being moved in a second, opposite lateral direction 45 with respect to the ratchet actuation piston 605 so that the force transfer pin 610 is disposed at a second, opposite end of the force transfer slot 510. As set forth in greater detail below, which of these two lateral positions the force transfer bar 505 is in with respect to the ratchet actuation piston 605 will determine whether the carriage 405 is driven distally or proximally along the longitudinal axis a of the housing 105.

In via the reciprocating drive mechanism, the carriage 405 is continuously actuated substantial axial distances while the driving mechanism remains is a relatively confined axial location.

As set forth above, when the device 5 is assembled and the carriage 405 is engaged with the guide slot 135, the second jaw engagement portion 430 is disposed below the lower plate 130 of the housing 105. In addition to the second jaw-engagement portion 430, first and second ratcheting elements 470, 480 are also disposed below the lower plate 130 when the carriage 405 is engaged with the guide slot 135. The ratcheting elements 470, 480 are coupled to the second jaw-engagement portion 430 by respective spring arms 475, 485.

The actuating bar 505 is also disposed below the lower plate 130 of the housing 105. In this regard, the actuating bar 505 is slidably disposed between and supported by the housing 105 and the cover 180 attached to the housing 105. The housing 105, rear cap 805, and the cover 180 form a housing assembly 105, 180, 805 when the device 5 is assembled. In this regard, features described herein with regard to the housing 105, the cover 180, and the rear cap 805 generally also refer to features of the housing assembly 105, 180, 805 as an overall unit. Further, the features described herein with regard to the housing 10, the cover 180, and the rear cap 805 need not be provided on the particular element 105 or 180 indicated. For example, although the alignment elements 160a, 160b described below are discussed as part of the housing 105, it should be understood that these elements 160a, 160b are part of the housing assembly 105 as a whole and that one, more, or all of these elements 160a and/or 160b may be provided on other elements of the housing assembly 105, 180, e.g., on the cover 180. Further, the housing assembly 105, 180, 805 may be provided as a single component or having additional components than those described with regard to the illustrated examples.

As illustrated in FIG. 10A, the actuating bar 505 has been moved in the first lateral direction 40 so that the actuating bar is in a first later position with respect to the carriage 405 and the housing 105. In the first lateral position, a set of ratcheting teeth 472 of the first ratchet element 470 engage a corresponding first set of teeth 572 of the actuating bar 505. The engagement between the teeth 472 and 572 is such that the first set of teeth 572 of the actuating bar 505 lock with the teeth 472 of the first ratcheting element 470 when the actuating bar 505 is in each distal stroke of reciprocation but not when the actuating bar is in each proximal stroke. Thus, each distal stroke of the reciprocation of the actuating bar 505 pushes the carriage 405 an incremental distal distance along the guide slot 135 with respect to the housing 105. However, each proximal stroke of the reciprocation allows the first set of teeth 572 of the actuating bar 505 to slide over the first set of teeth 472 of the first ratcheting element 470, due to ramped surfaces of the teeth 472 and 572. Thus, the actuating bar 505 is allowed to move proximally during each proximal stroke of the reciprocation of the actuating bar 505 without causing any substantial proximal translation of the carriage 405. Thus, each reciprocation cycle (one distal stroke plus one proximal stroke) of the actuating bar 505 causes the carriage 405 to move a net incremental distal distance. Thus, upon repeating the reciprocation cycle of the actuating bar 505, the carriage 405 is distally progressed. Via this ratcheting mechanism, the carriage 405 is distally actuatable along the guide slot 135 with respect to the housing 105 when the actuating bar is in the first lateral position.

In order to proximally translate the carriage 405 with respect to the housing 105, an analogous ratcheting mechanism is engaged by moving the actuating bar 505 to its second lateral position, as illustrated in FIG. 9A, so that the second set of teeth 582 of the actuating bar 505 engages the teeth 482 of the second ratcheting element 480. However, the orientation of the teeth 482, 582 is reversed. Thus, the engagement between the teeth 482 and 582 is such that the second set of teeth 582 of the actuating bar 505 lock with the teeth 482 of the second ratcheting element 480 when the actuating bar 505 is in each proximal stroke of reciprocation but not when the actuating bar 505 is in each distal stroke. Thus, each proximal stroke of the reciprocation of the actuating bar 505 pulls the carriage 405 an incremental proximal distance along the guide slot 135 with respect to the housing 105. However, each distal stroke of the reciprocation allows the second set of teeth 582 of the actuating bar 505 to slide over the teeth 482 of the second ratcheting element 480, due to ramped surfaces of the teeth 482 and 582. Thus, the actuating bar 505 is allowed to move proximally during each proximal stroke of the reciprocation of the actuating bar 505 without causing any substantial distal translation of the carriage 405. Thus, each reciprocation cycle (one distal stroke plus one proximal stroke) of the actuating bar 505 causes the carriage 405 to move a net incremental distal distance. Thus, upon repeating the reciprocation cycle of the actuating bar 505, the carriage 405 is proximally progressed. Via this ratcheting mechanism, the carriage 405 is proximally actuatable along the guide slot 135 with respect to the housing 105 when the actuating bar is in the second lateral position.

Since each of the ratcheting elements 470, 480 is spring biased by the spring arms 475, 480 toward the respective set of teeth 572, 582 when the actuating bar 505 is in the respective first and second positions, the teeth 472, 482 of the first and second ratchet elements 470, 480 are able to laterally flex along the contour formed by the teeth 572, 582 to allow the ratcheting action.

Figure 10C:
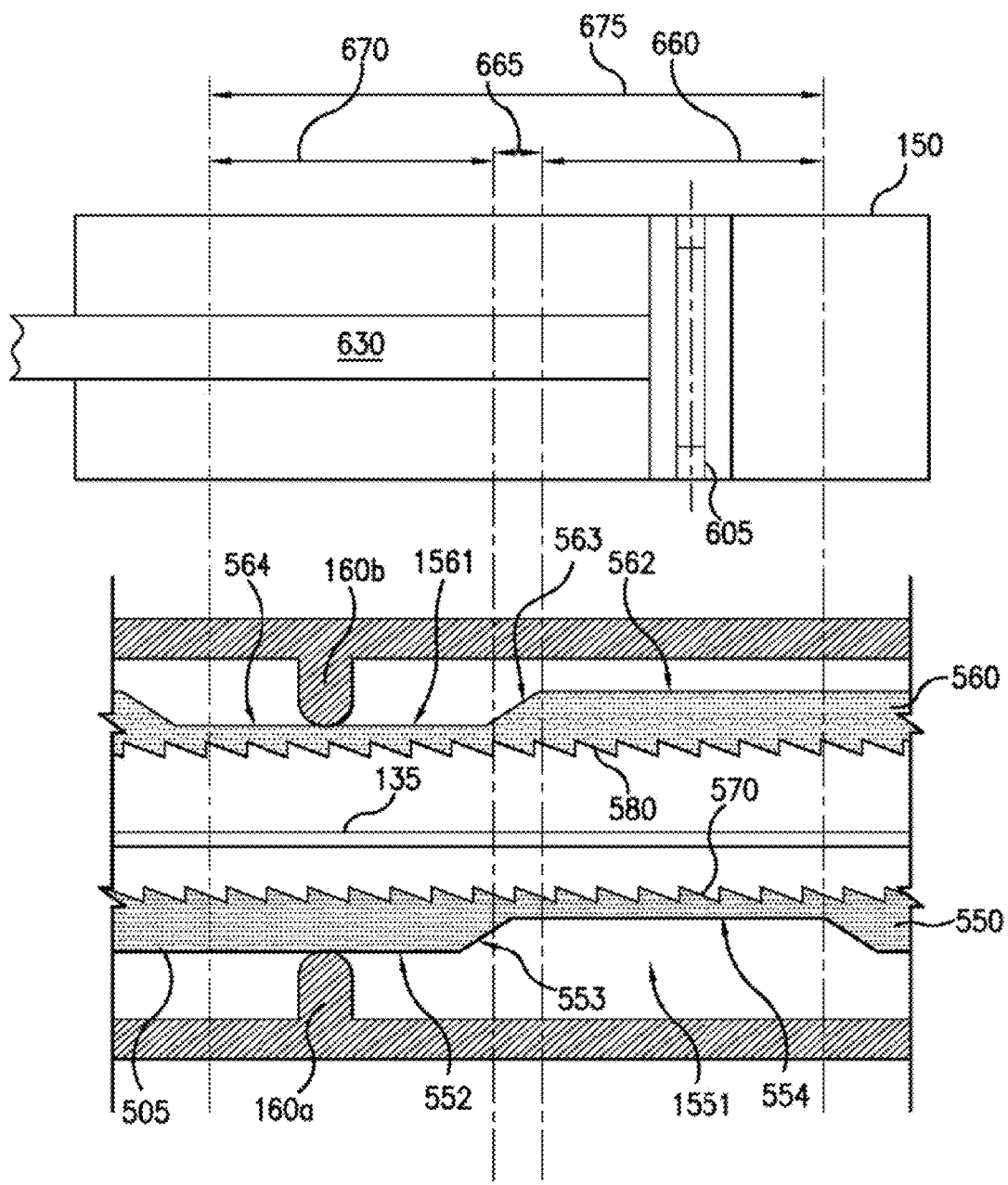
FIGS. 10C to 10E schematically show the relationship between the ratchet piston position and the position of the actuating bar with respect to the housing of the device of claim 1.
Figure 10D:
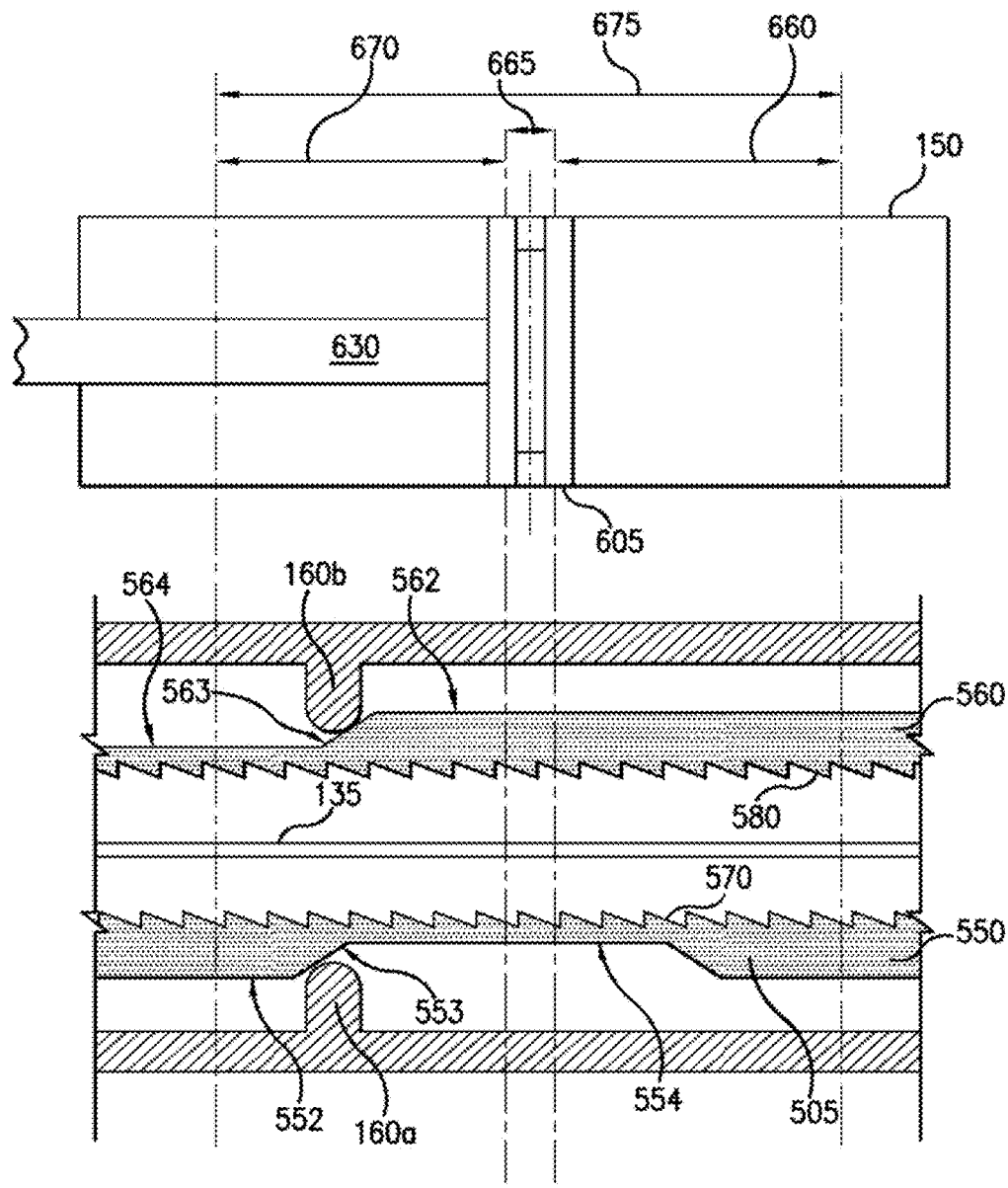
Figure 10E:
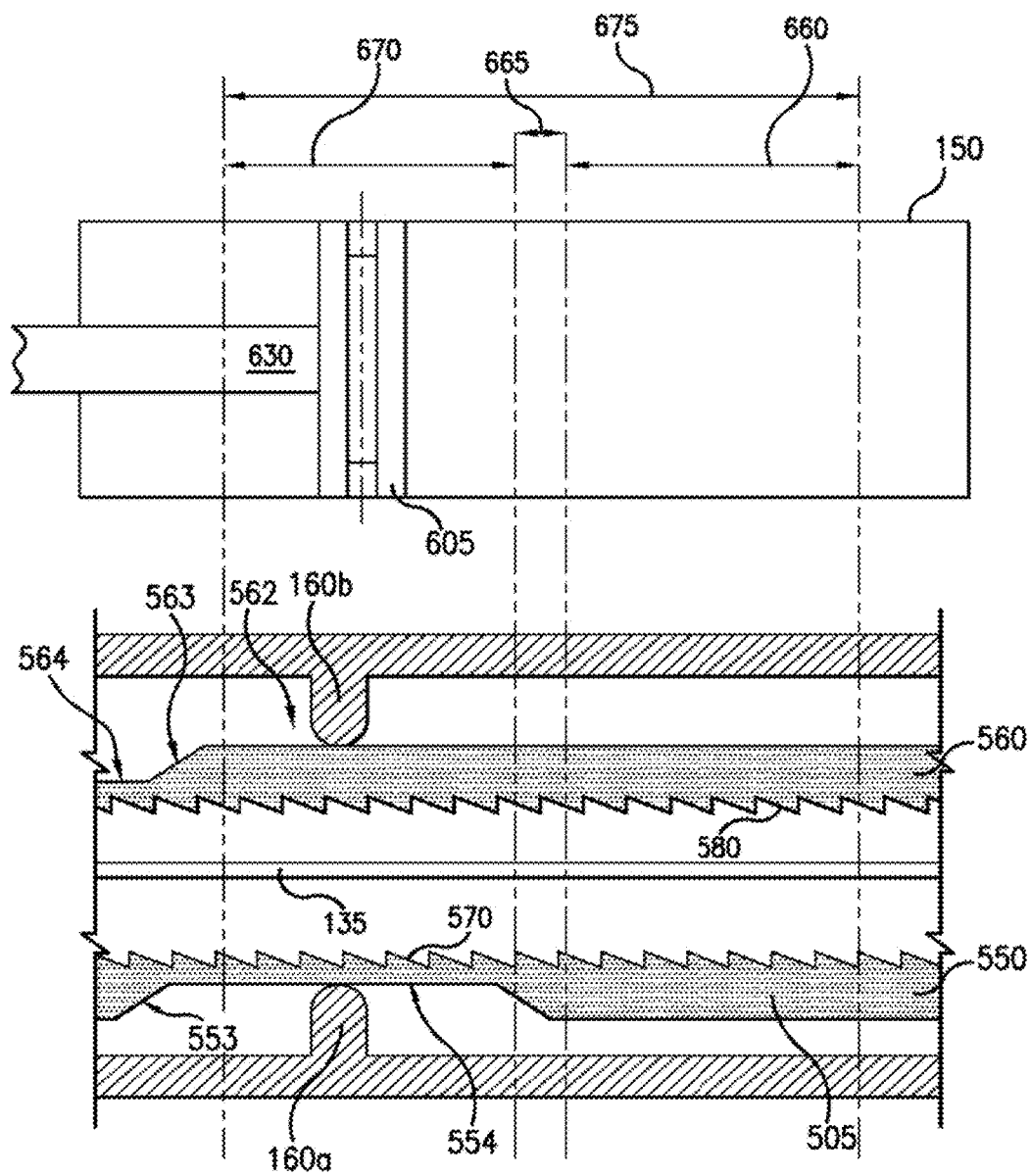

Referring to the schematic illustrations of FIGS. 10C to 10E, in order to move the actuating bar 505 from the first lateral position to the second lateral position, the ratchet piston 605 moves within its total axial stroke range 675 in the second hydraulic chamber 150 from a first axial region 660, in which the reciprocation is performed for distal actuation, to a second axial region 670, in which the reciprocation is performed for proximal actuation. Between the first and second axial regions 660, 670 is a transition region 665. In FIGS. 10C to 10E, to facilitate illustration, the position of the ratchet piston 605 is schematically superimposed above the actuating bar 505, which axially tracks the movement of the ratchet piston 605. Thus, as schematically illustrated in FIGS. 10C to 10E any axial displacement of the ratchet piston 605 corresponds to the exact same amount of axial displacement of the actuating bar 505.

Further, the actuating bar 505 is shown in its position relative to the housing 105, in which the actuating bar 505 is slidably supported. In this regard, the actuating bar is constrained in its lateral position each of FIGS. 10C to 10E by a pair of opposed alignment elements 160a, 160b in the form of radially inwardly directed projections. It is noted that although alignment elements 160a, 160b are each part of respective sets of alignment elements 160a, 160b of the housing 105, only one alignment element 160a and one alignment element 160b are shown, along with the corresponding portions of the actuating bar 505 for ease of illustration.

Referring to FIG. 10C, the ratchet piston 605 is in the first axial region 660. When the ratchet piston 605 is in the first axial region 660, the actuating bar 505 is laterally constrained by the opposed alignment elements 160a, 160b such that the alignment element 160a is slidable along an outward surface 552 of a first axial member 550 of the actuating bar 505, and the alignment element 160b is slidable along a recessed surface 564 of a second axial member 560 of the actuating bar 505. The outward surface 552 and the recessed surface 554 axially extend along lines parallel to each other as well as the guide slot 135 and the longitudinal axis a of the housing 105, the arrangement of the first set of teeth 570 of the actuating bar 505 and the second set of teeth 575 of the actuating bar 505. In this regard, when the device 5 is assembled, the outward surface 552 of the actuating bar 505 is a greater lateral distance from the longitudinal axis of the guide slot 135 than the recessed surface 554 of the actuating bar 505, and the outward surface 562 of the actuating bar 505 is a greater lateral distance from the longitudinal axis of the guide slot 135 than the recessed surface 564 of the actuating bar 505.

As the actuating bar 505 moves axially with respect to the housing 105, the alignment elements 160a follow a first surface profile of the actuating bar 505 that includes the outward surface 552, the recessed surface 554 and a ramped transition surface 553 disposed between and being continuous with the outward surface 552 and the recessed surface 554. Simultaneously, the alignment elements 160b follow a second surface profile of the actuating bar 505 that includes the outward surface 562, the recessed surface 564 and a ramped transition surface 563 disposed between and being continuous with the outward surface 562 and the recessed surface 564.

The outward surfaces 552, 562 correspond to opposite laterally outwardly facing sides of the actuating bar 505. The recessed surfaces 554 and the ramped transition surface 553 are part of an alignment recess 551 of the first axial member 550 that is recessed with respect to the outward surface 552. Likewise, recessed surface 564 and the ramped transition surface 563 are part of an alignment recess 551 of the second axial member 560 that is recessed with respect the outward surface 552. Further, the illustrated first recessed portion 551 and second recessed portion 561 form an axially offset pair of opposed recesses 551, 561. The illustrated pair of opposed recesses 551, 561 is one of three such pairs of opposed recesses 551, 561 disposed along the length of the actuating bar 505 of the illustrated example device of FIG. 1. Each recess 551, 561 as well as respective outward surfaces 552, 562 and projections 160a, 160b functions in the same or analogous manner to the corresponding elements illustrated in FIGS. 10C to 10E. It should be understood that the recesses 552, 562, or other geometry may differ from the illustrated examples. For example, there may be more or less recesses 561, 562 and their may be a greater number of recesses 561, 562 disposed on one axial member 550, 560 than the other axial member 560, 550. Moreover, the recesses 552, 562 may have differing geometries and/or irregular spacing, and/or the opposed alignment projections 160a, 160b of one or more opposed pair of alignment projections 160a, 160b may be axially offset from each other.

As illustrated in FIG. 10C, the actuating bar is in the first lateral position, such that the first set of teeth 570 of the actuating bar are closer to the guide slot 135 than the second set of teeth 580 of the actuating bar 505. In this position the first set of teeth 570 are in engagement with the corresponding teeth 472 of the first ratcheting element 470 of the carriage 405. Since the outward surface 552 and the recessed surface 564 have a length that corresponds at least approximately to the length of the first axial region 660 of the ratchet piston 605, the reciprocation of the ratchet piston 605 between proximal and distal positions within the first axial region 660 causes the actuating bar 505 to also reciprocate between corresponding proximal and axial positions while remaining in the first lateral position. Thus, the ratcheting engagement between the first set of teeth 570 (which are disposed along the first axial member 550) and the first ratcheting element 470 is maintained during the reciprocation of the ratchet piston 605 and the actuating bar 505 when the ratchet piston is within its first axial region 660. Thus, the distal movement of the carriage 405 is effected by the reciprocation of the ratchet piston 605 between proximal and distal positions within the first axial range 660.

In order to move the carriage 405 proximally, the device 5 must laterally shift the actuating bar 505 from the first lateral position (illustrated, e.g., in FIG. 10C) to the second lateral position (illustrated, e.g., in FIG. 10E) with respect to the track 135 along which the carriage 405 is distally and proximally progressed.

Referring to FIG. 10D, the lateral shifting of the actuating bar 505 between the first and second lateral positions is achieved by extending the ratchet piston 605, and therefore also the actuating bar 505, from the first region 660, over the transition region 665 disposed between the first and second regions 660, 670, and into the second region 670.

FIG. 10E illustrates the ratchet piston 605 and the actuating bar 505 in the transition axial region 665. In this transient position, the first alignment element 160a is configured to laterally constrain the actuating bar 505 by contacting the ramped transition surface 553 of the first axial member 550, while the second alignment element 160b is configured to laterally constrain the actuating bar 505 by contacting the ramped transition surface 563. Since the alignment member 160a acts as a cam follower following a cam surface defined by the outward surface 552, the ramped transition surface 553, and the recessed surface 554 and the alignment member 160b acts as a cam follower following a cam surface defined by the outward surface 562, the ramped transition surface 563, and the recessed surface 564, the actuating bar 505 is guided, via the ramped transition between the first later position illustrated, e.g., in FIG. 10C, and the second later position illustrated, e.g., in FIG. 10E.

Referring to FIG. 10E, the ratchet piston 605 is in the first axial region 660. When the ratchet piston 605 is in the second axial region 670, the actuating bar 505 is laterally constrained by the opposed alignment elements 160a, 160b such that the alignment element 160a is slidable along the recessed surface 554 of the first axial member 550 of the actuating bar 505, and the alignment element 160b is slidable along the outward surface 562 of the second axial member 560 of the actuating bar 505. The recessed surface 554 and the outward surface 562 axially extend along lines parallel to each other as well as the guide slot 135 and the longitudinal axis a of the housing 105, the arrangement of the first set of teeth 570 of the actuating bar 505 and the second set of teeth 580 of the actuating bar 505.

As illustrated in FIG. 10E, the actuating bar 505 is in the second lateral position, such that the second set of teeth 580 of the actuating bar 505 are closer to the guide slot 135 than the first set of teeth 570 of the actuating bar 505. In this position, the second set of teeth 580 are in engagement with the corresponding teeth 482 of the second ratcheting element 480 of the carriage 405. Since the outward surface 562 and the recessed surface 554 have a length that corresponds at least approximately to the length of the first second region 670 of the ratchet piston 605, the reciprocation of the ratchet piston 605 between proximal and distal positions within the second axial region 670 causes the actuating bar 505 to also reciprocate between corresponding proximal and axial positions while remaining in the first lateral position. Thus, the ratcheting engagement between the second set of teeth 580 (which are disposed along the second axial member 560) and the second ratcheting element 480 is maintained during the reciprocation of the ratchet piston 605 and the actuating bar 505 when the ratchet piston 505 is within its first axial region 660. Thus, the proximal movement of the carriage 405 is effected by the reciprocation of the ratchet piston 605 between proximal and distal positions within the second axial range 670.

Although the device 5 is configured to move the carriage 405 distally when the actuating bar is in the first lateral position and to move the carriage 405 proximally when the actuating bar 505 is in the second lateral position, it should be understood that this orientation may be reversed and the selective engagement between the actuating bar 505 and the carriage 405 may be provided by other mechanism(s) in addition, or as an alternative, to the selective movement of the actuating bar 505 between the first and second lateral positions with respect to the housing 105.

Further, although the ratchet piston 605 actuates distal movement of the carriage 405 with respect to the housing when the piston 605 is actuated in the proximal first axial region 660, and actuates proximal movement of the carriage 405 with respect to the housing 105 when the piston 605 is actuated in the distal second axial region 660, it should be understood that the device 5 may be configured to distally advance the carriage 405 when the piston 605 is reciprocated in a distal axial region of its total available axial stroke and to proximally advance the carriage 405 when the piston 605 is reciprocated in a proximal region of its total available axial stroke. Moreover, it should be understood that the device 5 may be configured to allow the piston 605 to utilize the majority or entirety of its available axial stroke during its reciprocation to actuate the carriage 405 axially and/or distally. Further, other adjustment mechanisms for selecting the direction of rotation, in addition or as an alternative to the alignment projections 160a, 160b may be provided. For example, one or more dedicated actuators may be provided to select the engagement state of the reciprocating drive mechanism.

During a surgical procedure, the device 5 is positioned such that a portion of tissue is disposed between upper jaw, including the anvil 205 and the lower jaw, including the housing 105 and reload housing 905. Upon actuation of the anvil 205 about the anvil pivot pin 290 to the closed position illustrated in FIG. 4, the tissue is compressed to a thickness that allows for reliable staple driving and formation. For example, the gap between the anvil 205 and the opposed surface of the housing 5 and/or reload housing 905 may be 2 mm or less when the anvil 205 is in the closed orientation.

During a surgical procedure, after closure of the anvil 205 via the anvil piston 305, the carriage 405, which is in an initial proximal position, is distally advanced along the guide slot 135 via ratchet piston 605 as set forth above. As the carriage distally advances, a knife blade 450 linearly cuts tissue clamped between the anvil 205 and the housing 105, while the carriage distally pushes a wedge-shaped reload sled 950 in order to push staples from the reload housing 905 into the staple form plate 260 disposed in the guide channel 230. In this regard, the reload sled 950, in the example embodiment illustrated, includes four parallel staple-driving wedges 952 configured to drive, e.g., simultaneously, four respective staples into the staple form plate 260. The wedges 952 extend above a slide plate 954 configured to slide along the upper surface 132 of the lower wall 130 of the housing 105 in directions parallel to the longitudinal axis a of the housing 105 and the longitudinal path of the guide slot 135.

The cutting edge of the knife blade 450 preferably has an arc-shaped curvature as illustrated. The curvature may be beneficial, e.g., to maintain or center the leading edge of the tissue on the cutting edge or surface of the blade 450 as the blade is cutting the tissue. Although the knife blade 450 is curved, it should be understood than any desirable blade geometry or other cutting mechanism may be provided.

Although the reload housing 905 of the illustrated example is a replaceable cartridge separate from the reload sled 950, it should be understood that the reload sled 950 may be incorporated into the cartridge such that each cartridge assembly includes its own reload sled 950. Further although the reload sled 950 is configured to drive four staples using four wedges 952, it should be understood that the reload sled 950 may include any other number of wedges 952 or other staple driving elements configured to drive any desirable number of staples.

As the carriage 405 progresses distally from its initial proximal position, the first or upper jaw engagement portion 420 engages the anvil sled assembly 268. In particular, the flanges 422, 426 of the first jaw engagement portion 420 are received by anvil latch plate 270 such that the anvil latch plate 270 extends below both of the flanges 422, 426. At this stage, the carriage 405, along with the anvil sled assembly 268, are progressed distally along the guide slot 235 of the anvil 205. During this distal movement, the anvil 205 extends from the housing 105 through the guide slot 235, and into the guide channel 230. The anvil sled assembly 268 is supported by and axially slidable along the length of the guide channel 230 above the staple form plate 260 which extends along the guide channel 230. The form plate 260 has a guide slot 265 through which the carriage 405 also extends. In this regard, the flanges 422, 426 of the first jaw engagement portion 420 transfer force in the direction of the housing 105 into the anvil sled assembly 268. Since the staple push plate 260 is disposed between the anvil sled assembly 268 and the housing 105, the force is also transferred from the anvil sled assembly 268 to the staple push plate 260. Further, the low friction inserts 275 allow the carriage 405 to be slidable despite the force being transferred through the sliding surface between the anvil sled assembly 268 and the staple push plate 260. This reduced friction engagement may be particularly advantageous since the axial force is exerted by the actuating bar 505 at a location on the carriage 405 that is substantially offset from the sliding engagement between the anvil sled assembly 268 and the staple push plate 260.

Thus, the first jaw engagement portion 420 and second jaw engagement 430 engage the anvil 205 and housing 105 to provide a localized clamping force or reinforcement at the location of the cutting and stapling. This may be especially advantageous in that the forces tending to urge the jaws 205, 105 apart are increased by the pressing of staples into the staple form plate. In this regard the carriage, or force transfer bar, 405 has multiple functions, including, e.g., transferring force to engage and form staples, cut tissue, and maintain an anvil "clamp" position for constant tissue thickness. The slope of incline of jaws 105, 205 may be modified to increase the clamping effect as the force transfer bar 405 travels along the jaws 105, 205.

Although the knife blade 450 is configured to continuously cut the clamped tissue beginning at the proximal edge of the clamped tissue, it should be understood that the blade may be configured to engage the clamped tissue at a location distally beyond the proximal edge of the clamped tissue. For example, the blade 450 may be configured to swing or otherwise kick up into engagement with the tissue at a predetermined and/or selectable location along the clamped jaws. In this regard, the blade 450 may be initially disengaged from the anvil sled assembly 268, but after a predetermined and/or selectable distance and/or location during the distal movement swing up into engagement with the anvil sled assembly so as to begin cutting the tissue and allowing the transverse force to be transmitted from the carriage 405 to the staple anvil sled assembly 268. Other blade configurations may also be provided.

Once the carriage 405 has reached a desired axial position (for example, after the portion of tissue has been fully cut and stapled), the device 5 may retract the carriage 405 by moving the actuating bar 505 from its first lateral position to its second lateral position, as set forth above, and subsequent reciprocation of the ratchet jaw 605 in the second axial region 670 to ratchet the carriage 405 in the proximal direction with respect to the housing 105. As the carriage 405 moves proximally, the first jaw-engagement portion 410 may remain engaged with the anvil latch plate 270 of the anvil sled assembly, or the first jaw-engagement portion 420 may disengage the anvil latch plate, in which case the further proximal retraction of the carriage 405 causes the first jaw-engagement portion 420 to contact the proximal edge of the opening 282 of the return link 280 and thereby pull the anvil sled assembly 268 in the proximal direction.

When the device 5 is coupled to a shaft (e.g., the shaft 5205 described below) that houses the hydraulic tubes 705, a seal may formed between the shaft and the device 5 by crimping the wall of the shaft to the rear cap 805 with crimp ring 860, illustrated in FIG. 1.

FIGS. 14 to 21F illustrate a second exemplary surgical device 1005, FIGS. 22A to 38B illustrate a third exemplary surgical device 3005, and FIGS. 45 to 55 illustrate a fourth exemplary surgical device 8005. The device 1005 includes the features described herein with regard to the device 5, unless indicated otherwise. Further, the device 5 also includes the features of the device 1005 described herein, unless indicated otherwise. In this regard, like reference numbers indicate like or analogous elements, but with any reference numbers 1 to 999 of the device 5 corresponding to reference numbers 1001 to 1999, respectively, of the device 1005. For example, the housing 105 of the device 5 corresponds to the housing 1105 of the device 1005, the anvil 205 of the device 5 corresponds to the anvil 1205 of the device 1005, etc.

FIGS. 22A to 38B illustrate a third exemplary surgical device 3005. The device 3005 includes the features described herein with regard to the devices 5 and 1005, unless indicated otherwise. Further, the devices 5 and 1005 also include the features of the device 3005 described herein, unless indicated otherwise. In this regard, like reference numbers indicate like or analogous elements, but with any reference numbers 1 to 999 of the device 5 and any reference numbers 1001 to 1999 of the device 1005 corresponding to reference numbers 3001 to 3999, respectively, of the device 3005. For example, the housing 105 of the device 5 and the housing 1105 of the device 1005 each correspond to the housing 3105 of the device 3005, the anvil 205 of the device 5 and the anvil 1205 of the device 1005 each correspond to the anvil 3205 of the device 3005, etc.

FIGS. 45 to 55 illustrate a fourth exemplary surgical device 8005. The device 8005 includes the features described herein with regard to the devices 5, 1005, and 3005, unless indicated otherwise. Further, the devices 5, 1005, and 3005 also include the features of the device 8005 described herein, unless indicated otherwise. In this regard, like reference numbers indicate like or analogous elements, but with any reference numbers 1 to 999 of the device 5, and reference numbers 1001 to 1999 of the device 1005, and any reference numbers of the device 3001 to 3999 of the device 3005 corresponding to reference numbers 8001 to 8999, respectively, of the device 8005. For example, the housing 105 of the device 5, the housing 1105 of the device 1005, and the housing 3105 of the device 8005, each correspond to the housing 8105 of the device 8005, the anvil 205 of the device 5, the anvil 1205 of the device 1005, and the anvil 3205 of the device 3005 each correspond to the anvil 8205 of the device 8005, etc.

Further, to the extent that any differing features are indicated among the example devices 5, 1005, 3005, 8005, it should be understood that example embodiments of the present invention may include the differing features in combination or the alternative, and that the features may be provided in any desirable combination.

Figure 16:
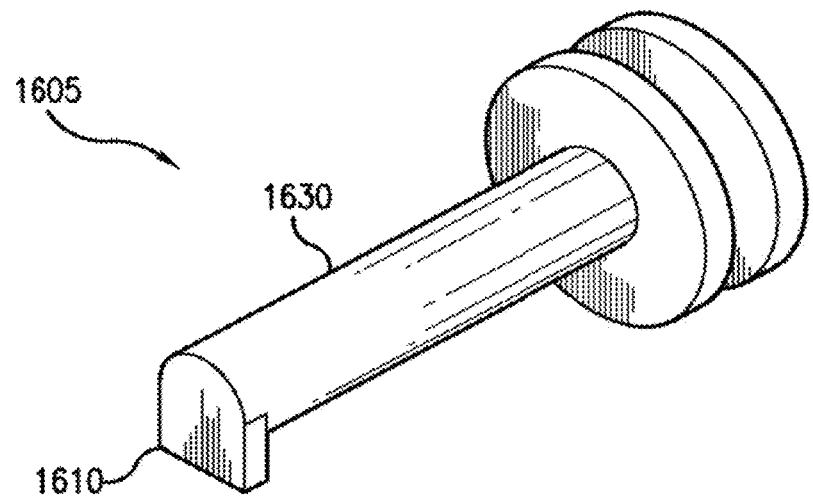
FIG. 16 shows a ratchet actuation piston of the device of FIG. 14.
Figure 17:
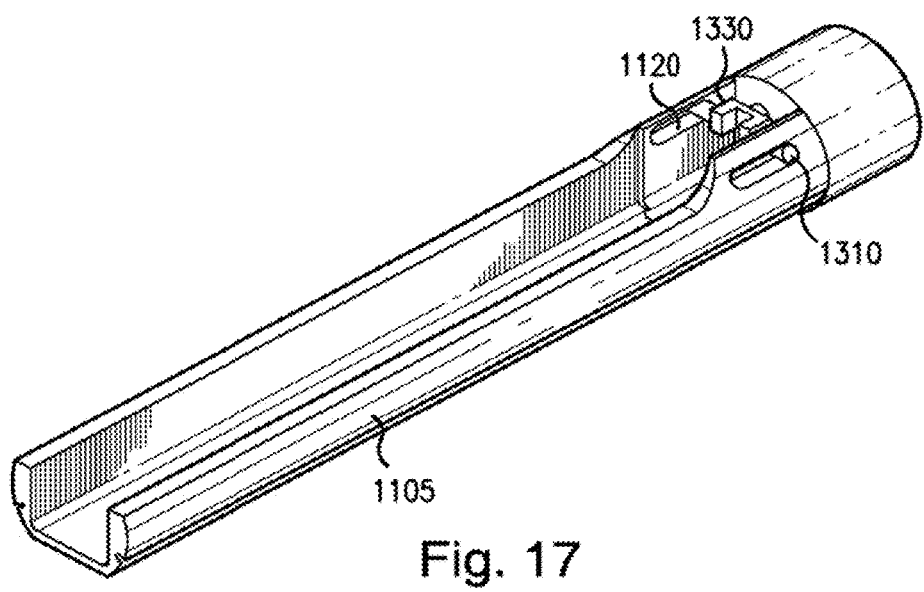
FIG. 17 shows the housing of the device of FIG. 14 with the anvil piston.
Figure 18:
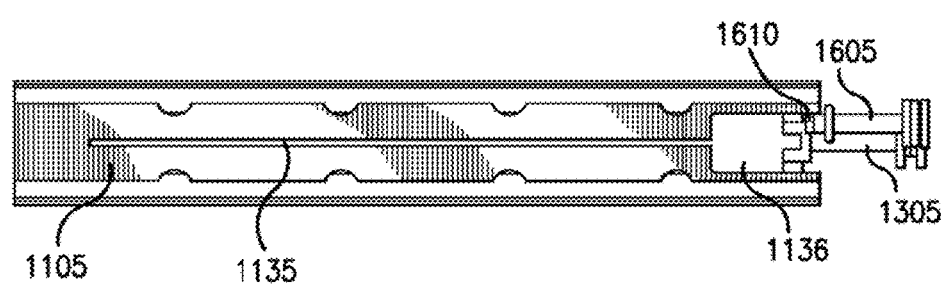
FIG. 18 is a bottom view of the housing of FIG. 14 with the anvil closure piston and the force transfer piston.
Figure 19A:
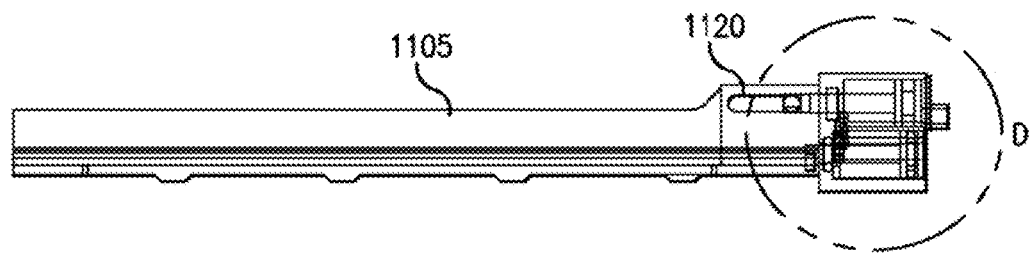
FIG. 19A is a side view of the housing assembly of the device of FIG. 14.
Figure 19B:
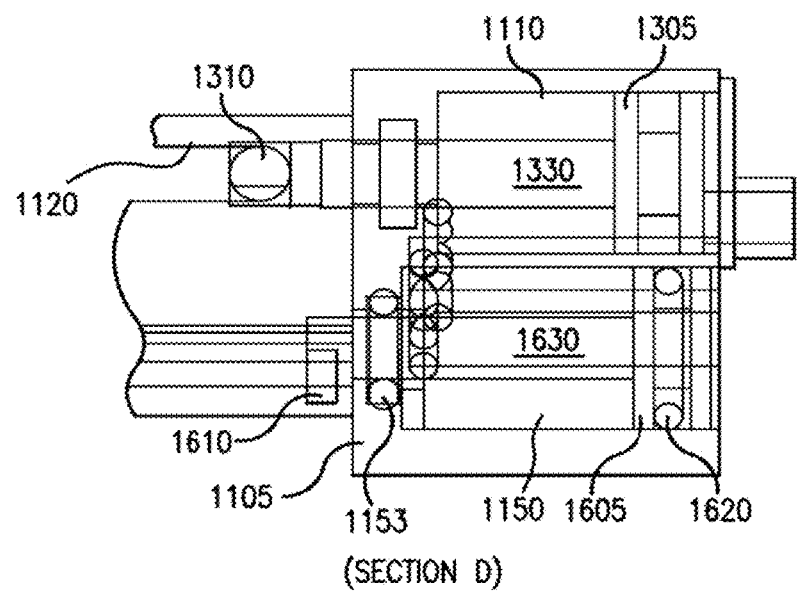
FIG. 19B is an enlarged view of section D of FIG. 19A.

Referring to FIG. 16, the ratchet piston 1605 of the device 1005 differs from the ratchet pistons 605, 3605, and 8605 of the devices 5, 3005, and 8005 in that the actuating bar engagement mechanism is provided in the form of a plate-like extension 1610 projected downwardly from the shaft 1630 in an additional non-limiting embodiment, in contrast to the pin 610 of the ratchet piston 605 and the channeled distal portion of the shafts 3630, 8630 of the devices 3005, 8005, respectively, described in greater detail below. The extension 1610 engages and cooperates with the slot 1510 of the actuating bar 1505 in the same manner the pin 310 engages the slot 310 of the device 5.

Figure 20A:
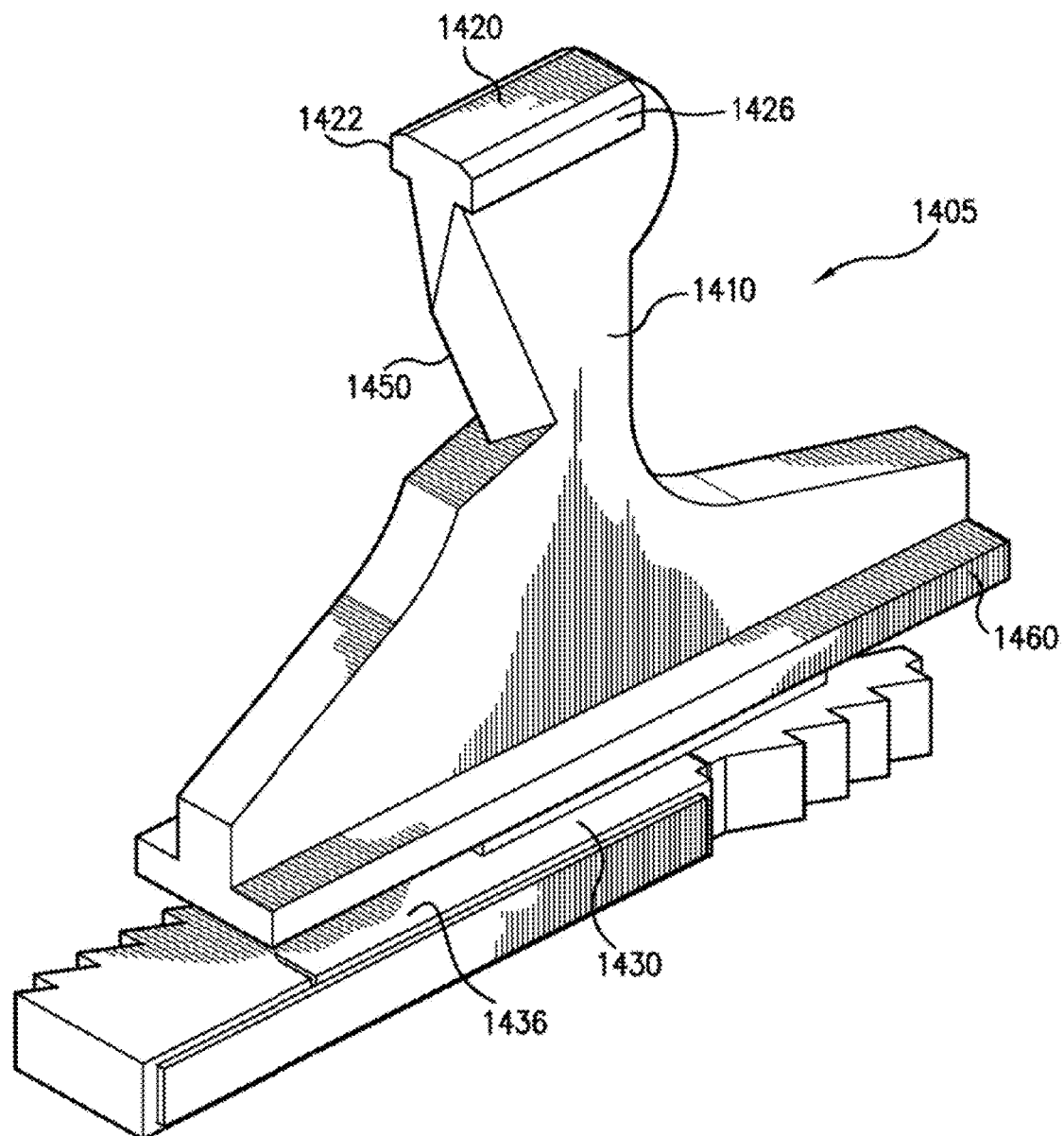
FIG. 20A shows a carriage of the device of FIG. 14.
Figure 20B:
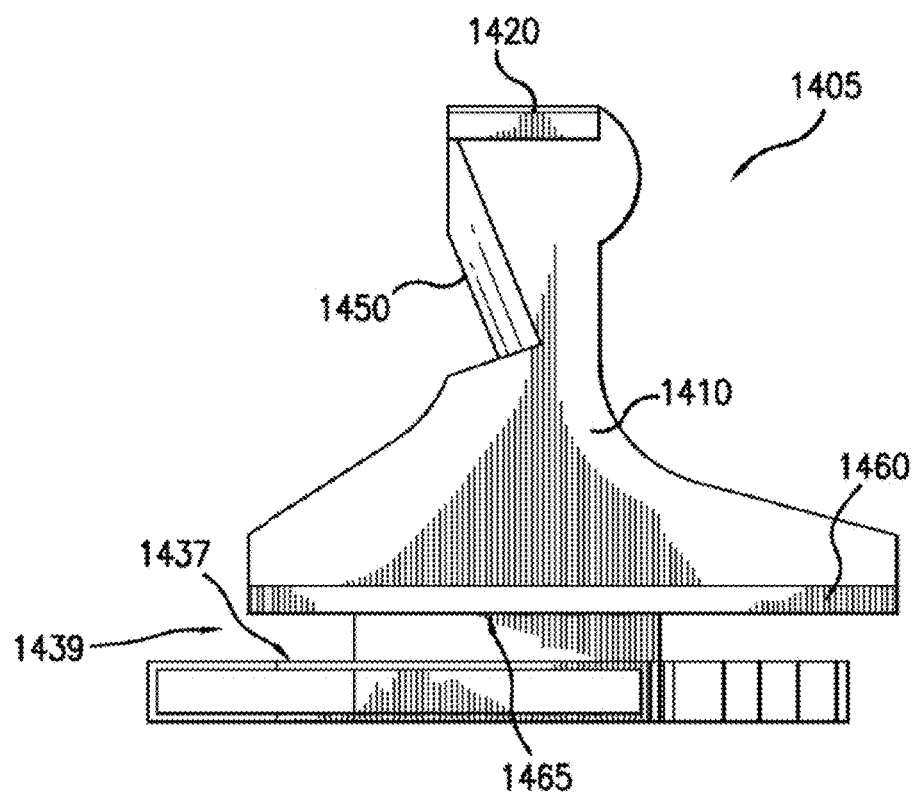
FIG. 20B is a side view of the carriage of the device of FIG. 14.
Figure 20C:
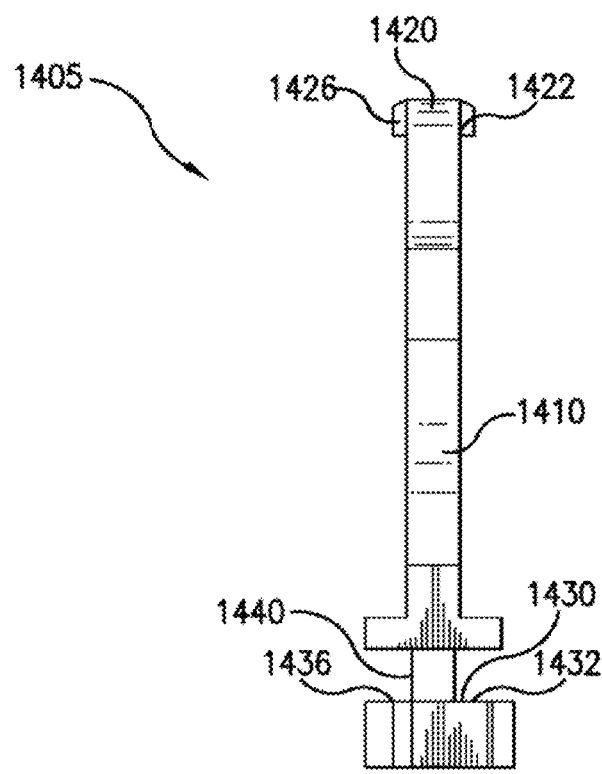
FIG. 20C is a rear view of the carriage of the device of FIG. 14.
Figure 20D:
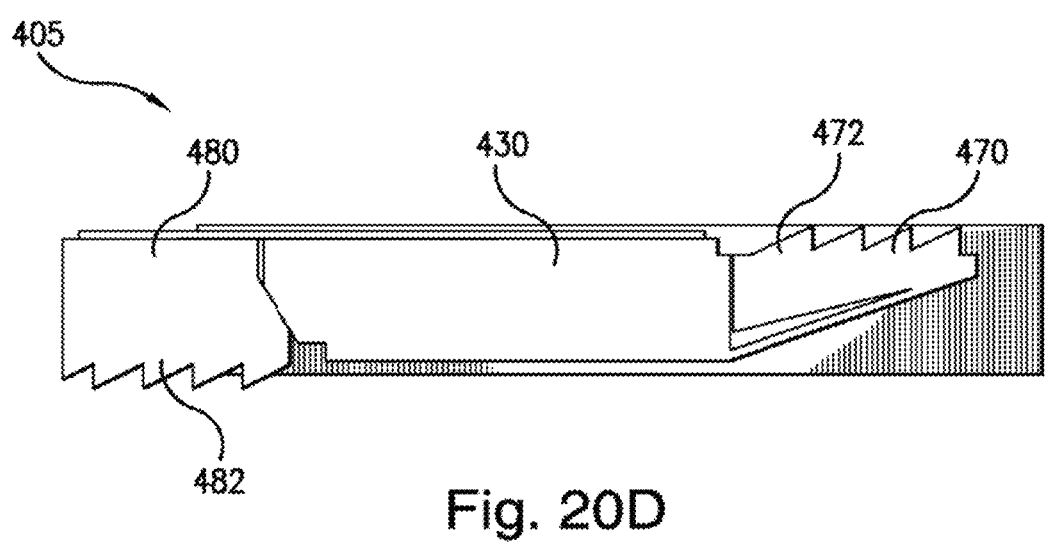
FIG. 20D is a bottom view of the carriage of the device of FIG. 14.

Referring to FIGS. 20A to 20C the carriage 1405 of the device 1005 differs from the carriages 405, 3405 of the devices 5 and 3005 in that the blade 3450 is linear and angled toward the distal end of the device 1005 as the blade progresses toward the anvil 1205 in an a additional non-limiting embodiment. The anvil 1405 also differs in that the carriage 3405 is integrally formed as a single monolithic piece with the retainer plate 1460, as opposed to having a retainer plate 460, 1460 as a separate and/or removable component.

Figure 21A:
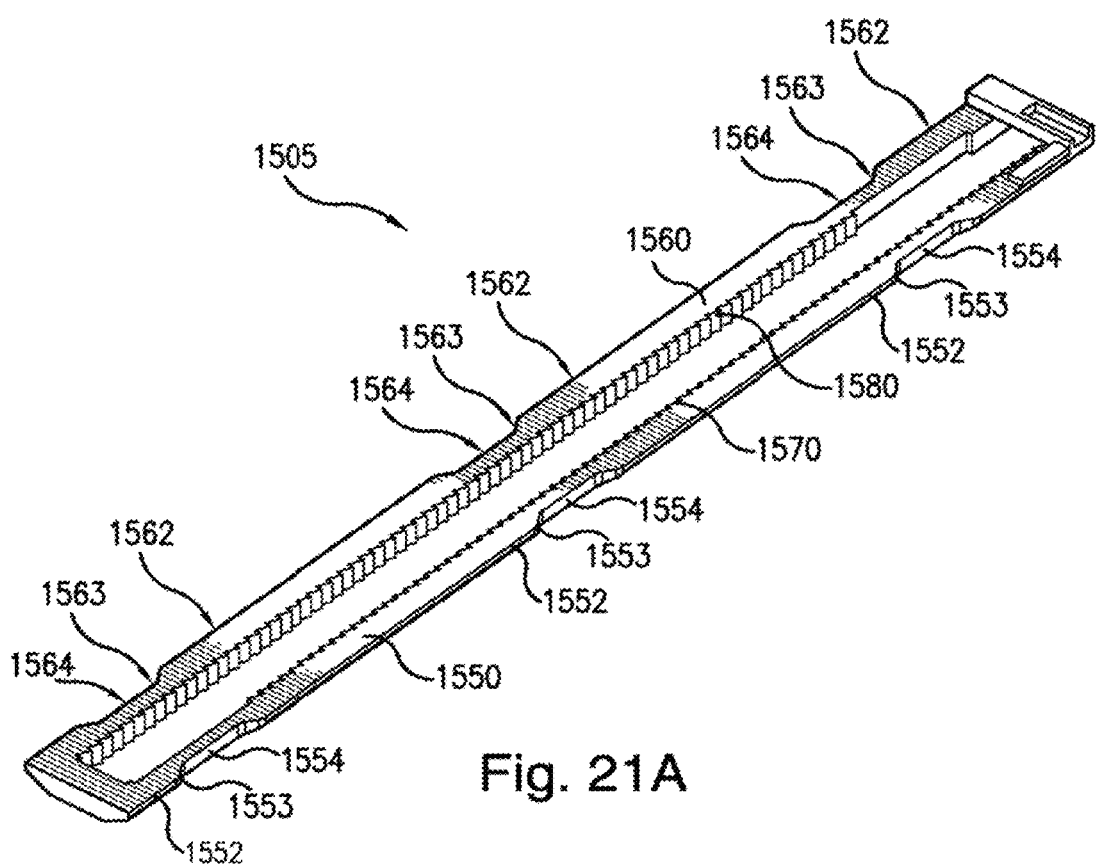
FIG. 21A shows a perspective view of a actuating bar of the device of FIG. 14.
Figures 21B, 21C:
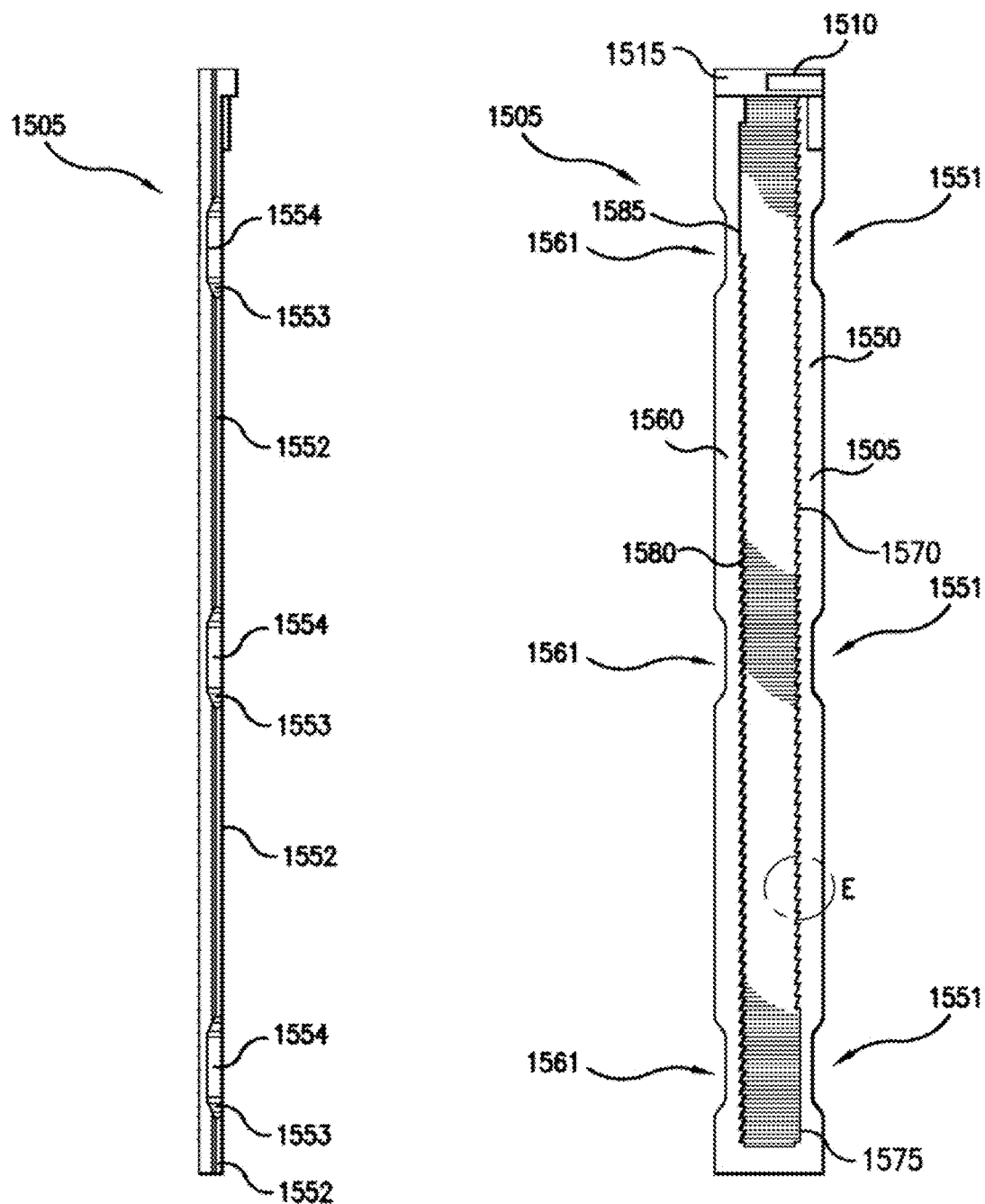
FIG. 21B is a side view of the actuating bar of the device of FIG. 14.
FIG. 21C is a top view of the actuating bar of the device of FIG. 14.
Figure 21D:
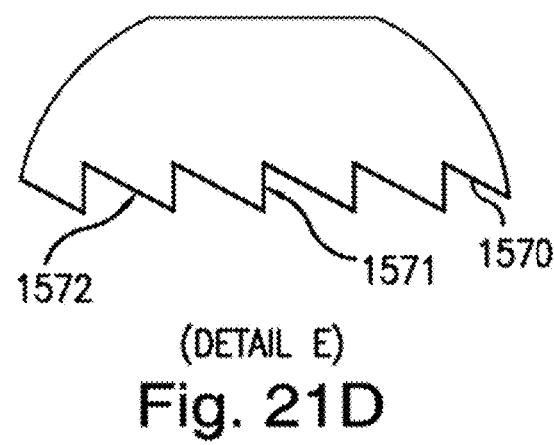
FIG. 21D is an enlarged sectional view corresponding to section E of FIG. 37.

Referring to FIGS. 21A to 21C the actuating bar 1505 of the device 1005 differs from the actuating bars 505, 3505, and 8505 of devices 5, 3005, and 8005 in that the force transfer slot 1510 to receive the extension 1610 is rectangular in cross section when viewed from the top as in FIG. 21C and is open at one of the lateral sides of the actuating bar 1505 in an additional non-limiting embodiment.

The actuating bar 505 of the device 5 also differs from the actuating bars 1505 and 3505 of the devices 1005 and 3005 in that the axial recesses 1551, 1561 are axially aligned, in an additional non-limiting embodiment. In this regard, a mechanism analogous to the mechanism illustrated in FIGS. 10C to 10E with respect to the device 5 is provided, but with the alignment projections of the device 1005 being offset by the same amount that the alignment recesses 551, 561 of the opposed pair of the actuating bar 505 of the device 5. It should be further understood that an additional analogous mechanism may be provided where both the opposed alignment projections are axially offset and the opposed alignment recesses 551, 561 are offset.

Referring to FIG. 21, each tooth 1570 has a latching surface 1571 having a steeper slope with respect to the lengthwise extension of the actuating bar 1505 than a ramped surface 1572. The ramped surface 1572 allows the first ratcheting element 1470 to be pushed laterally (via flexure of spring arm 1475) to allow the actuating bar 1505 to proximally move with respect to the first ratcheting element 1470 during the proximal strokes of the reciprocation of the ratchet piston 1605. During the distal stroke of the ratchet piston 605, the steeper (in this case perpendicular) latching surfaces 1571 engage the first ratcheting element 1470 to distally translate the carriage 1405. It is noted in this regard that the carriage 1405 may be held in its axial position during the proximal stroke via frictional forces due to engagement between the carriage 1405 and the other elements of the device 1005. The teeth 1580 on the opposed side of the actuating bar 1505 are reversed to allow an analogous reversed engagement to move the carriage 405 proximally with respect to the housing 105.

The ratcheting elements 1470 and 1480 have teeth ratcheting teeth 1472, 1482 with a profile analogous to the profile of teeth 1570 illustrated in FIG. 21 such that the latching surfaces of the teeth 1472, 1482 contact respective latching surfaces of the teeth 1570, 1580 when the actuating bar is moving the carriage 1405 in respective axial directions, and the ramped surfaces of the teeth 1472, 1482 engage and translate with respect to the respective ramped surfaces of the teeth 1570, 1580 during secondary piston strokes. However, any other arrangement may be provided, including providing the ratcheting elements 1470 and/or 1480 with differing tooth geometries and/or a different number of teeth 1472, 1482 than illustrated, including, e.g., a single tooth 1472, 1482.

Referring to FIG. 21C, it is further noted that series of teeth 1570 stops before reaching the distal end of the first axial element 1550 and the second set of teeth 1580 stops before reaching the proximal end of the second axial element 1560, which results in a distal flat 1575 on the inwardly directed surface of the first axial member 1550 and a proximal flat 1585 on the opposed inwardly directed surface of the second axial member 1560. In this regard, the flats 1575, 1585 are provided in respective axial regions where there the first and second ratcheting elements 470, 480, respectively, do not extend when the carriage 1405 is moved between its proximal-most and distal-most positions within the housing 1105. However, it should be understood that any desired pattern of teeth may be provided.

Figure 21E:
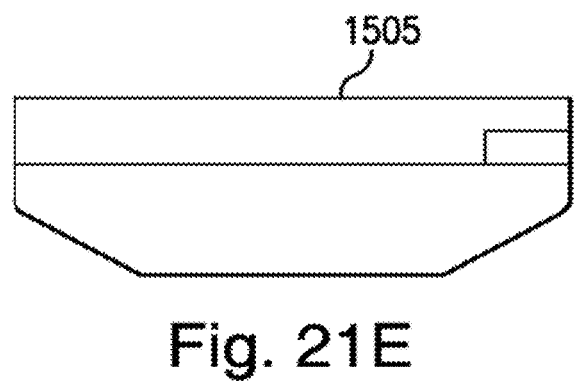
FIG. 21E is a back view of the actuating bar of the device of FIG. 14.
Figure 21F:
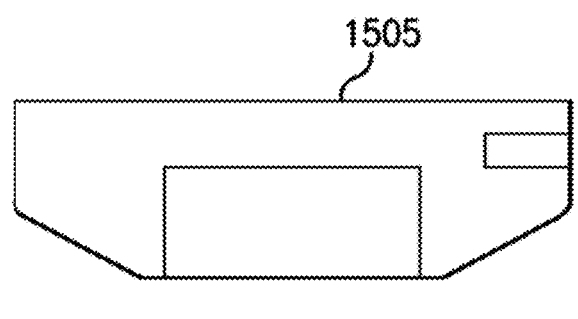
FIG. 21F is a front view of the actuating bar of the device of FIG. 14.

Referring to FIGS. 21E and 21 F, the bottom portion of the actuating bar 1505 has chamfered lower edges when viewed axially. However, it should be understood that any desired geometry may be provided.

Figure 22A:
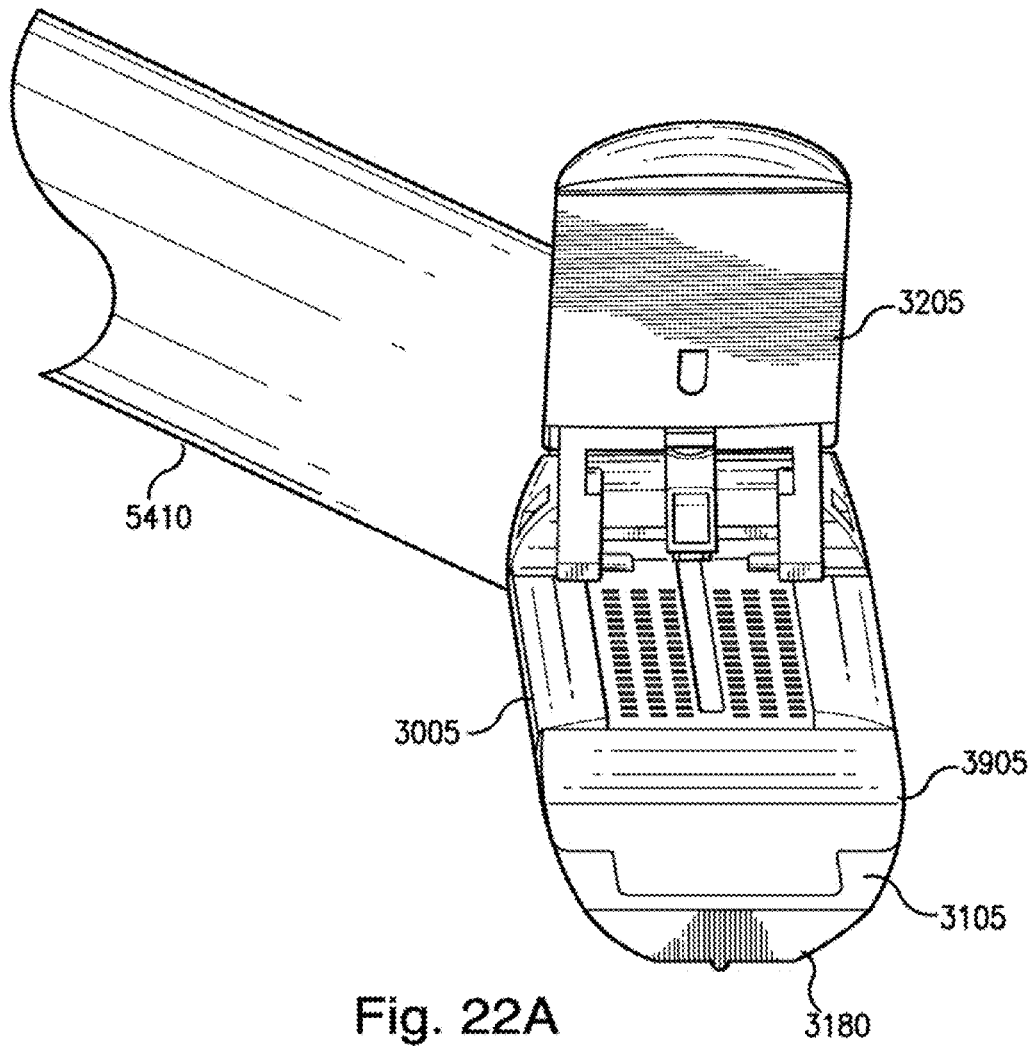
FIG. 22A shows a surgical device according to an example embodiment of the present invention.
Figure 22B:
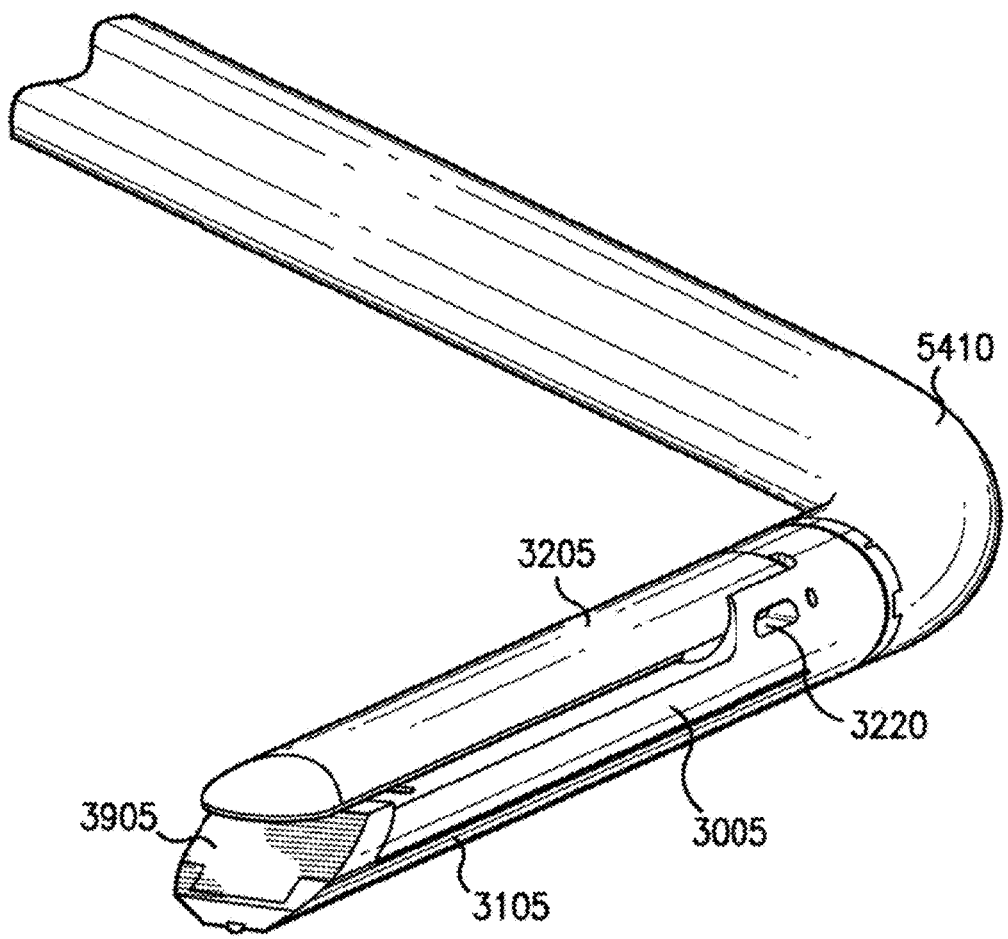
FIG. 22B shows a perspective view of the surgical device of FIG. 22A.

Referring to FIGS. 22A and 22B, the surgical device 3005 is coupled to a shaft 5410 to form a surgical system. Although the shaft 5410 is a flexible shaft, it should be understood that a rigid shaft may be provided. The shaft 5410 houses the hydraulic supply tubes 3705a, 3705b, 3705c, and 3705d.

Figure 23:
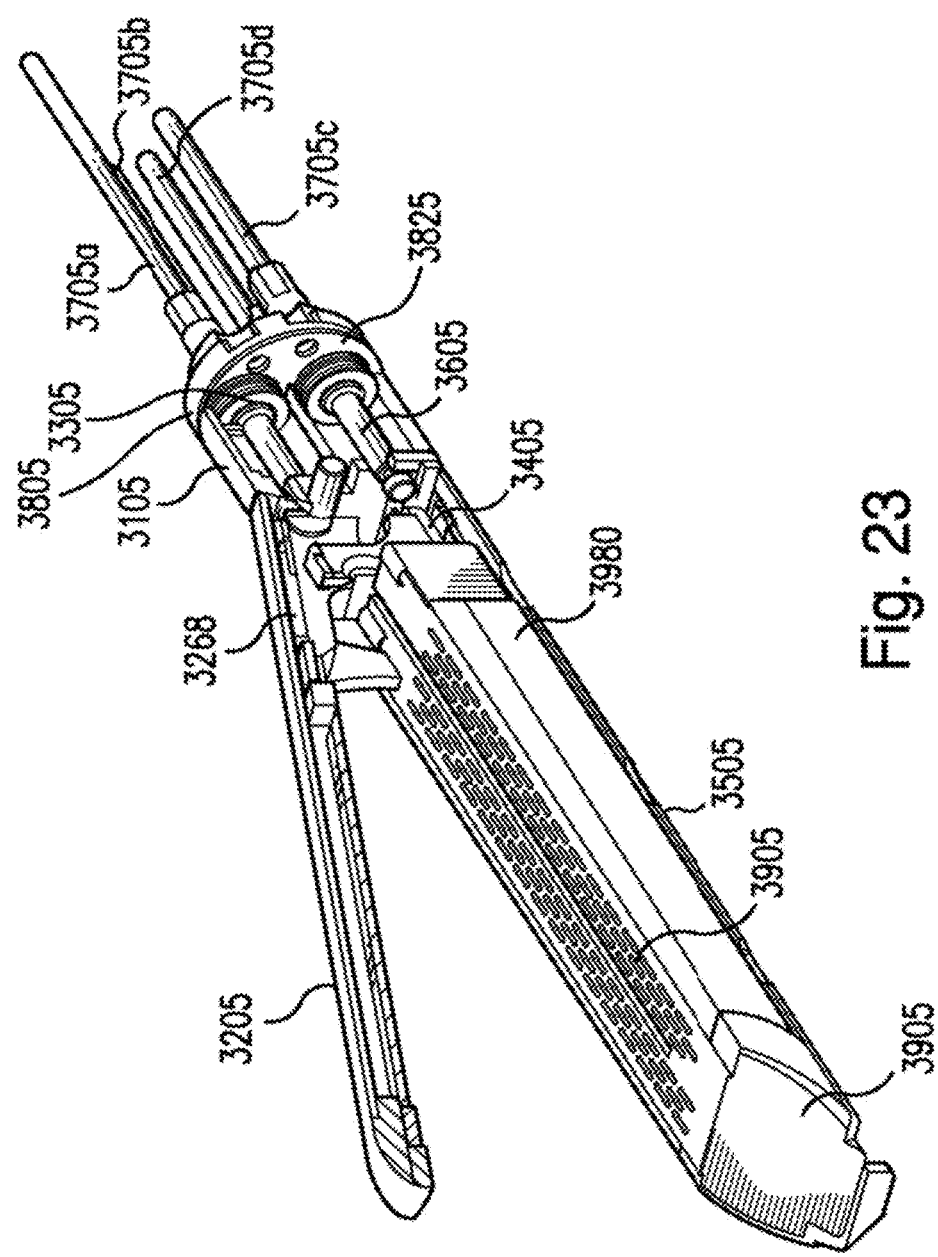
FIG. 23 is a cross-sectional view of the surgical device of FIG. 22A with the anvil piston and the anvil in their open positions.
Figure 24:
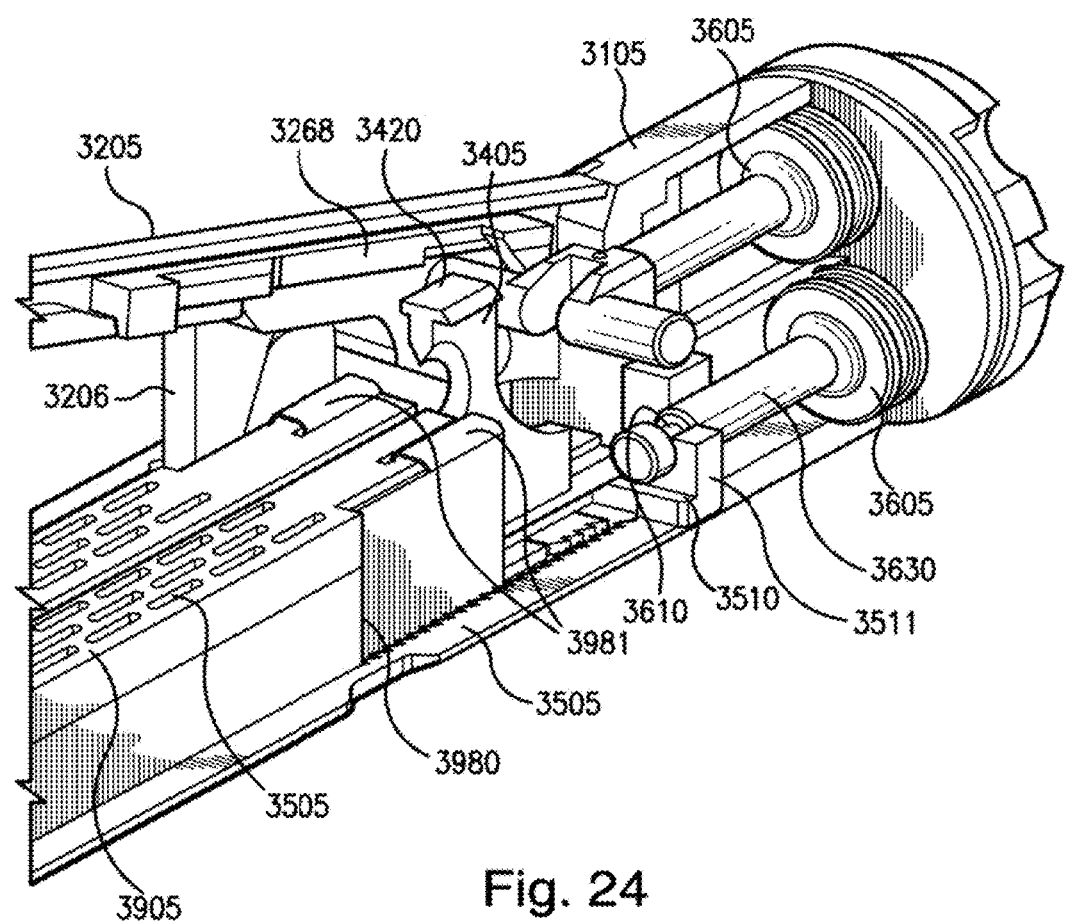
FIG. 24 is a partial cross-sectional view of the surgical device of FIG. 22A with the anvil piston and the anvil in their open positions.

Referring to FIGS. 23 and 24, the surgical device 3005 differs from the surgical devices 5, 1005, and 8005 in that the reload housing 3905, which functions as a staple cartridge, is received in a reload sleeve 3980 such that a proximal portion of the reload housing 3905 slides into and is radially constrained by retention flanges 3981 of the reload sleeve 3980, in an additional example embodiment. The reload sleeve 3980 may be removed from the housing when the reload housing 3905 is removed or the reload sleeve 3980 may be fixed with respect to the housing 3105 when the reload housing 3905 is removed.

Figure 25:
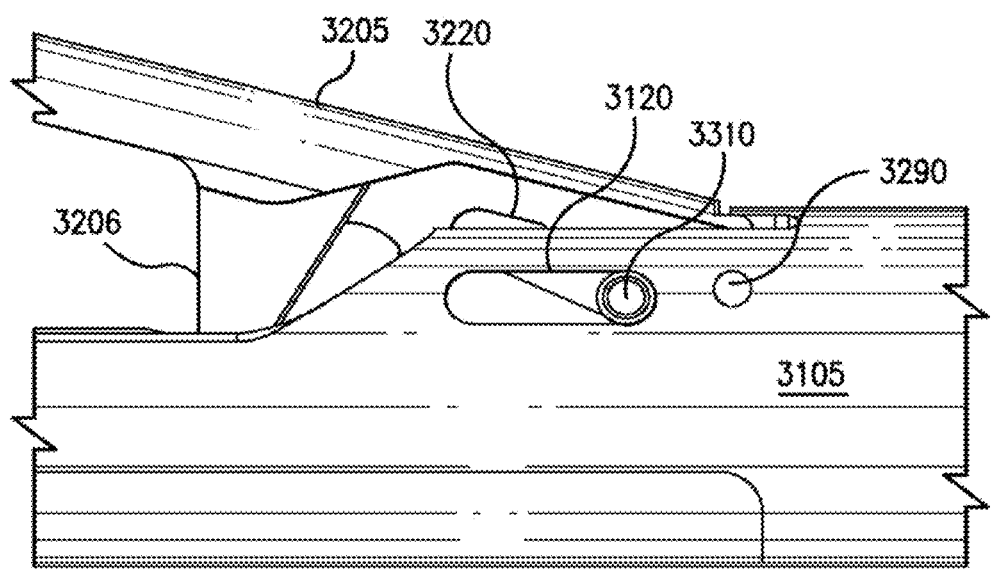
FIG. 25 is a partial side view of the device of FIG. 22A with the anvil in an open position.
Figure 26:
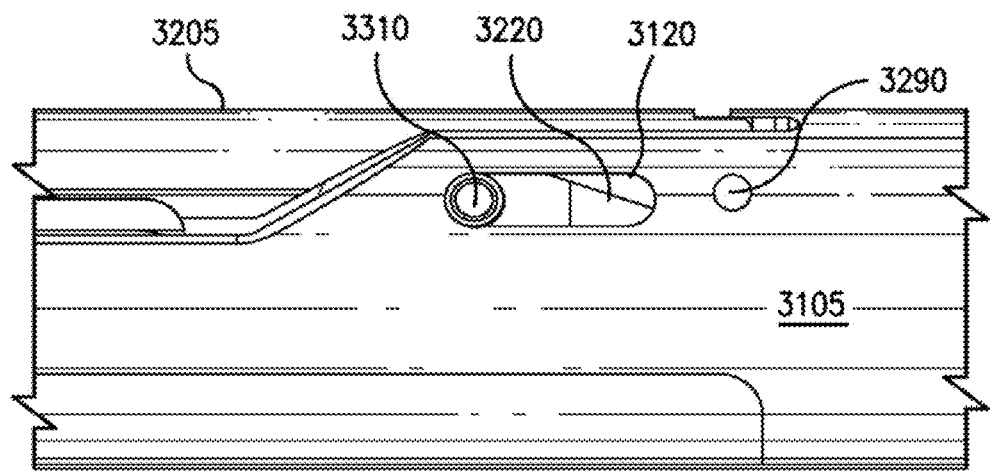
FIG. 26 is a partial side view of the device of FIG. 22A with the anvil in a closed position.
Figure 27:
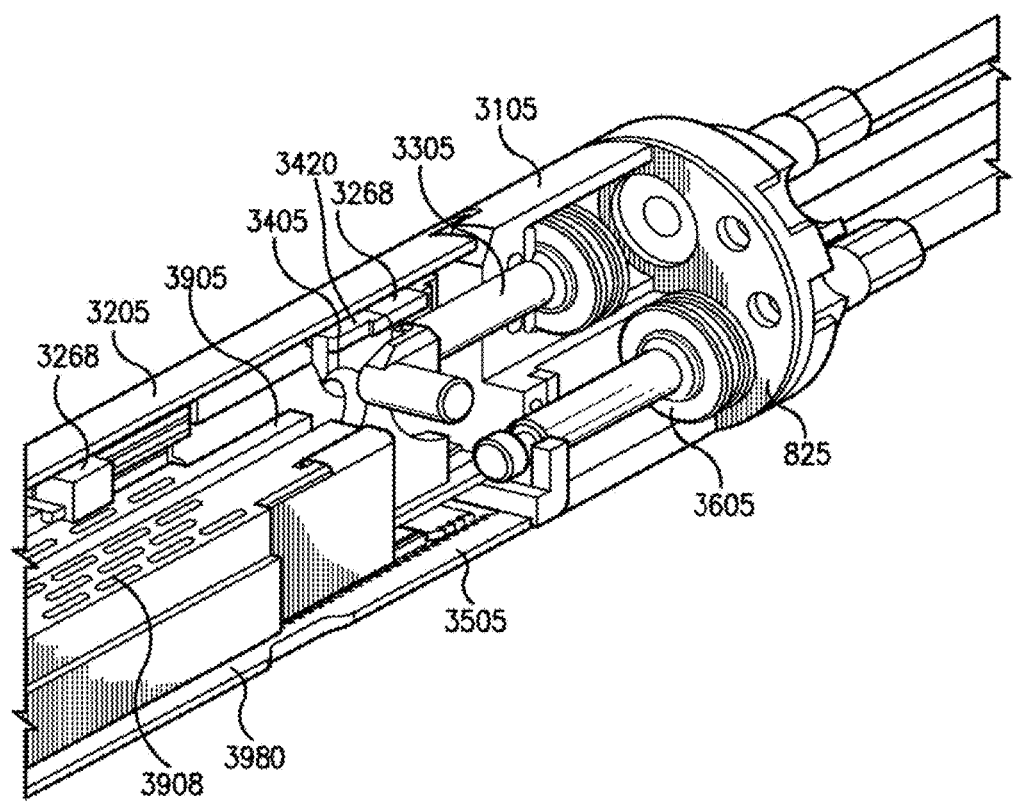
FIG. 27 is a partial cross-sectional view of the device of FIG. 22A with the anvil piston and the anvil in their closed positions.
Figure 28:
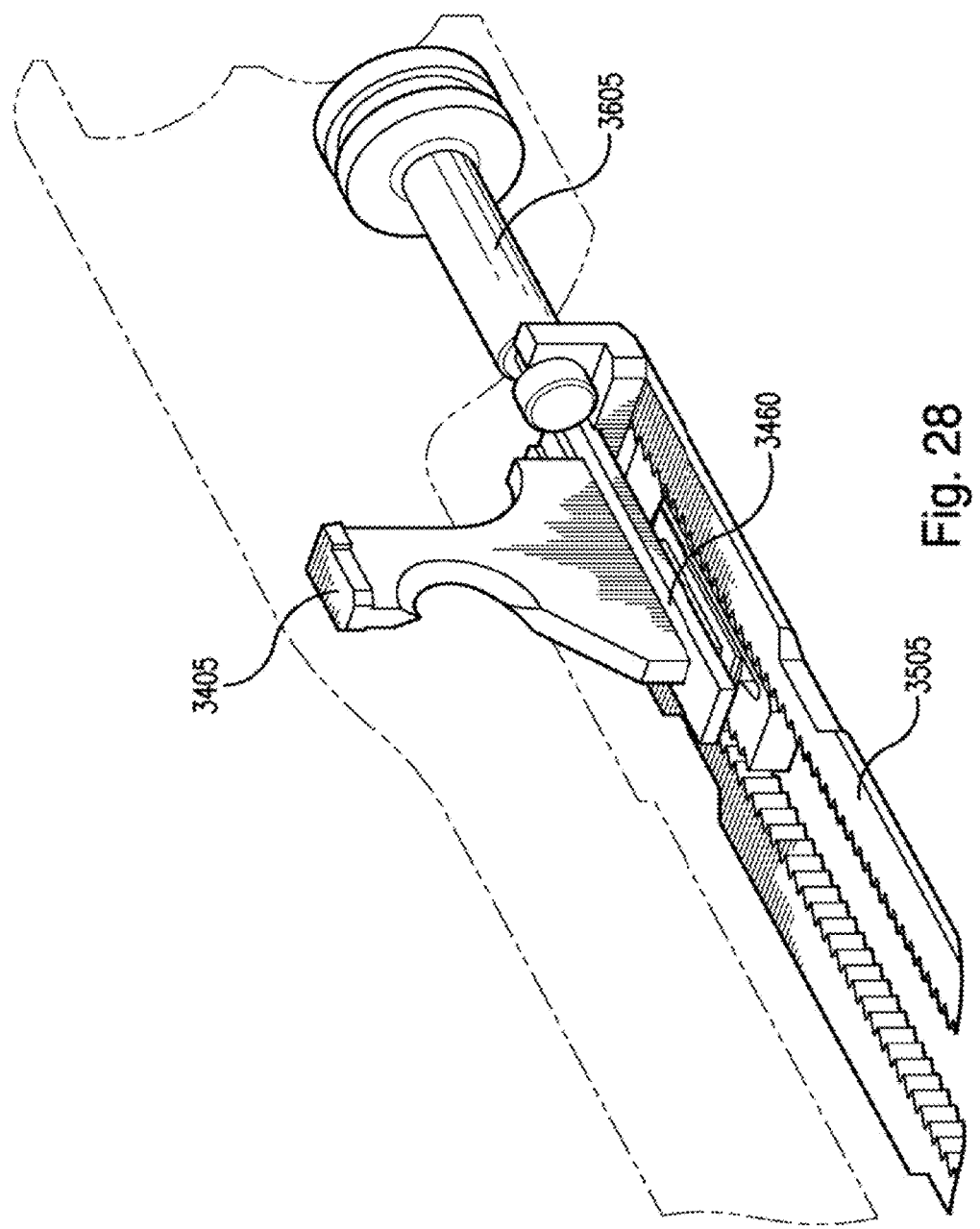
FIG. 28 is a partial view of the carriage and a carriage actuation assembly of the device of FIG. 22A.

Referring to FIGS. 25 and 26, the surgical device 3005 differs from the surgical devices 5, 1005, and 8005 in that the anvil actuation slot 3220 is nonlinear and includes a distal portion which extend parallel to the anvil pin slot 3120 of the housing 3105 when the anvil is in the closed position with respect to the housing, as illustrated in FIG. 26 in an additional example embodiment. This arrangement may reduce or eliminate any proximally directed forces exerted on the pins or shafts 3310 of the anvil piston 3305 when tissue is being clamped between the anvil 3205 and the housing 3105. The anvil 3205 also differs from the anvils 205, 1205, 8205 in that it includes a transverse member 3206 extending between a gap between respective clamping surfaces of the anvil 3205 and the housing 3105 and/or reload housing 3905, in the additional example embodiment. The transverse member 3206 acts to form a positive stop to maintain a proximal edge of the clamped tissue from extending proximally of the desired clamping region.

Further referring to FIG. 26, the drive pin 3310 has been moved forward, or distally, from the position of FIG. 25 in order to clamp the anvil 3205 down. In this regard, the clamping force, e.g., during the forward movement of the pin, is proportional to the fluid pressure applied to the piston 3305. As illustrated, e.g., in FIG. 27, the clamp piston 3305 extends due to fluid pressure in the cylinder 3110.

Figure 29:
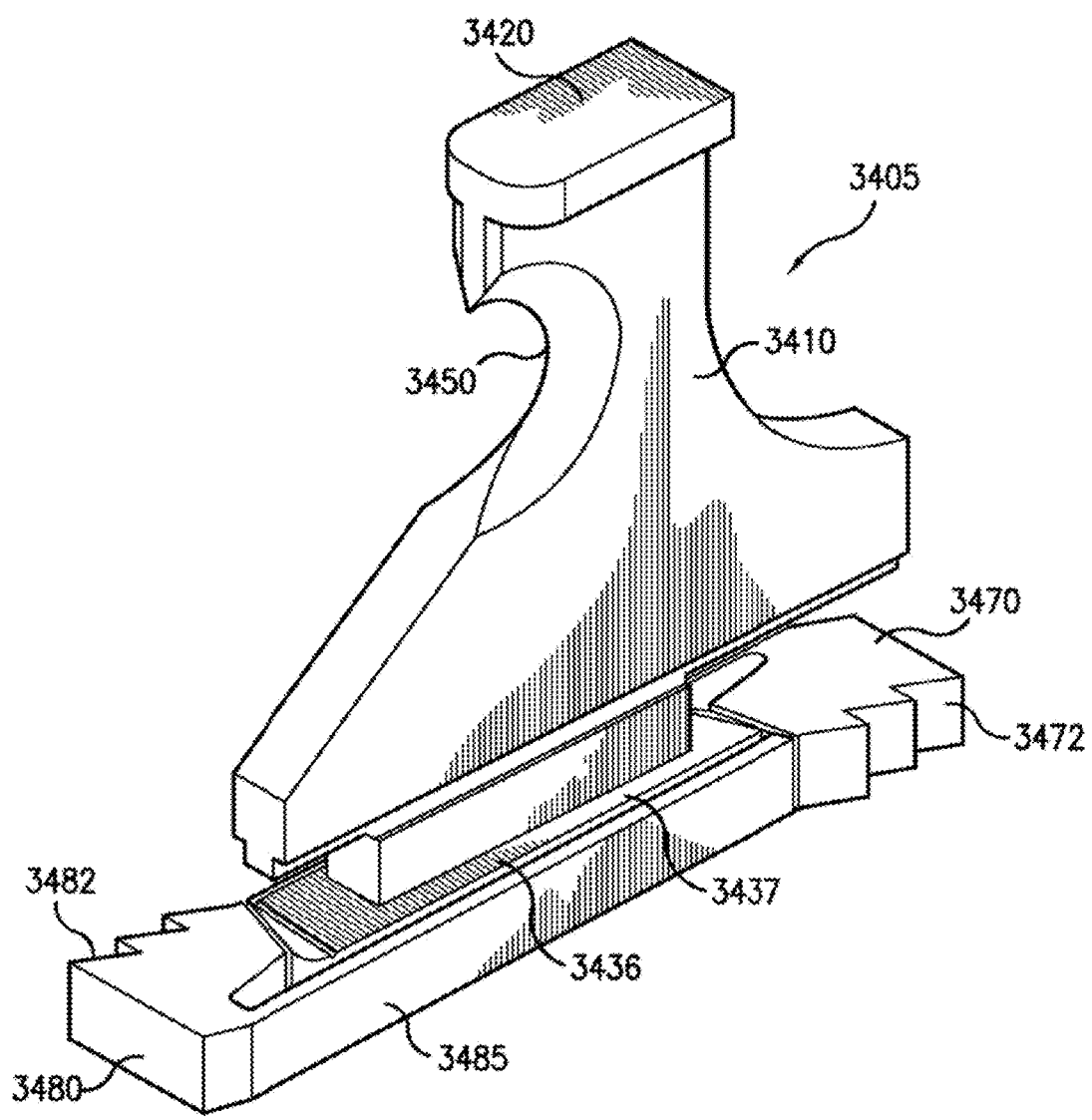
FIG. 29 shows the carriage of the device of FIG. 22A detached from the retainer plate.

FIG. 29 shows the carriage 3405 with the retainer plate 3460 removed. As with the other devices 5, 1005, 8005, the carriage, or force transfer bar, 3405 has multiple functions, including, e.g., transferring force to engage and form staples, cut tissue, and maintain an anvil "clamp" position for constant tissue thickness.

Figure 31A:
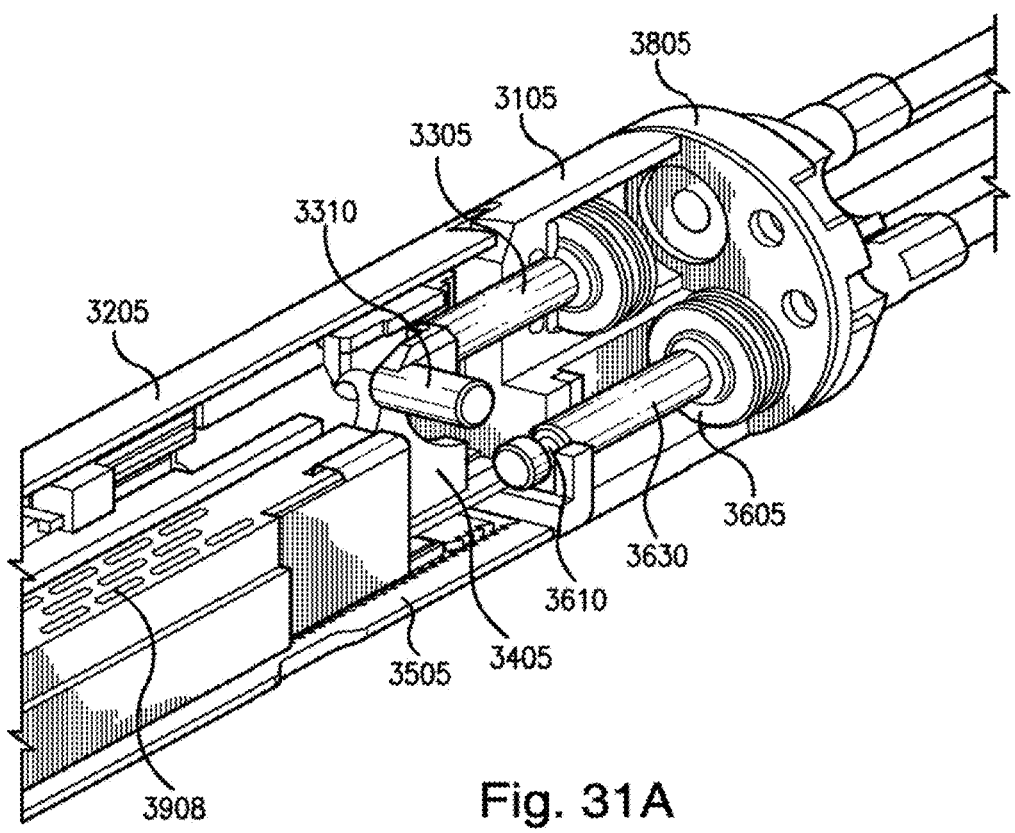
FIG. 31A is a partial cross-sectional view of the device of FIG. 22A with the anvil in a closed position and the ratchet actuation piston in a proximal position.
Figure 31B:
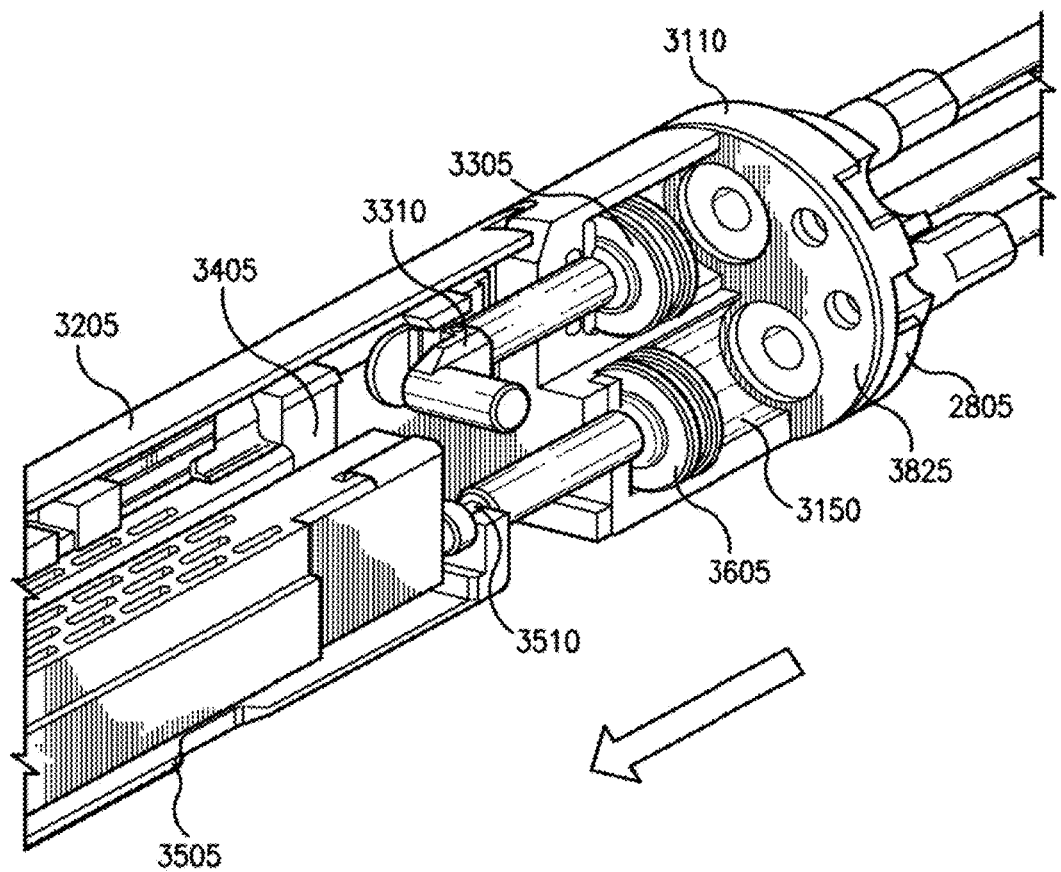
FIG. 31B is a partial cross-sectional view of the device of FIG. 22A with the anvil in a closed position and the ratchet actuation piston in a distal position.
Figure 31C:
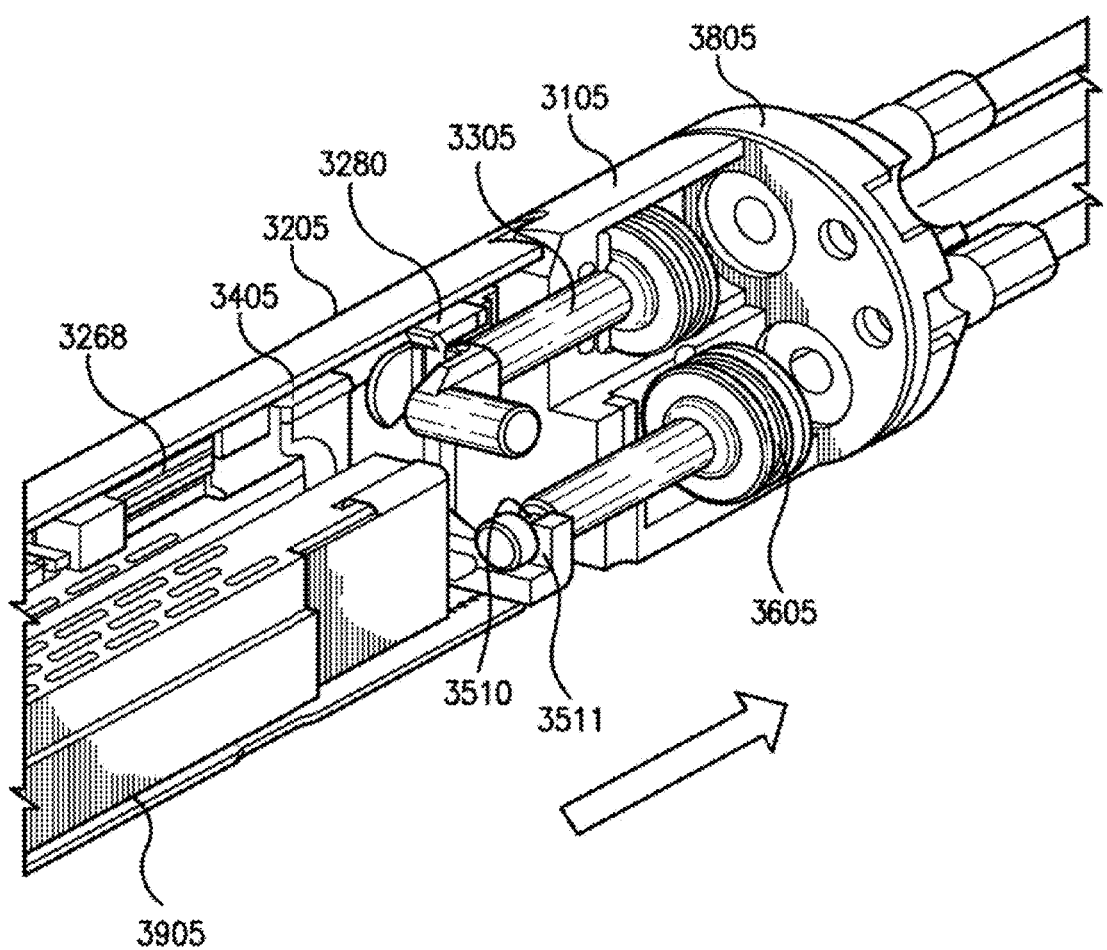
FIG. 31C is a partial cross-sectional view of the device of FIG. 22A with the anvil in a closed position and the ratchet actuation piston moving from a distal position to a proximal position.

FIG. 31B shows the piston 3605, actuator (reciprocating bar 3505), and carriage (force transfer bar) 3405 moving forward, or distally, as indicated by the direction of the arrow illustrated in FIG. 31B. FIG. 31C shows the piston 3605 moving backward, or proximally, as indicated by the direction of the arrow illustrated in FIG. 31C. The piston then continues to oscillate back and forth between the positions illustrated respectively in FIGS. 31B and 31C.

Figure 30:
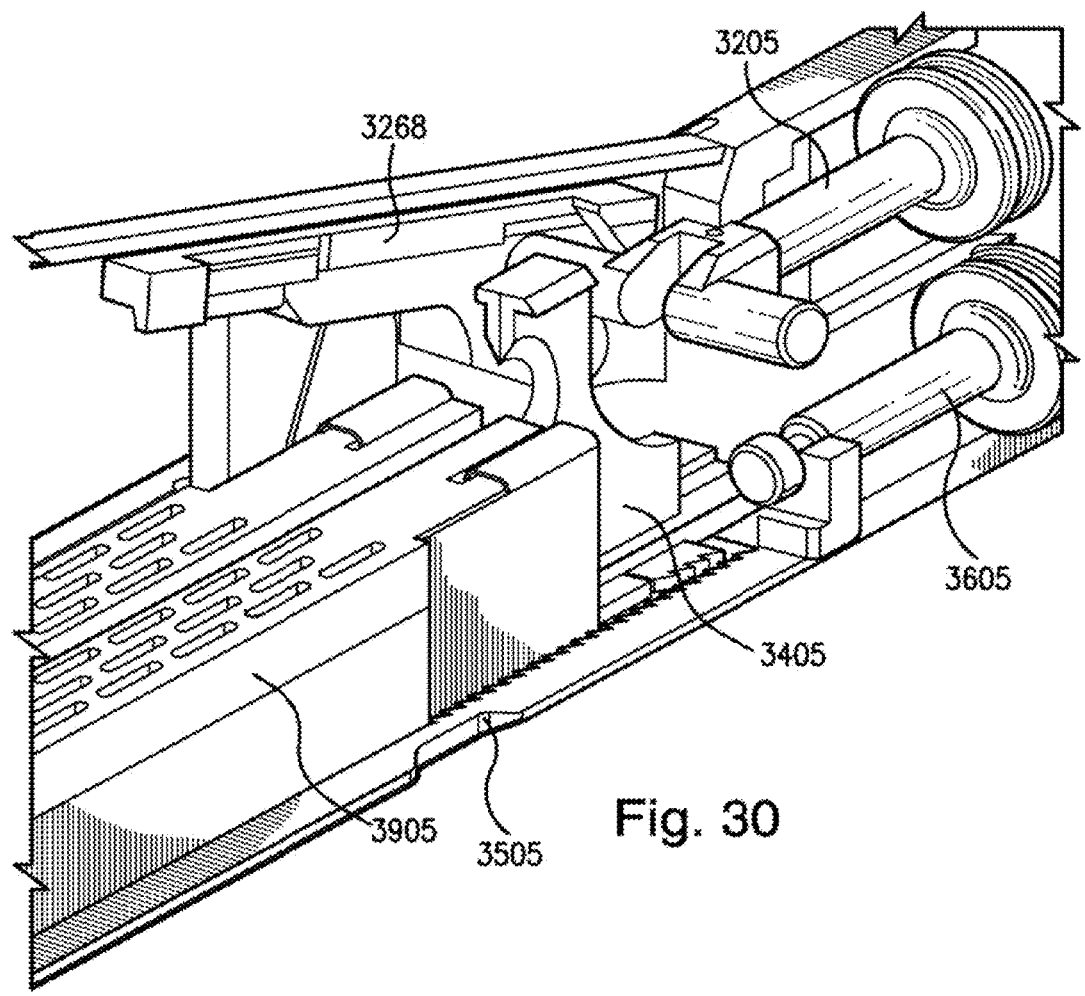
FIG. 30 is a partial cross-sectional view of the device of FIG. 22A with the anvil in an open position.
Figure 32:
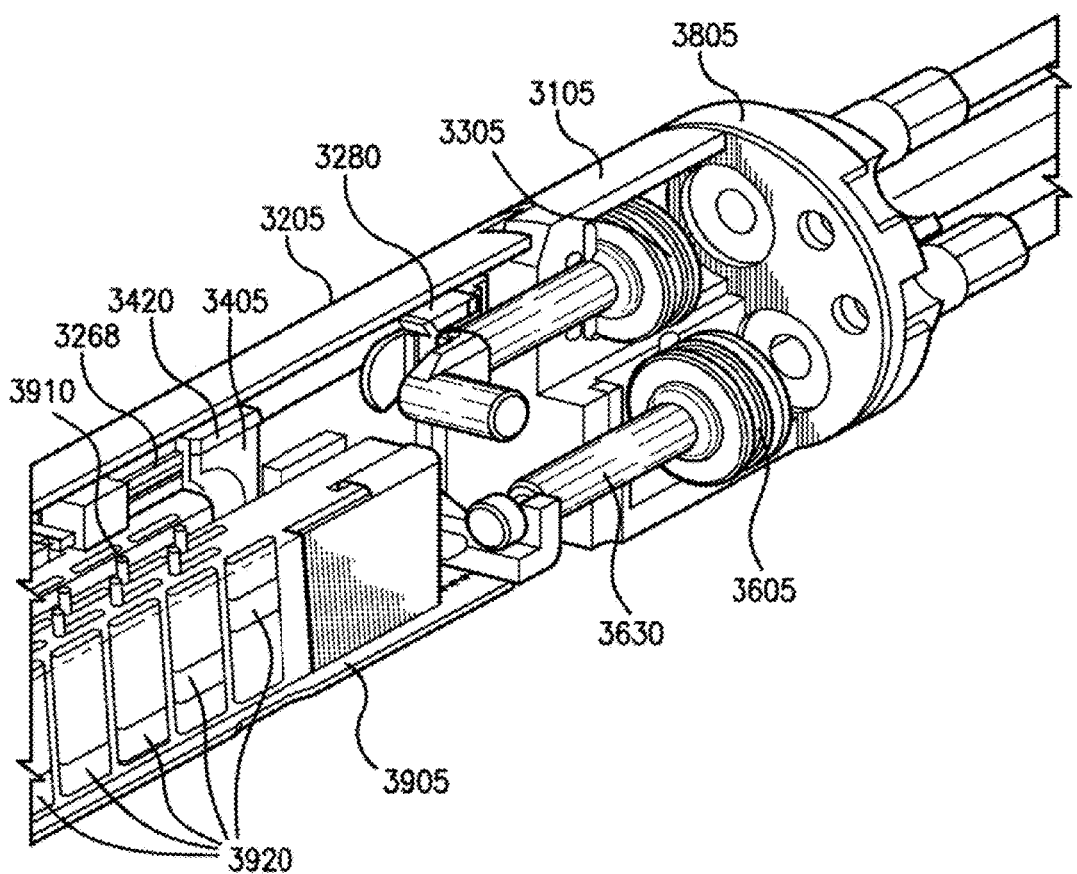
FIG. 32 is a partial cross-sectional view of the device of FIG. 22A with the anvil in a closed position and the ratchet actuation piston in a distal position and showing the driving of staples by the reload sled.

Referring, e.g., to FIGS. 30 to 32, the device 3005 also differs from the devices 5, 1005 in that the ratchet piston 3605 includes a circumferential recess 3610 at a distal end portion of the ratchet piston shaft 3630, instead of a pin 610 or projection 1610 as provided in the devices 5 and 1005, respectively, in an additional example embodiment.

Further, the actuating bar 3505 differs from the actuating bars 505 and 1505 of the devices 5 and 1005 in that it includes a force transfer rib 3510 in an additional example embodiment, instead of force transfer slots 510, 1510. The ratchet piston 3605 is configured to mate with the actuating bar 3505 in a manner analogous that set forth above with respect to ratchet pistons 605, 1605 and actuating bars 505, 1505 of devices 5 and 1005, except that instead of a projection or male member 610, 1610 of the ratchet piston 605, 1605 extending into a recess or female structure of the actuating bar 505, 1505, the ratchet piston 3605 includes a recess or female structure 3610 configured to receive a projection 3510 of the actuating bar 3505. The transversely extending force transfer rib 3510 of the actuating bar 3505 extends into the circumferential recess 3610 of the shaft 3630, thereby axially constraining the actuating bar 3505 with respect to the ratchet piston 3605, while allowing the rib 3510 to transversely slide with respect the recess 3610 during actuation of the actuating bar 3505 between its first and second lateral positions with respect to the housing 3105. The force transfer rib 3510 has an upward projection 3511 that also extends into the circumferential recess 3610 of the ratchet piston 3605 when the actuating bar 3505 is in its first lateral position. Thus, the extension of the projection 3511, in addition to the transversely extending portion of the rib 3510, into the circumferential recess 3610 allows for increased structural integrity at the point of force transfer between the ratchet piston 3605 and the actuating bar 3505 during the distal movement of the carriage 3405.

Figure 33:
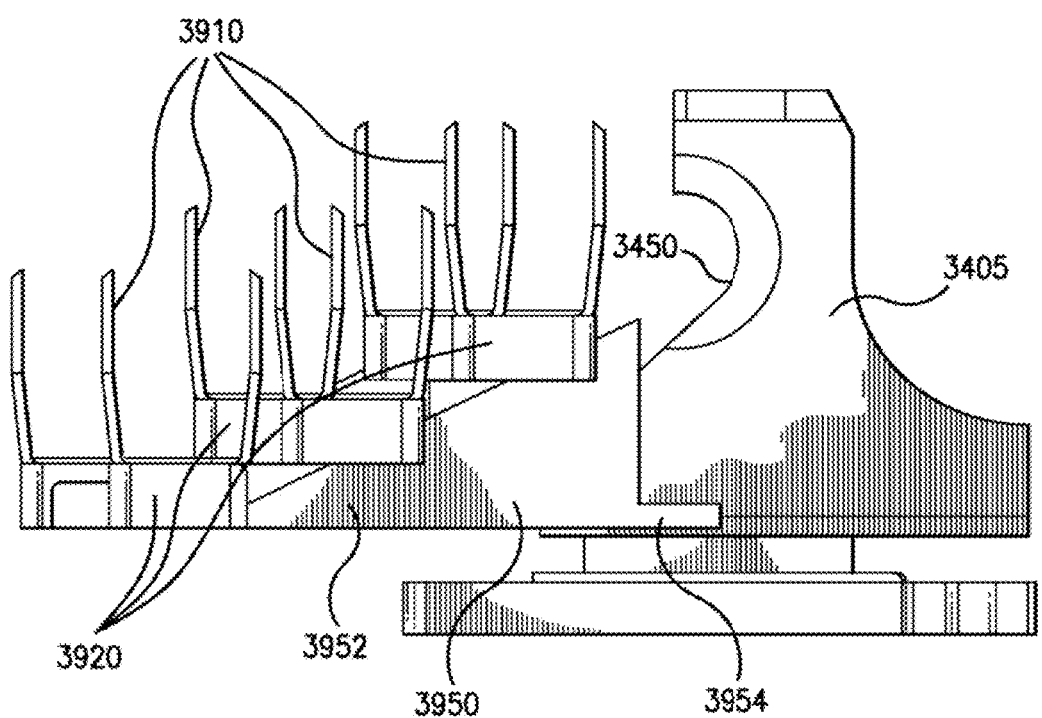
FIG. 33 shows the engagement of the reload sled of the device of FIG. 32A with staples of the reload housing.
Figure 34:
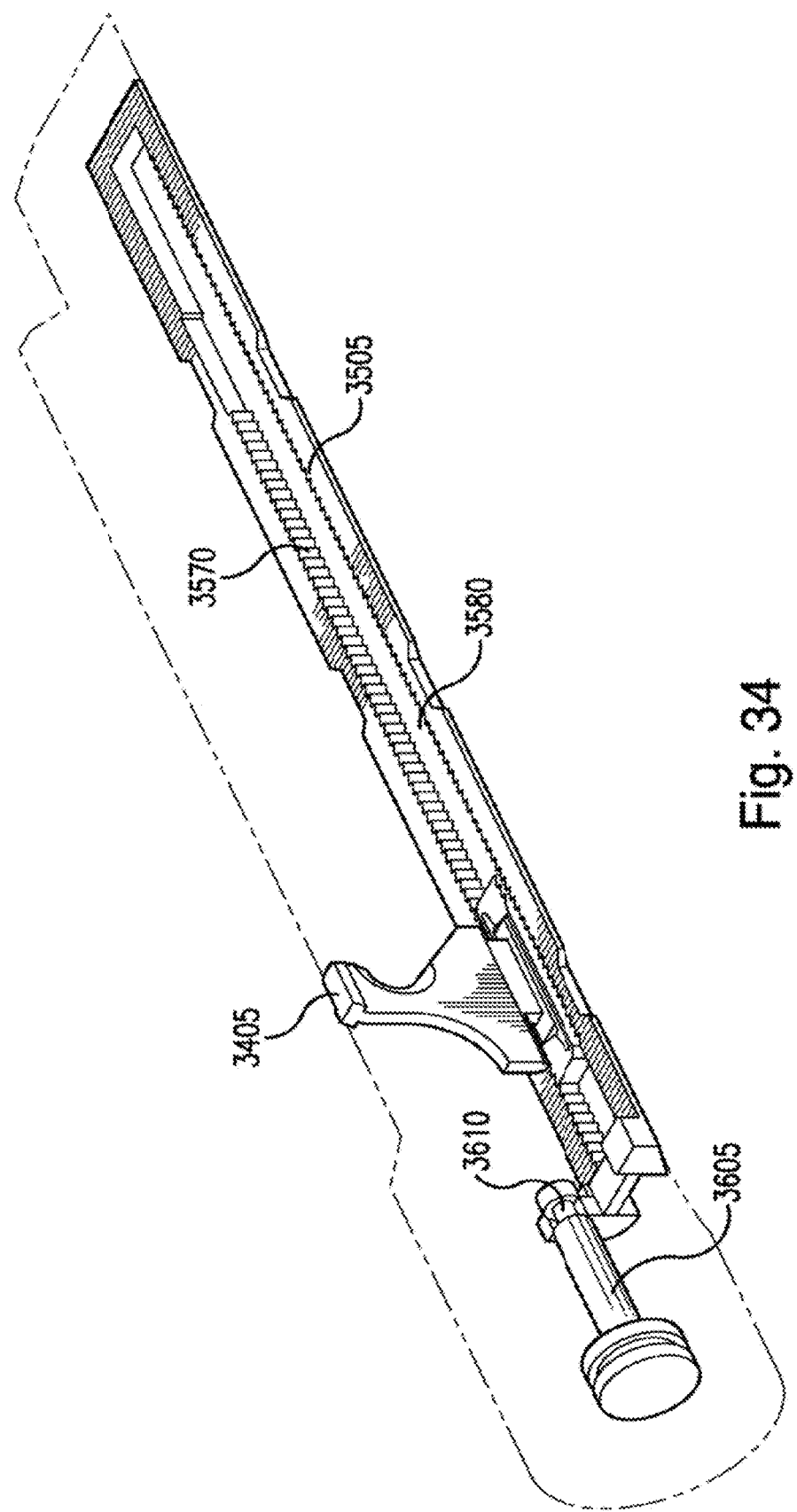
FIG. 34 shows a carriage and actuation assembly of the device of FIG. 32A.
Figure 35A:
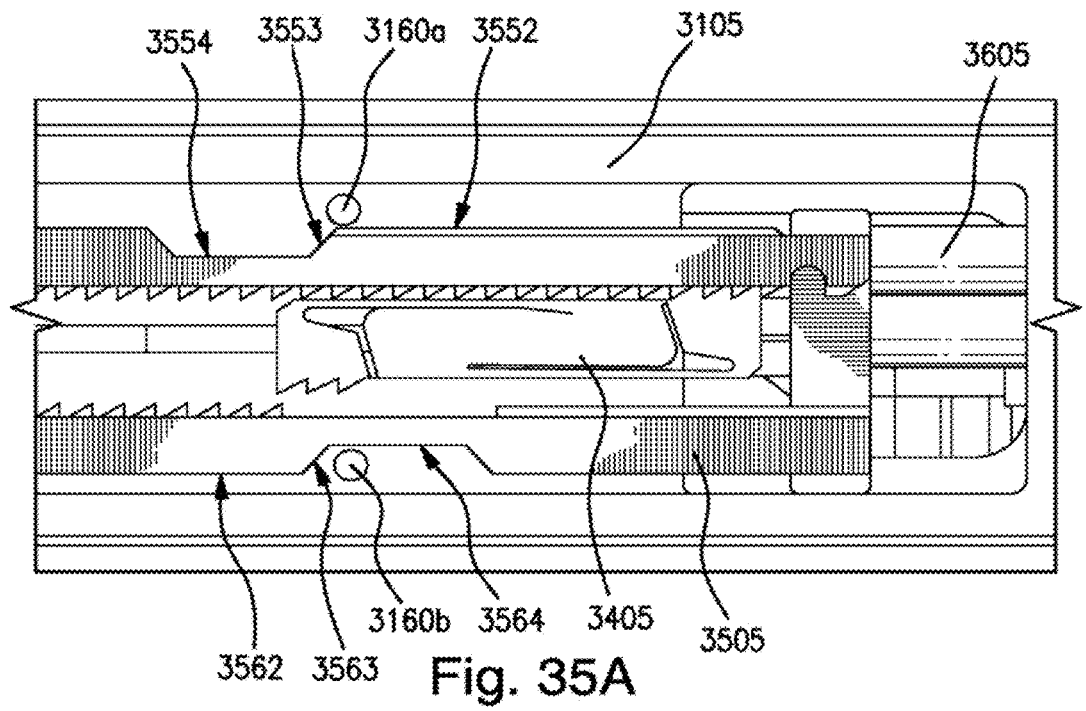
FIG. 35A shows the partial bottom view of the device of FIG. 32A at the start of a forward/distal stroke.
Figure 35B:
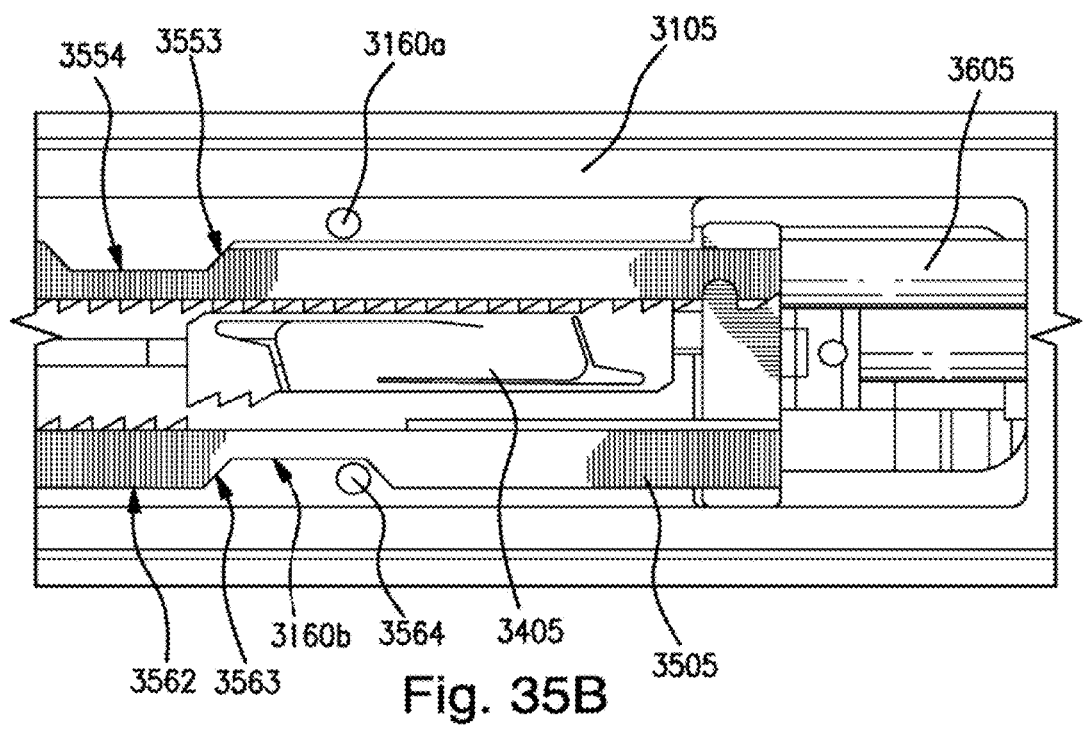
FIG. 35B shows the partial bottom view of the device of FIG. 32A at the end of a forward/distal stroke.
Figure 36A:
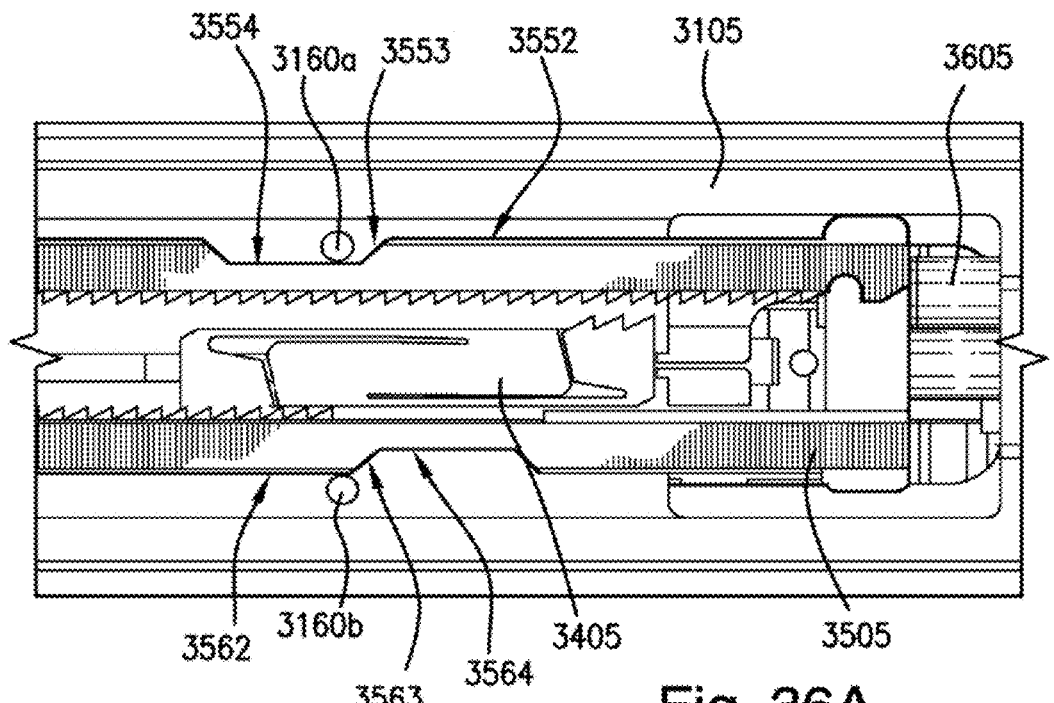
FIG. 36A shows the partial bottom view of the device of FIG. 32A at the start of a reverse/proximal stroke.
Figure 36B:
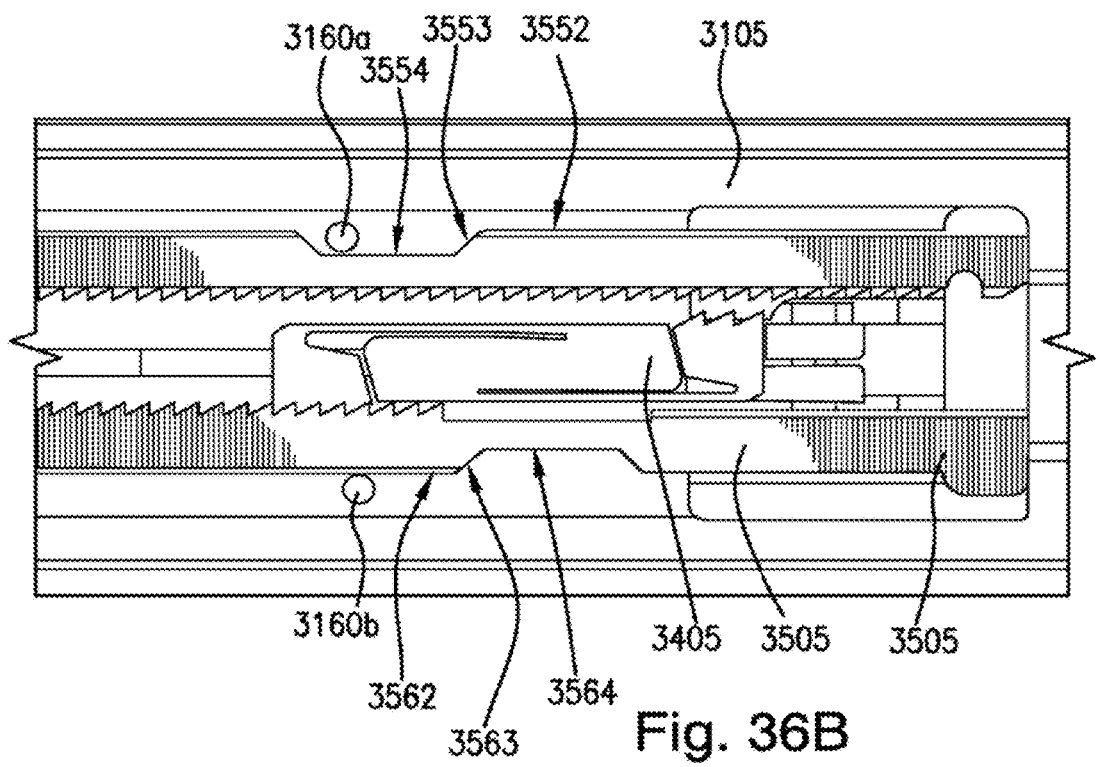
FIG. 36B shows the partial bottom view of the device of FIG. 32A at the end of a reverse/proximal stroke.

FIGS. 32 and 33 show the driving of staples 3910 of the reload housing 3905 during a distal actuation of carriage 3405 to simultaneously cut and staple tissue. As illustrated, the carriage 3405 is distally pushing the reload sled 3950 so that the wedges 3952 progressively push the staples 3910 upwardly toward the staple form plate 3260 in the anvil 3205 to form the staples. The wedges 3952 push the staples by progressively raising staple drivers 3920 disposed in the reload housing 3905. The staples are ejected via staple driving slots or apertures 3908 in the reload housing 3905.

It is noted that carriage 3405 travels a distal distance from its initial proximal position in the housing 3105 before engaging the anvil sled assembly 3268. It should be understood however, that this distance may be reduced or even eliminated if desired in additional example embodiments.

FIGS. 35A to 36B show an actuation mechanism of the device 3005 including a mechanism for shifting the actuating bar 3505 between its first and second lateral positions. The mechanism differs from that of the device 5, however, in that the alignment elements 3160*a*, 3160*b* are configured as pins. The pins 3160*a* and/or 3160*b* may be supported in the housing 3105, the cover 3180 and/or any other desirable structure of the housing assembly. FIGS. 35A to 36B are partial bottom views of the device 3005, with the device 3005 being: at the start of a forward/distal stroke in FIG. 35A; at the end of a forward/distal stroke in FIG. 35B; at the start of a reverse/proximal stroke in FIG. 36A; and at the end of a reverse/proximal stroke in FIG. 36B.

Figure 37:
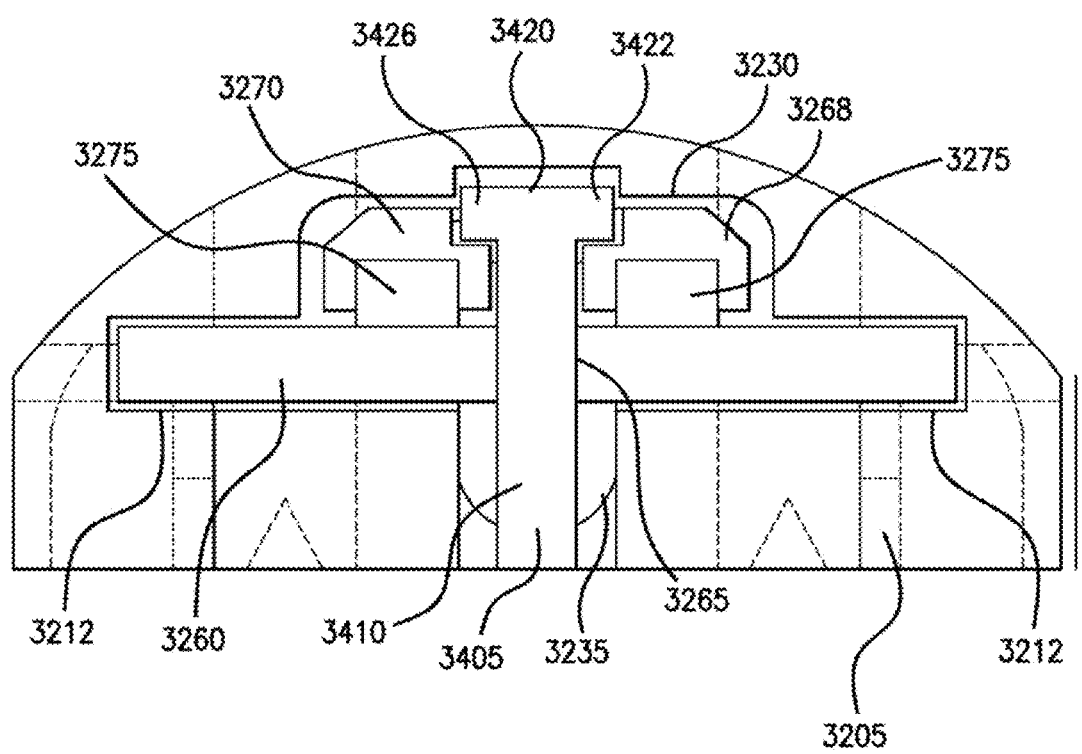
FIG. 37 is a partial cross-sectional view of the engagement of the carriage of the device of FIG. 32A with an anvil assembly.

FIG. 37 is a partial cross-sectional view of the engagement of the carriage 3405 of the anvil assembly 3268 within the anvil 3205. In this regard, the staple form plate 3260 is supported by two ledges or flanges 3212 so as to constrain the staple form plate 3260 from transversely moving with respect to the anvil 3205. The carriage 3405 extends vertically through the guide slot 3265 in the staple form plate 3260 and into a portion of the guide channel 3230 above the staple form plate 3260. In this region, the first jaw-engagement portion 3420 is engaged with the anvil latch plate 3270 of the anvil assembly 3268. In the configuration illustrated in FIG. 37, downwardly directed force exerted by the carriage 3405 is exerted from the opposed flanges 3422, 3426 of the upper jaw-engagement portion 3420 to the structure of the anvil latch plate 3270 disposed beneath the flanges 3422, 3426. This force is then transferred from the anvil latch plate 3270 into the two opposed low friction inserts 3275 disposed between the anvil latch plate 3270 and the staple form plate 3260. The force is then transferred from the low friction inserts 3275 to the staple form plate 3260, which then transfers the force to the anvil 3205 via the ledges or flanges 3212. In this manner, a downward force is exerted by the carriage 3405 on the anvil 3205 during the cutting and stapling procedure. A complementary corresponding upward force is exerted on the lower jaw via engagement of the lower jaw engagement portion 3430 with the housing 3105 in the same manner set forth above with regard to the device 5. Thus, the carriage 3405 is tensioned between the anvil 3205 and the housing 3105 to urge the anvil 3205 and the housing 3105 into their clamped relative positions in order to maintain a constant clamped tissue thickness as the carriage 3405 is axially advanced or retracted, e.g., via the reciprocating actuation mechanism described herein. The movement of the carriage 3405 from a proximal location to a distal location is sequentially illustrated in FIGS. 38A and 38B.

Referring, e.g., to FIGS. 38A and 38, the anvil sled assembly 3268 differs from the anvil sled assemblies 268, 1268 of the devices 5 and 1005 in that the anvil latch plate 3270 and the return link 3280 are formed as a single monolithic piece in an additional example embodiment.

When the carriage 3405 is proximally returned to its proximal position in the housing 3105 after the distal cutting and stapling movement, the carriage 3405 engages and slides the anvil sled assembly 3268 back to its original proximal position in the anvil 3205.

Figure 45:
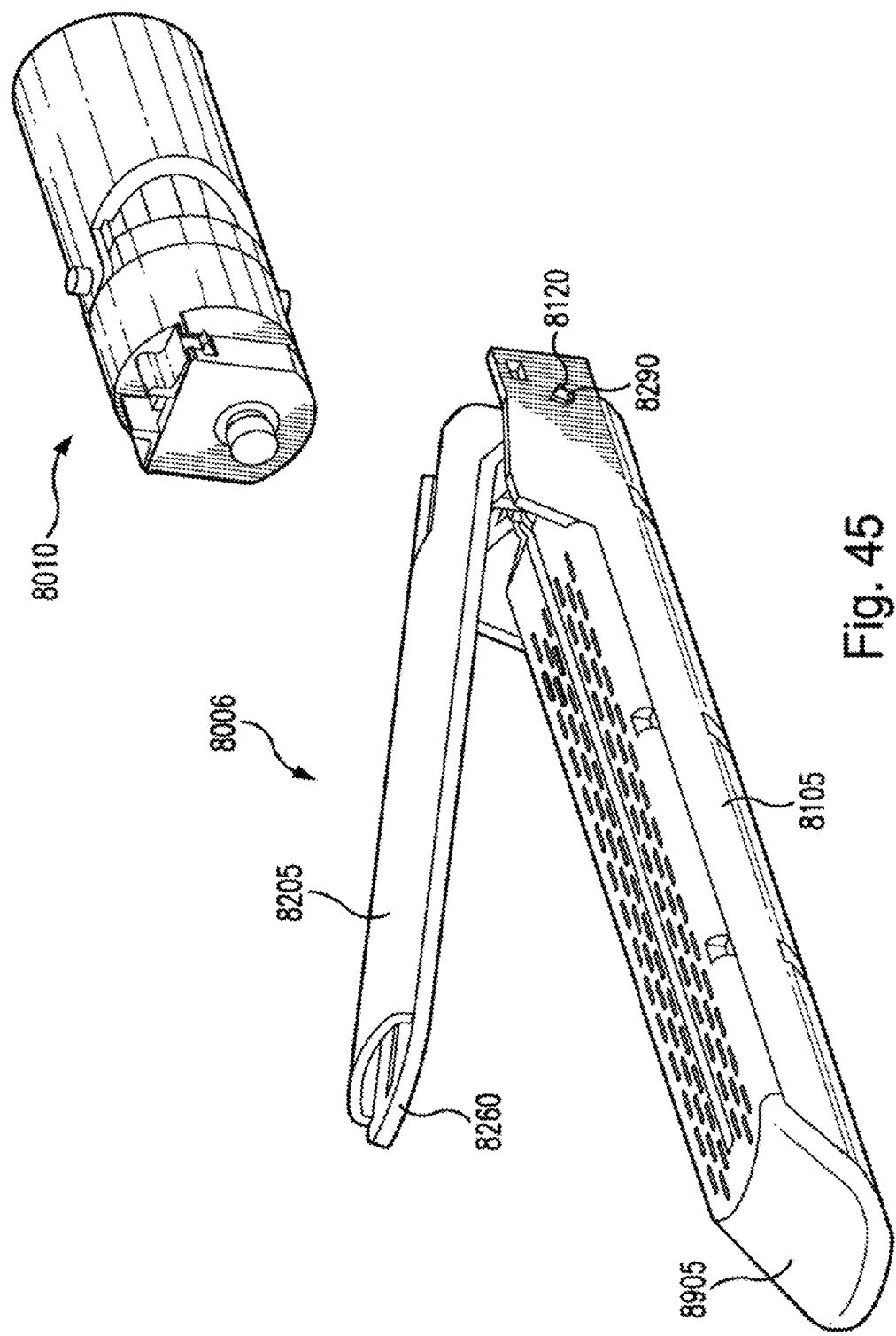
FIG. 45 is a perspective view of a head assembly of a surgical device according to an example embodiment of the present invention.

Referring to FIG. 45, head assembly 8006 and piston assembly 8010 of surgical device 8005 are illustrated. Head assembly 8006 includes housing 8105 and anvil 8205, similar to the devices 5, 1005, and 3005. The surgical device 8005 differs from the surgical devices 5, 1005, and 3005 in that surgical device 8005 does not include an anvil actuation piston, anvil actuation pins, or an anvil actuation slot. Instead, the anvil 8205 of device 8005 includes an anvil pivot flange 8290, which engages with the housing 8105 in the anvil pivot slot 8120, as described in further detail below.

Figure 46:
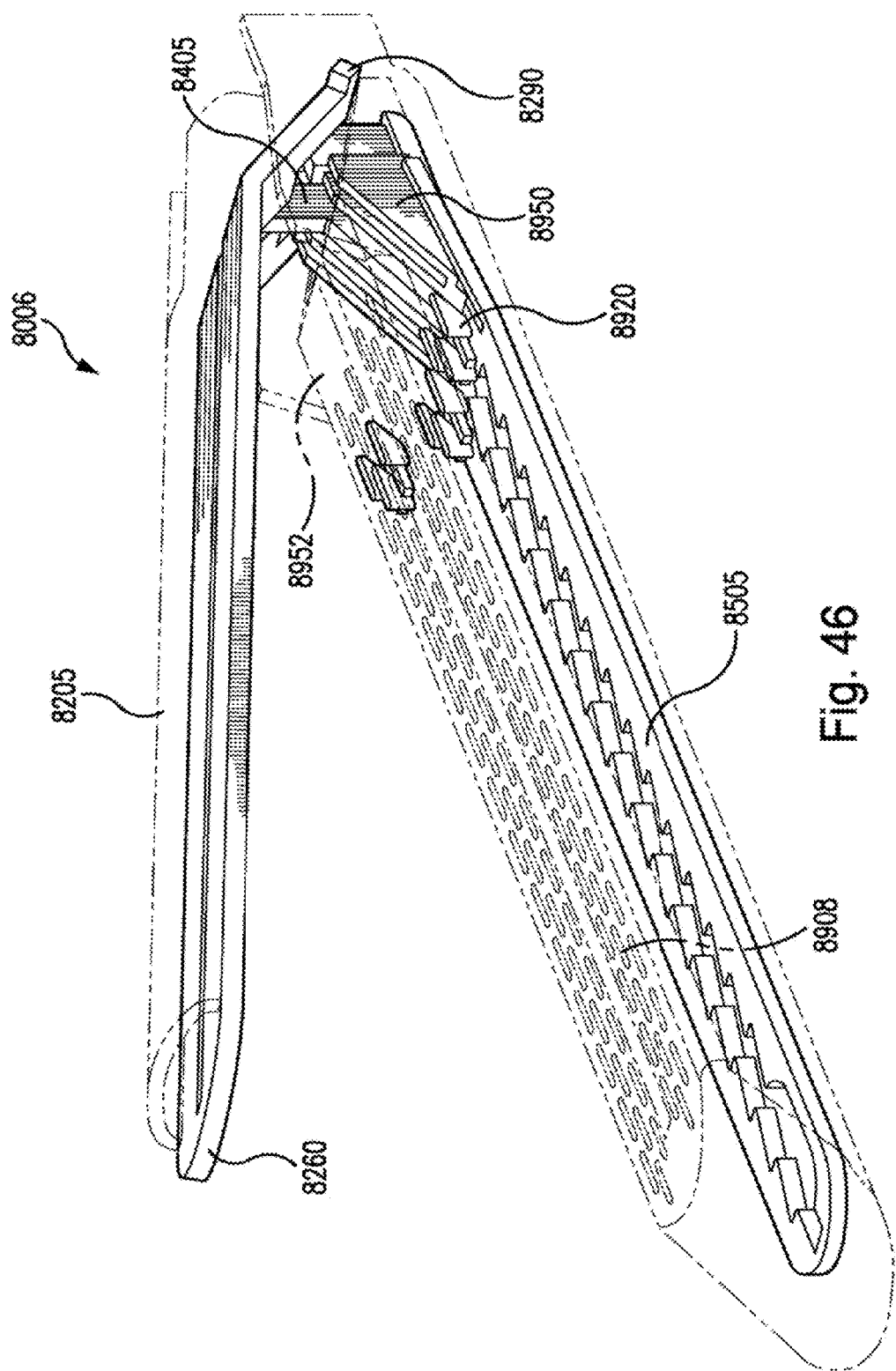
FIG. 46 is a perspective view of a head assembly of a surgical device according to an example embodiment of the present invention.

FIG. 46 illustrates head assembly 8006 of surgical device 8005, including carriage 8405, reload sled 8950, and staple-driving wedges 8952, situated above the actuating bar 8505. The carriage 8405 is located in its proximal position with respect to the head assembly 8006, and anvil 8205 is again open with respect to the housing 8105. Anvil pivot flange 8290 is also illustrated. Within reload housing 8905, staple drivers 8920 are illustrated. As in devices 5, 1005, and 3005, carriage 8405 of device 8005 is ratcheted forward, in the distal direction, causing staple-driving wedges 8952 to force the staple drivers 8920 into the staples (not shown).

Figure 47A:
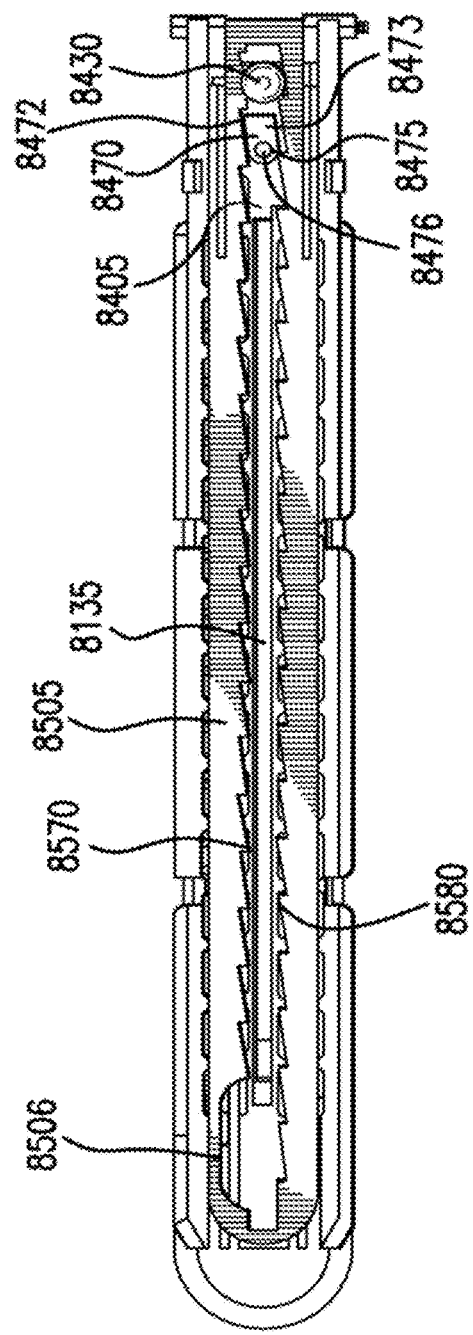
Figure 47B:
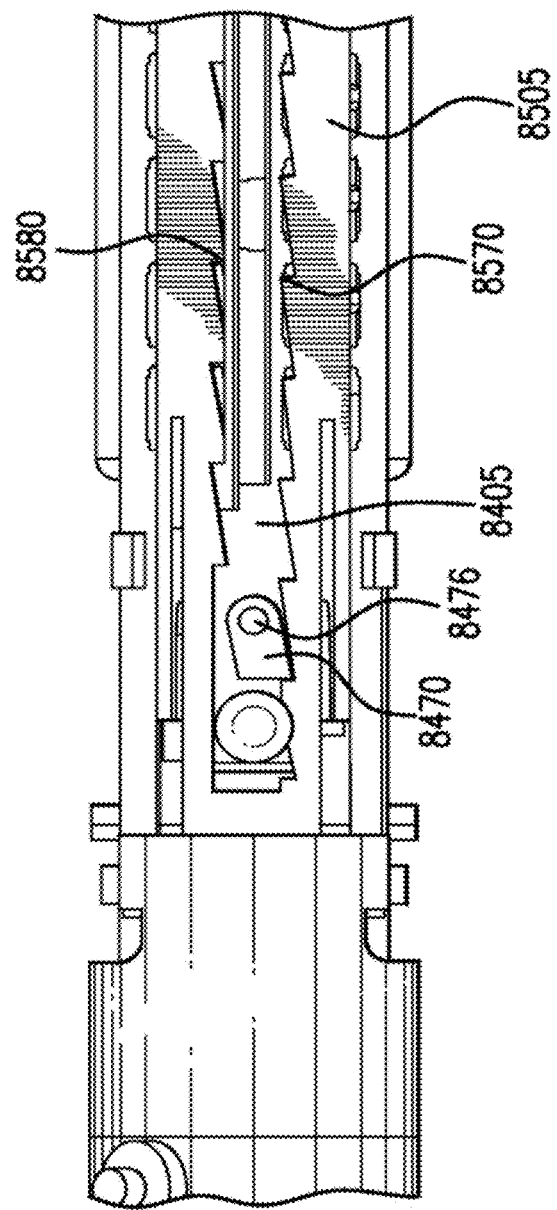

The ratcheting of the device 8005 differs from the ratcheting of the devices 5, 1005, 3005 in that carriage 8405 includes a spring-loaded bidirectional latching mechanism, or pawl 8470, instead of the ratcheting elements 470, 480 and spring arms 475, 485. FIGS. 47A to 47C illustrates actuating bar 8505, having a first set of teeth 8570 and a second set of teeth 8580, and further illustrates pawl 8470, having spring force transfer slot 8475, leading edge 8472, and following edge 8473. Also illustrated is carriage 8405, having spring force transfer pin 8476. Carriage 8405 engages pawl 8470 via spring force transfer pin 8476, situated in spring force transfer slot 8475 so as to impart a counter-clockwise spring force (from the perspective of FIG. 47) on pawl 8470. In the pre-surgical position, prior to actuation of surgical device 8005, as illustrated in FIG. 47, the counter-clockwise spring force urges leading edge 8472 of pawl 8470 into contact with first set of teeth 8570. First set of teeth 8570 are situated such that, upon movement of actuating bar 8505 in the distal direction, as will be described below, the engagement of leading edge 8472 of pawl 8470 with first set of teeth 8570 forces carriage 8405 to move in the distal direction, and upon movement of actuating bar 8505 in the proximal direction, as will be described below, the engagement of leading edge 8472 of paw 18470 with first set of teeth 8570 does not force carriage 8405 to move in the proximal direction. The distance between each tooth in the first set of teeth 8570 should be smaller than the oscillation of the actuating bar 8505, so that each proximal movement of the actuating bar 8505 permits the pawl 8470 (which remains under counter-clockwise spring-loaded force) to engage with the next tooth in the distal direction of first set of teeth 8570. In this manner, the oscillation of the actuating bar 8505 creates a ratcheting operation, moving pawl 8470, and therefore carriage 8405, in the distal direction.

At the distal end of first set of teeth 8570, actuating bar 8505 includes an enlarged opening 8506 on the lateral side of actuating bar 8505 which includes first set of teeth 8570. As the ratcheting operation proceeds, carriage 8405 and pawl 8470 eventually reaches the distal end, where leading edge 8472 of pawl 8470, after engaging the last tooth in first set of teeth 8570, reaches enlarged opening 8506. Enlarged opening 8506 is large enough that the counter-clockwise spring-loaded force causes pawl 8470 to rotate about the spring force transfer pin 8476 until leading edge 8472 of pawl 8470 engages with second set of teeth 8580 on the lateral side of actuating bar 8505 opposite first set of teeth 8570. Second set of teeth 8580 are situated in the opposite manner as first set of teeth 8570, such that, upon movement of actuating bar 8505 in the proximal direction, as will be described below, the engagement of leading edge 8472 of pawl 8470 with second set of teeth 8580 forces carriage 8405 to move in the proximal direction, and upon movement of actuating bar 8505 in the distal direction, as will be described below, the engagement of leading edge 8472 of pawl 8470 with second set of teeth 8580 does not force carriage 8405 to move in the distal direction. The distance between each tooth in the second set of teeth 8580 should be smaller than the oscillation of actuating bar 8505, so that each distal movement of actuating bar 8505 permits pawl 8470 (which remains under counter-clockwise spring-loaded force) to engage with the next tooth in the proximal direction of second set of teeth 8580. In this manner, the oscillation of actuating bar 8505 creates a ratcheting operation, moving pawl 8470, and therefore carriage 8405, in the proximal direction. This arrangement benefits from the use of the same force (i.e., the oscillating piston and actuating bar) to move the carriage in the distal direction and in the proximal direction, with only the simple rotation of the spring-loaded pawl. There are no complicated mechanisms for reversing the moving direction of the carriage, so that the resulting systems is less complicated, simpler to operate, simpler and cheaper to manufacture, and more efficient.

Figure 48:
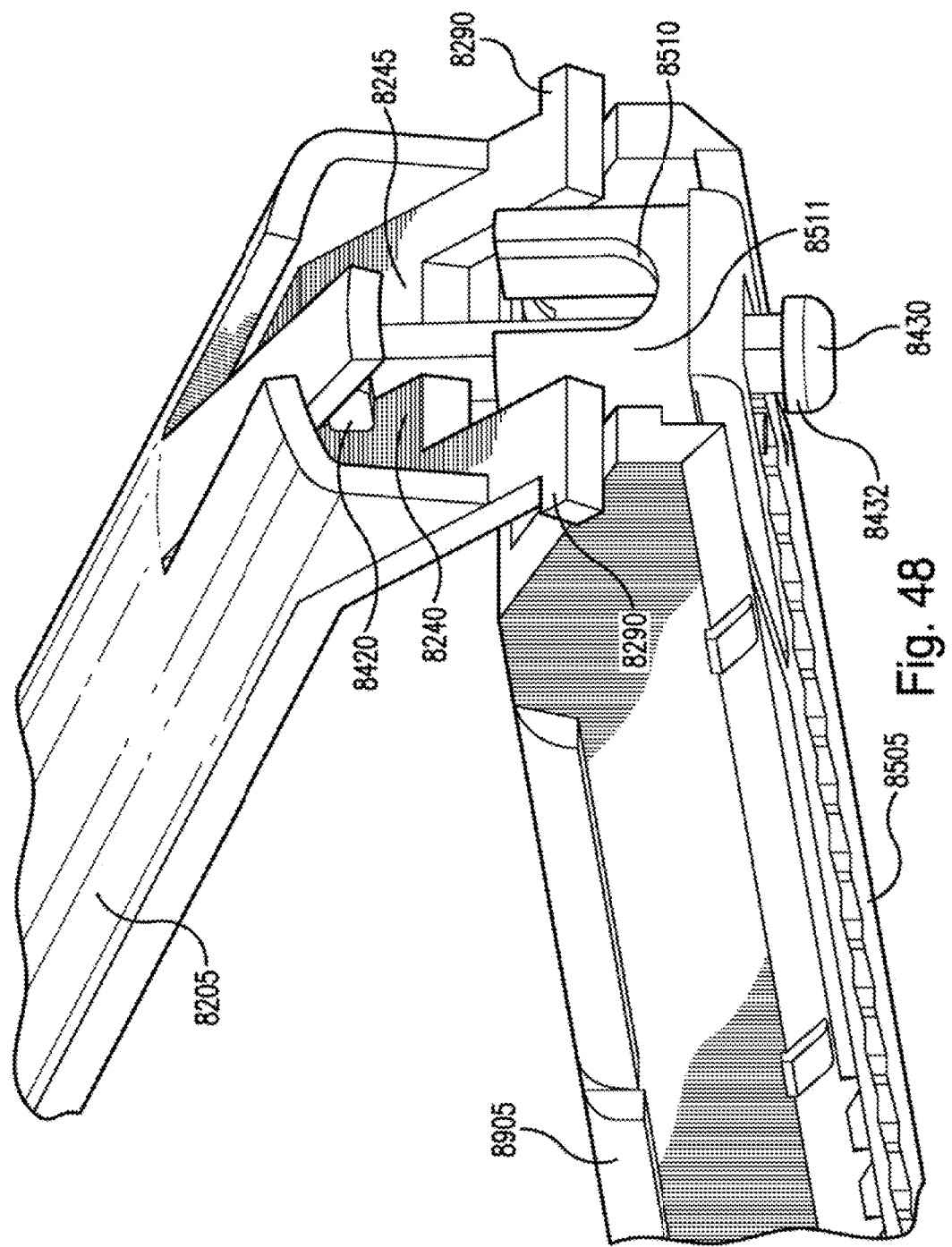
FIG. 48 is a perspective view of a connection assembly of the device of FIG. 45.
Figure 53:
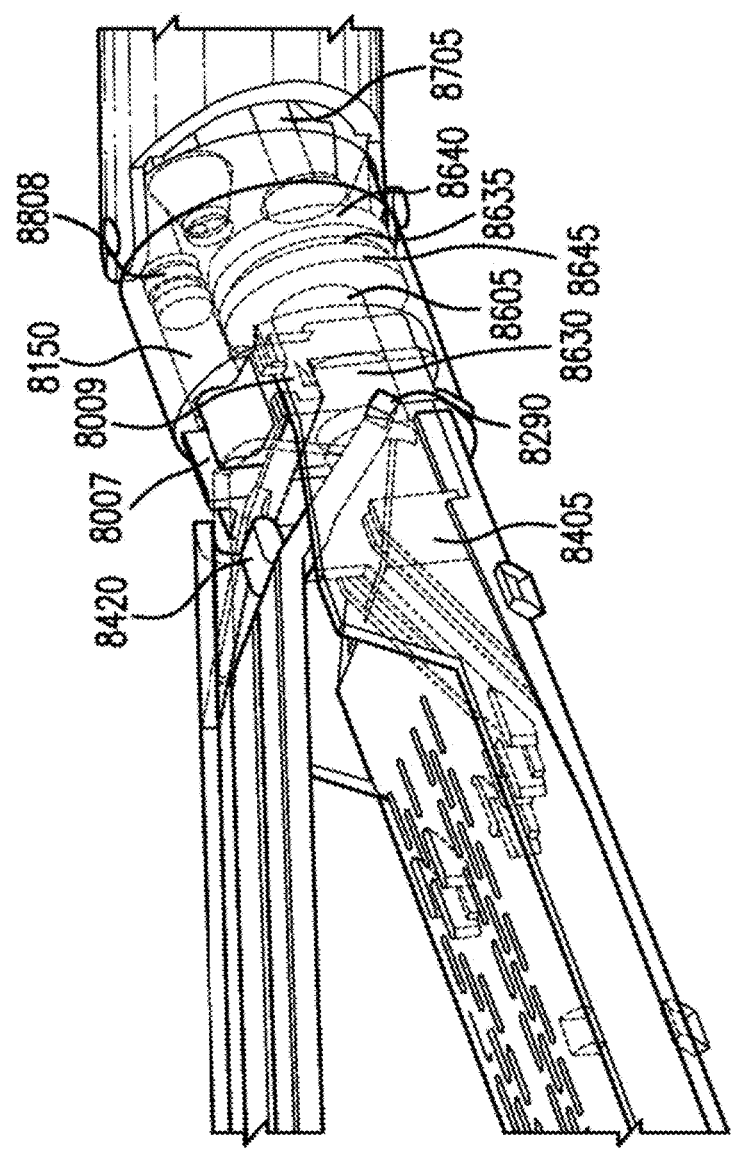
FIG. 53 is a perspective view of the carriage, connection assembly, and hydraulic actuation system of the device of FIG. 50.
Figure 54:
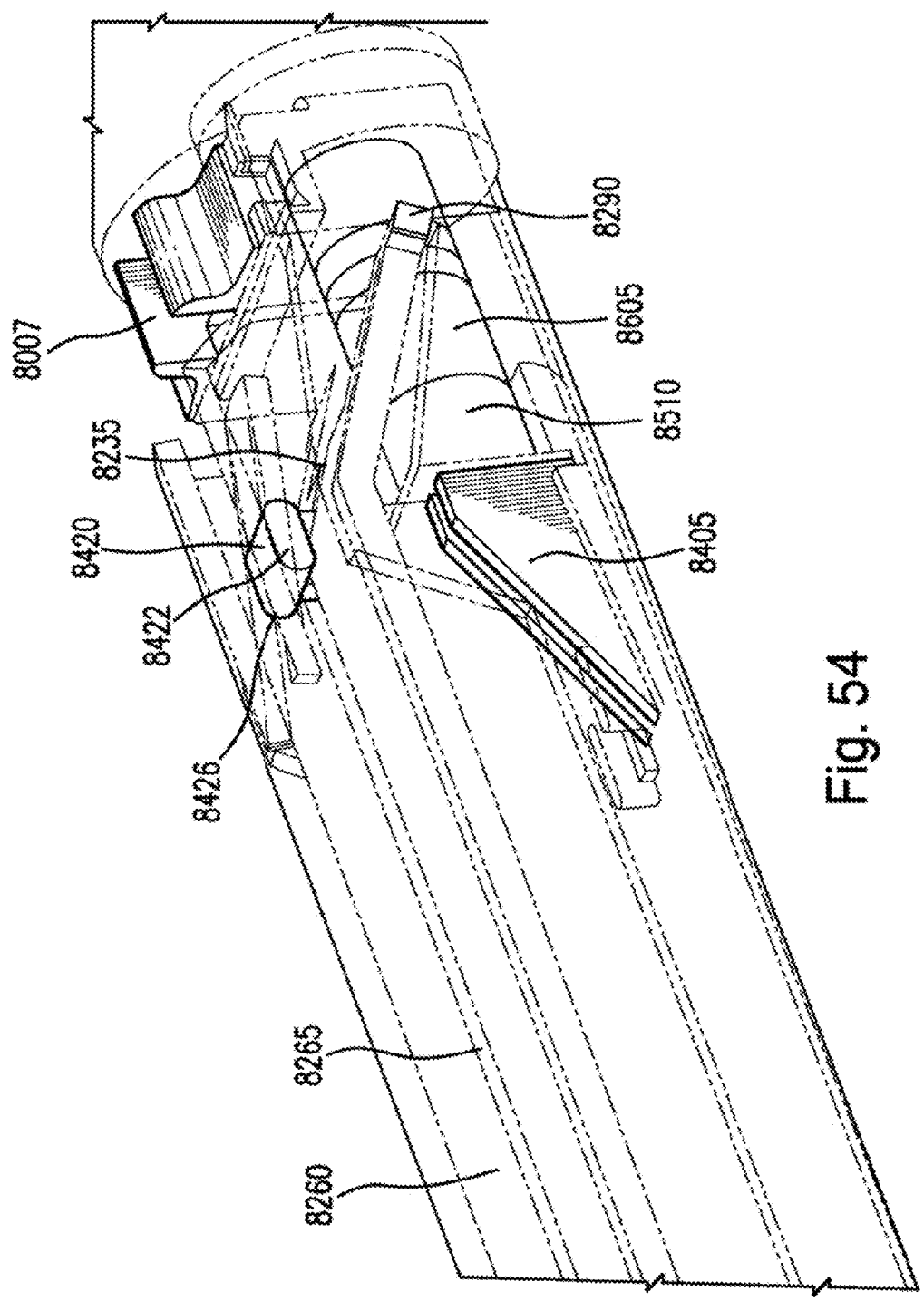
FIG. 54 is a perspective view of the carriage, connection assembly, and hydraulic actuation system of the device of FIG. 50.

As noted above, device 8005 differs from devices 5, 1005, and 3005 in that device 8005 does not include an anvil actuation piston, anvil actuation pins, or an anvil actuation slot. Instead, referring to FIG. 48, the anvil 8205 of device 8005 includes anvil pivot flanges 8290. Carriage 8405 includes first jaw engagement portion 8420 and second jaw engagement portion 8430. First jaw engagement portion 8420 includes flanges 8422 and 8426. Second jaw engagement portion 8430 includes rounded flange 8432. Flanges 8422 and 8426 engage carriage 8405 with anvil 8205, and rounded flange 8432 engages carriage 8405 with housing 8105. Referring to FIGS. 48, 53, and 54, as carriage 8405 moves in the distal direction of head assembly 8006, downwardly directed force exerted by the carriage 8405 is exerted from the opposed flanges 8422, 8426 of the upper jaw-engagement portion 8420 to the staple form plate 8260 disposed beneath the flanges 8422, 8426. The force is transferred to the staple form plate 8260, which then transfers the force to the anvil 8205. In this manner, a downward force is exerted by the carriage 8405 on the anvil 8205 during the cutting and stapling procedure. A complementary corresponding upward force is exerted on the lower jaw via engagement of the lower jaw engagement portion 8430 with the housing 8105 in the same manner set forth above with regard to the device 5. Thus, the carriage 8405 is tensioned between the anvil 8205 and the housing 8105 to urge the anvil 8205 and the housing 8105 into their clamped relative positions in order to maintain a constant clamped tissue thickness as the carriage 8405 is axially advanced or retracted, e.g., via the reciprocating actuation mechanism described herein.

Referring to FIGS. 48, 53, and 54, the actuating bar 8505 of device 8005 differs from the actuating bars 505 and 1505 of the devices 5 and 1005 in that it includes a force transfer rib 8510 in an additional example embodiment, similar to the force transfer rib 3510 of the device 3005, instead of force transfer slots 510, 1510. As in the device 3005, the ratchet piston 8605 is configured to mate with the actuating bar 8505 in a manner analogous to that set forth above with respect to ratchet pistons 605, 1605 and actuating bars 505, 1505 of devices 5 and 1005, except that instead of a projection or male member 610, 1610 of the ratchet piston 605, 1605 extending into a recess or female structure of the actuating bar 505, 1505, the ratchet piston 8605 includes a recess or female structure 8610 configured to receive a rib 8510 of the actuating bar 8505. The transversely extending force transfer rib 8510 of the actuating bar 8505 extends into the circumferential recess 8610 of the shaft 8630, thereby axially constraining the actuating bar 8505 with respect to the ratchet piston 8605. Ratchet piston 8605, as in ratchet pistons 605, 1605, and 3605, includes o-ring groove 8635, proximal o-ring retention wall 8640, and distal o-ring retention wall 8645. The actuating bar 8505 differs from the actuating bar 3505 of device 3005 in that the force transfer rib 8510 has two upward projections 8511 that extend into the circumferential recess 8610 of the ratchet piston 8605. Thus, the extension of the projections 8511 into a greater portion of the circumferential recess 8610 allows for increased structural integrity at the point of force transfer between the ratchet piston 8605 and the actuating bar 8505 during the distal movement of the carriage 8405. The actuating bar 8505 does not include the plurality of lateral positions of actuating bars 5, 1505, and 3505, as further described herein.

In the fourth exemplary surgical device 8005, carriage 8405 first sits in its home, or proximal, position. In this position, first jaw engagement portion 8420 of carriage 8405 is not engaged with anvil 8205, or is only partially engaged with anvil 8205, and anvil 8205 is in an open position, being spring loaded to the open position. Pawl 8470 may be engaged with the proximal tooth in the first set of ratchet teeth 8570, or may be in the most proximal position with respect to actuating bar 8505. As force from ratchet piston 8605 is transferred to actuating bar 8505, pawl 8470 engages with the proximal tooth in the first set of ratchet teeth 8570, distally driving carriage 8405. As carriage 8405 moves in the distal direction, first jaw engagement portion 8420 engages with guide channel 8230 and guide flanges 8240 and 8245 to exert a clamping force on anvil 8205, bringing anvil 8205 into a closed position. The first distal movement of carriage 8405 closing anvil 8205 may be about 3 mm. The length of the first distal movement may be substantially the same or slightly greater than the length of the piston stroke of ratchet piston 8605 and the axial distance between the first proximal position of pawl 8470 with respect to the first set of ratchet teeth 8570 and the second proximal position of pawl 8470 to engage the second proximal tooth of the first set of ratchet teeth 8570. Within the distance of this first stroke or first tooth, the distal movement of carriage 8405 may be stopped, and carriage 8405 proximally withdrawn, so as to open anvil 8205 and prevent the surgical stapling process from proceeding. Once carriage 8405 has progressed beyond this first distance, the staple firing process proceeds. This arrangement overcomes the need for a second piston to close the anvil, and instead provides for only one piston to close the anvil, drive the staples, and advance the knife blade. A single-piston system is less complicated, simpler to operate, simpler and cheaper to manufacture, and more efficient.

Figure 49:
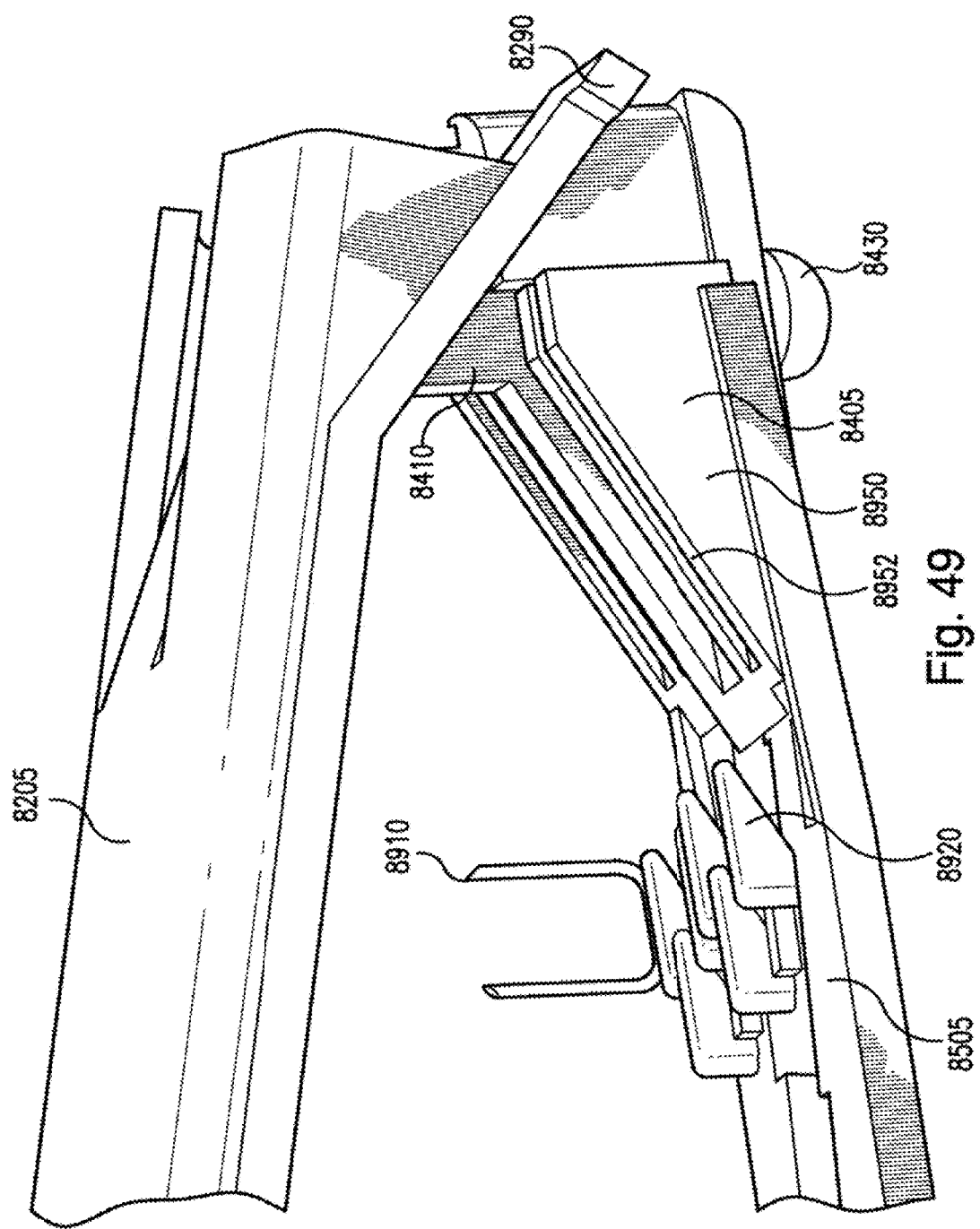
FIG. 49 shows a carriage and staple driver of the device of FIG. 45.
Figure 50:
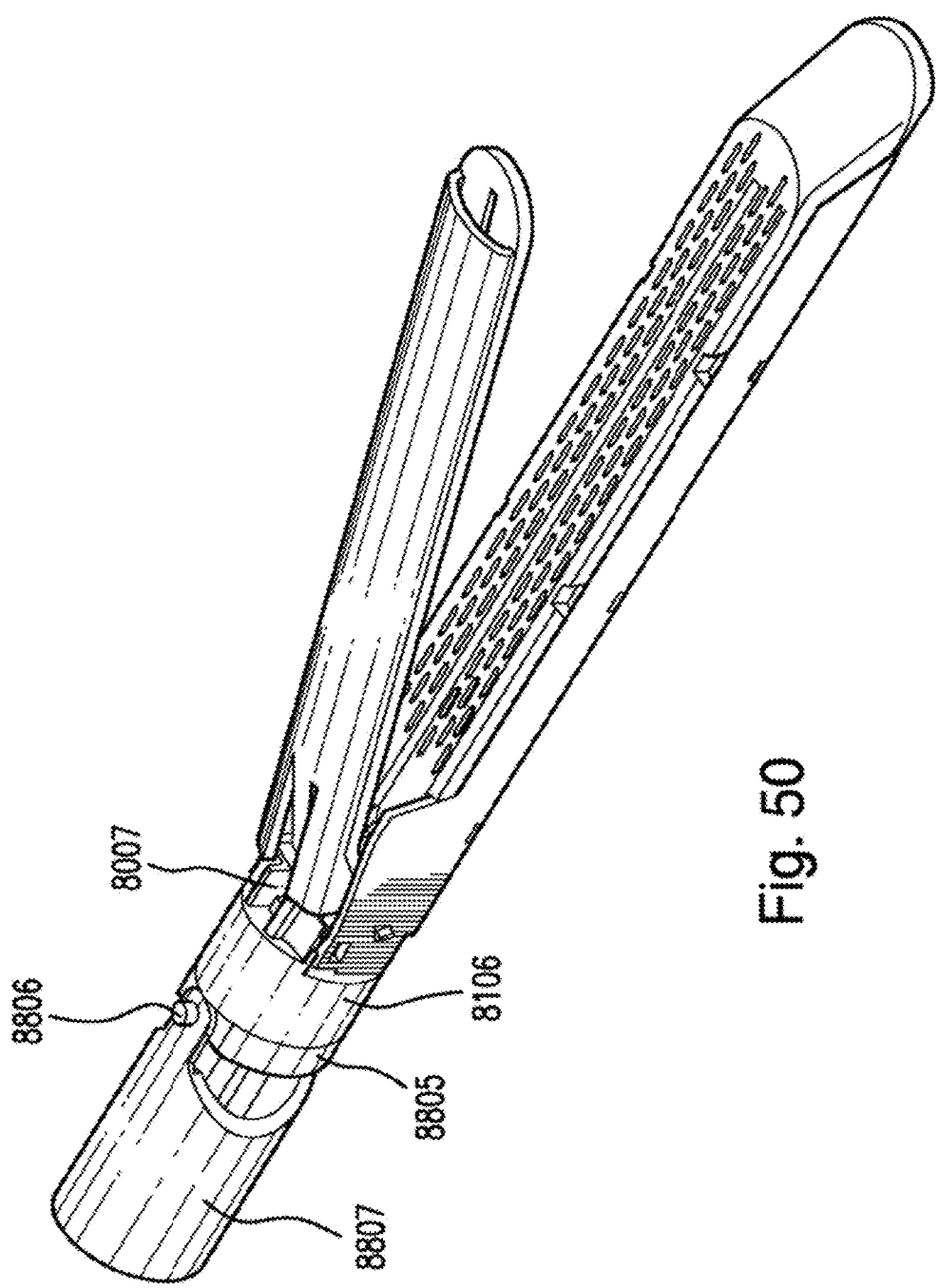
FIG. 50 is a perspective view of a surgical device according to an example embodiment of the present invention.
Figure 51:
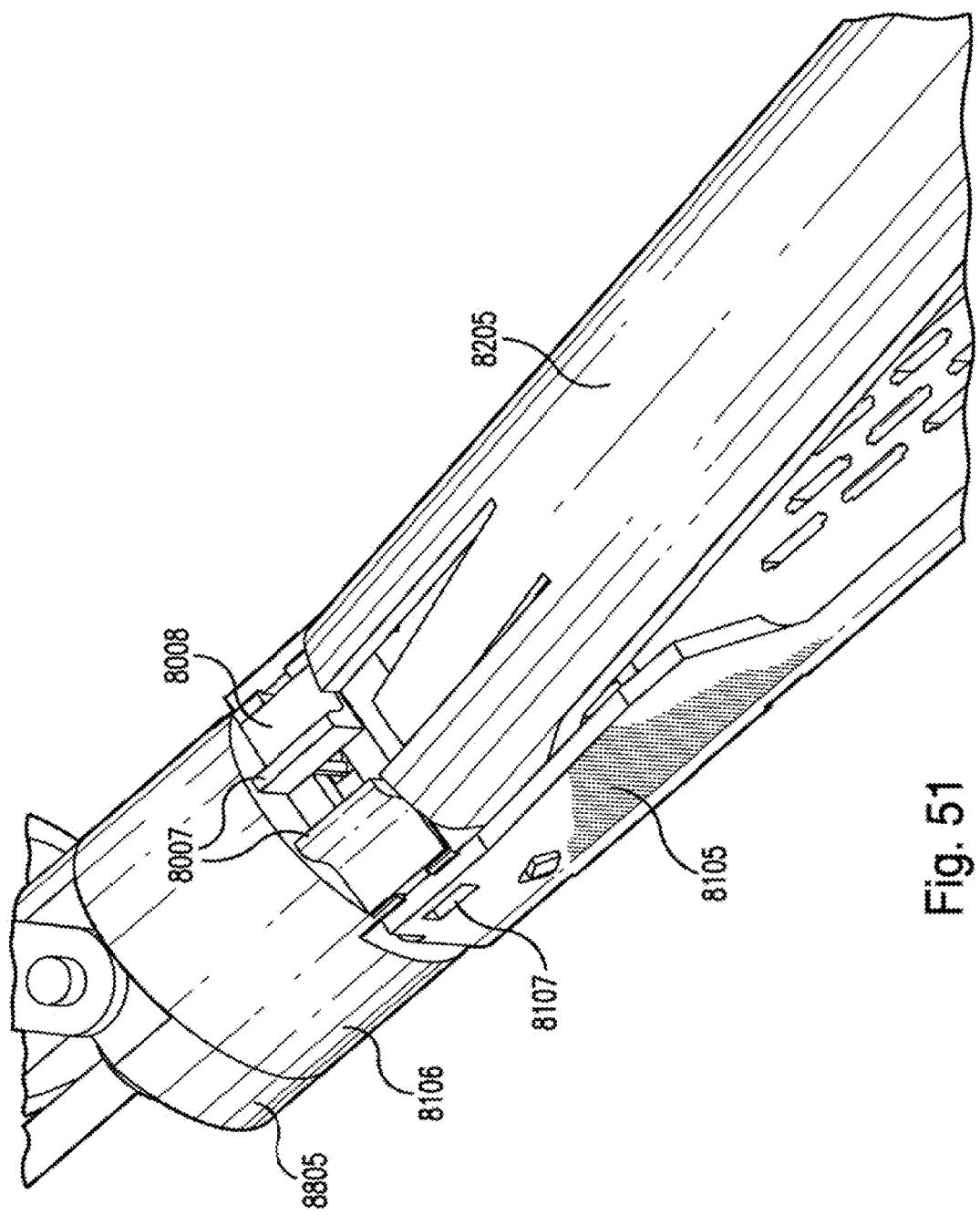
FIG. 51 shows a top view of a connection assembly of the device of FIG. 50.
Figure 52:
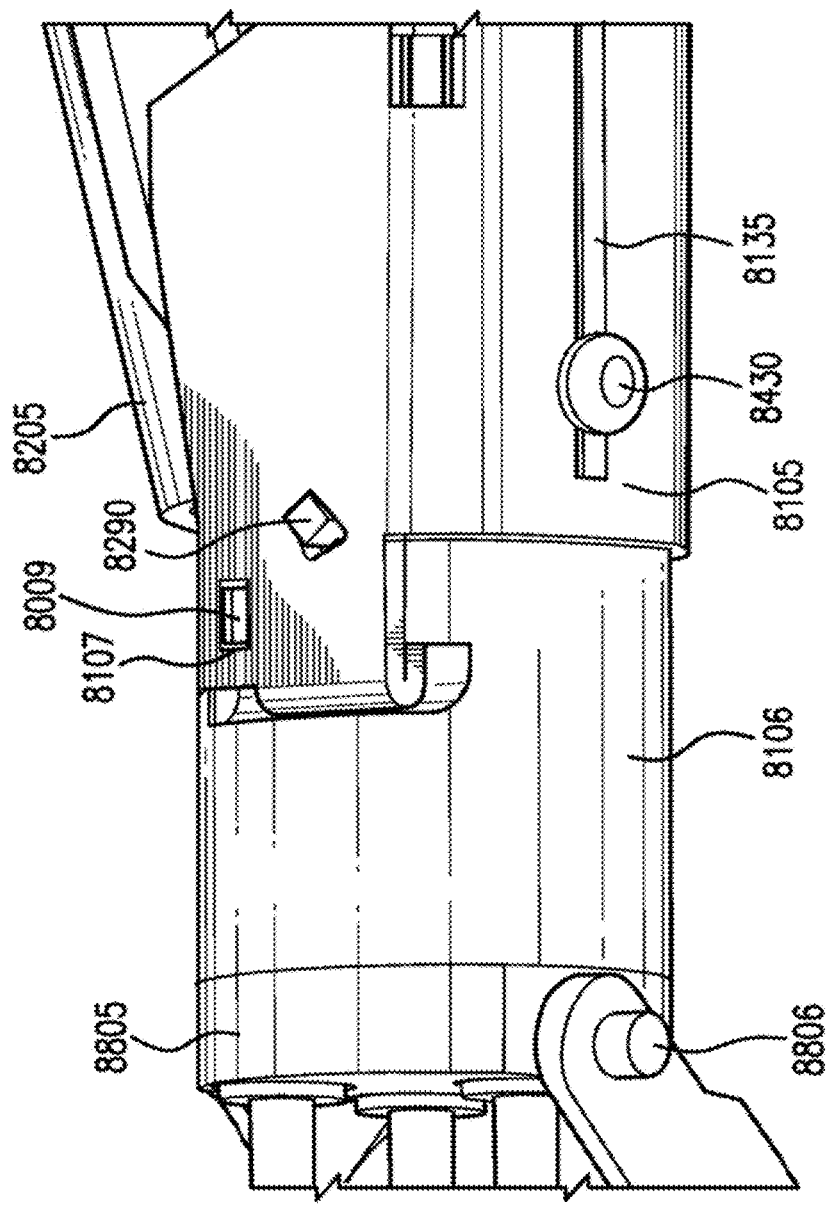
FIG. 52 shows a partial bottom view of a connection assembly of the device of FIG. 50.

FIG. 49 illustrates anvil 8205, carriage 8405, actuating bar 8505, staple drivers 8920, and one exemplary staple 8910. Carriage 8405 includes plate 8410. While no knife blade is shown in FIG. 49, any of blades 450, 1450, 3450 from devices 5, 1005, 3405 are possible.

Figure 55:
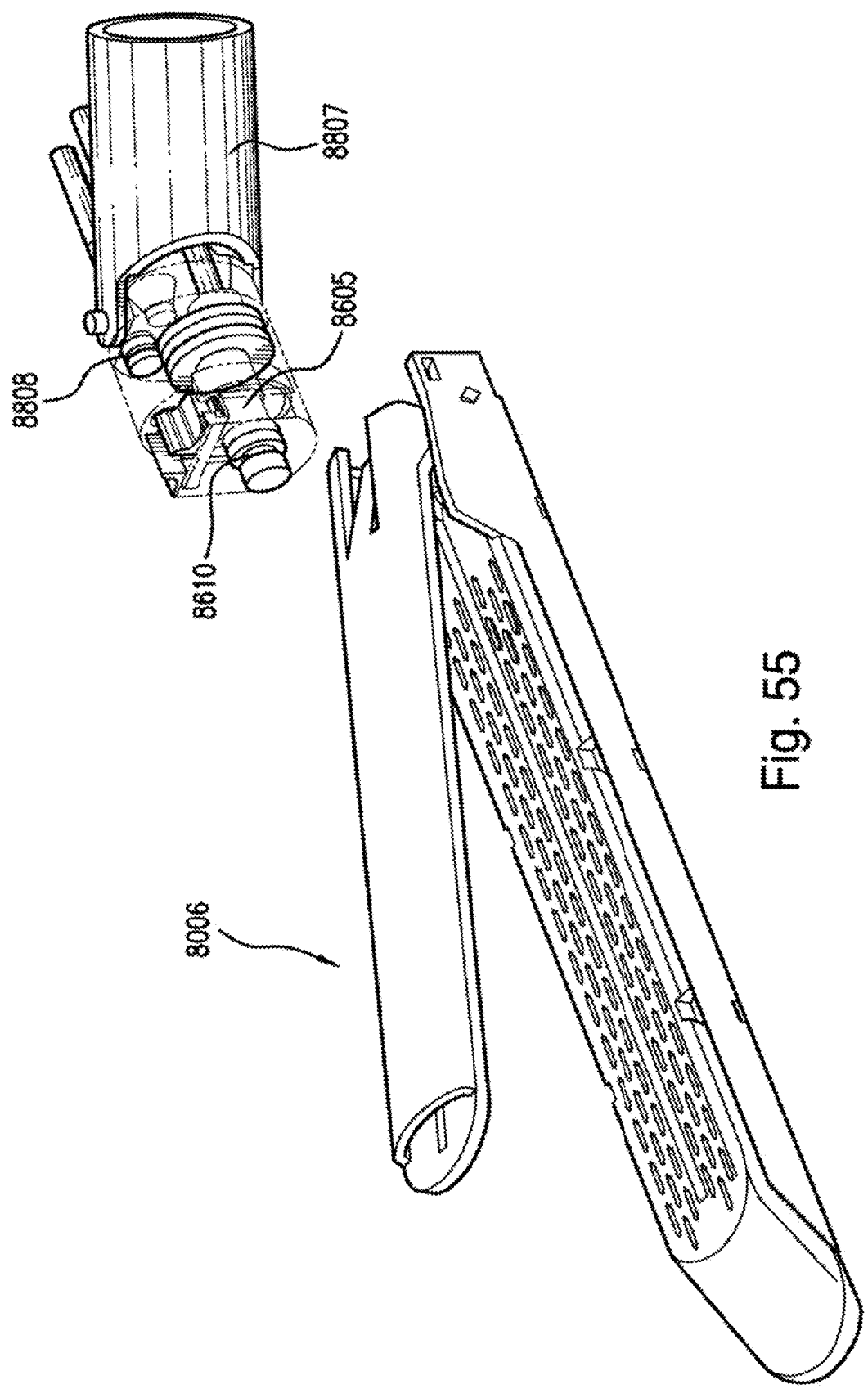
FIG. 55 is a perspective view of the carriage, connection assembly, and hydraulic actuation system of the device of FIG. 50.
Figure 56A:
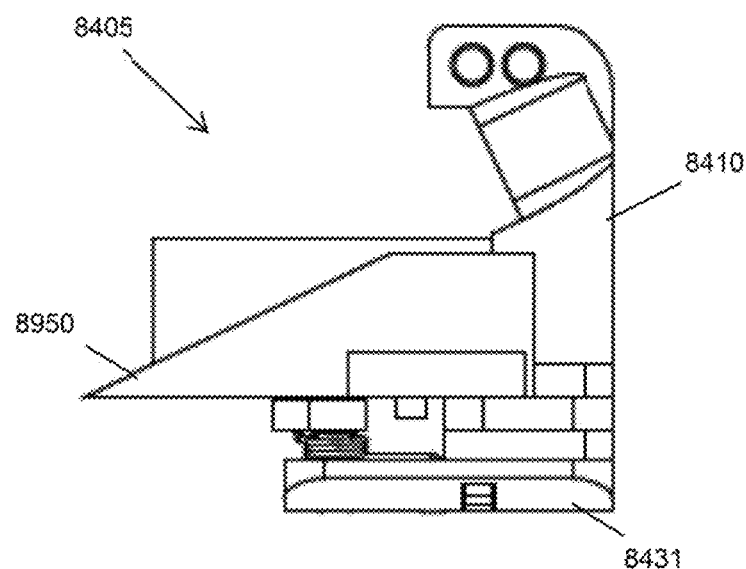
FIGS. 56A, B, and C are perspective and side views of the carriage and sled assembly.
Figures 56B, 56C:
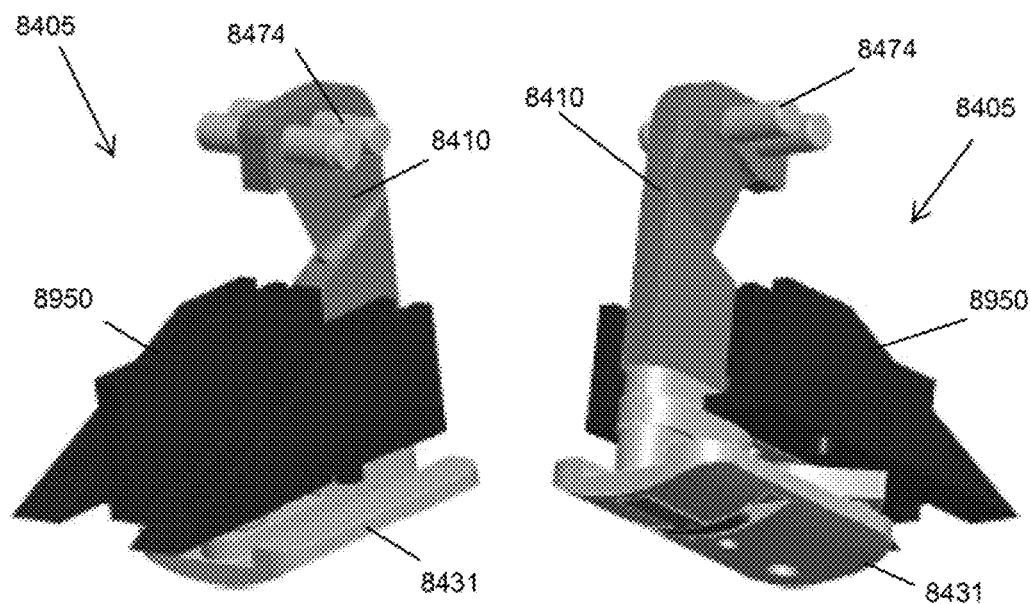
Figure 57:
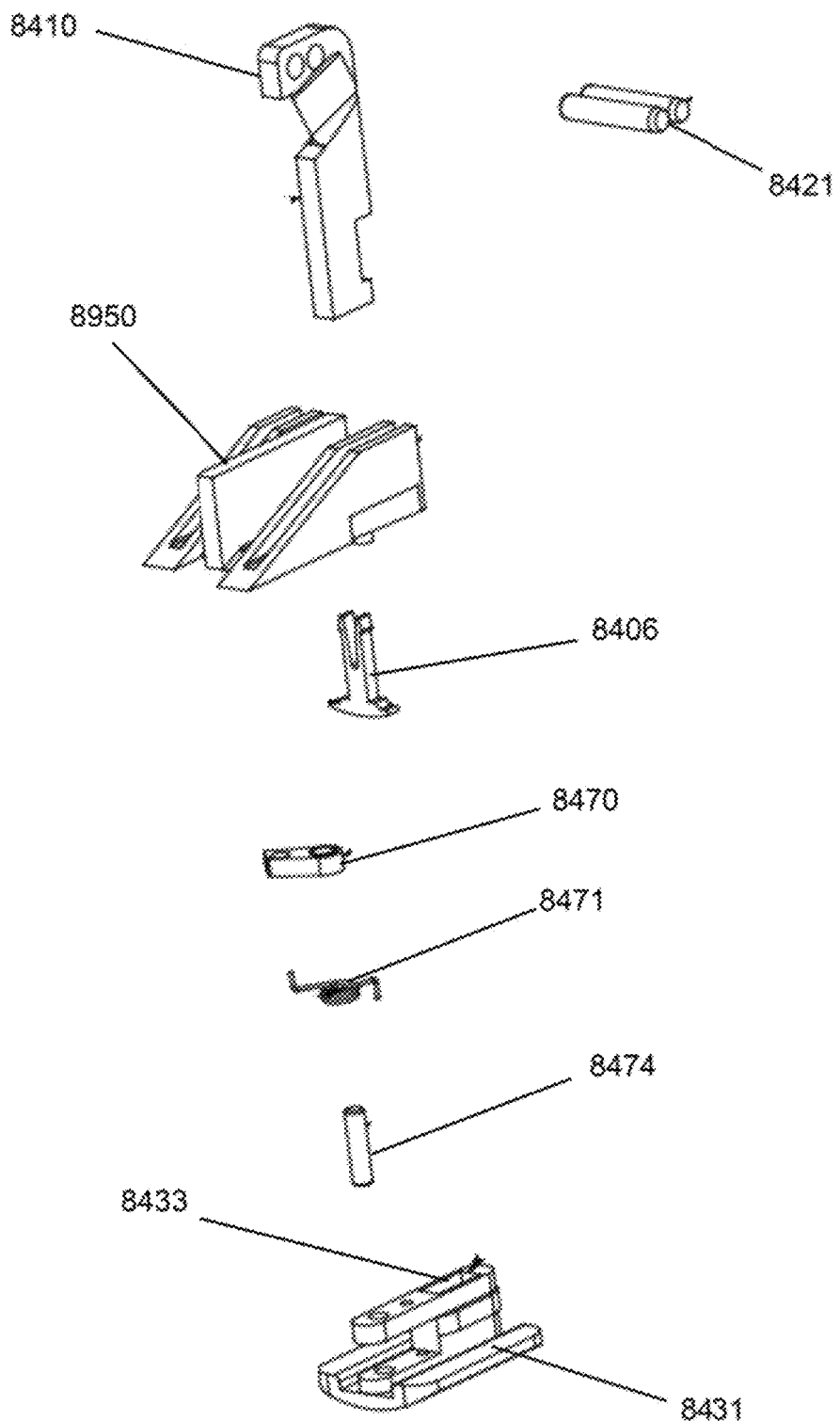
FIG. 57 is an exploded view of the carriage and sled assembly

Referring to FIGS. 45 and 50 through 55, head release latch 8007 is illustrated connecting head assembly 8006 (including anvil 8205 and housing 8105) to housing 8106, rear cap 8805, and steering column 8807. Head release latch 8007 includes head release operating members 8008 and head release flanges 8009. In operation, head release flanges 8009 are situated in head release slots 8107. When connected, as illustrated more specifically in FIGS. 53 and 54, head release flanges 8009 are engaged with head release slots 8107, and ratchet actuation piston 8630 is engaged, via circumferential recess 8610, to force transfer rib 8510 of actuating bar 8505. To release head assembly 8006 from the hydraulic system, as illustrated in FIG. 55, a user may use head release operating members 8008 to withdraw flanges 8009 from slots 8107. In combination with the double-action piston driving actuating bar 8505, and therefore the closed hydraulic actuation system, the release of the head assembly allows for a new head assembly to be used for each implementation of the surgical device. A new head assembly, including a new anvil, new staples, and a new knife blade, provides the benefit of increased sterility, and simplifies efforts to maintain a clean and sterile surgical device.

As further illustrated in FIGS. 50 through 55, steering head 8807, connected to the end of flexible tube 5410, may be hydraulically actuated to provide hydraulic steering for head assembly 8006 when connected to housing 8106. Steering head 8807 is engaged with rear cap 8805 via pin 8806, about which the axial direction of head assembly 8006 may be adjusted, with respect to steering head 8807. Hydraulic steering is effected via steering piston 8808, which may be a single-action or double-action piston. In a known hydraulic manner, steering piston 8808 may be advanced to a distal end, or drawn to the proximal end, of a steering piston cylinder 8150. When steering piston 8808 is situated half way between the distal and proximal ends of steering piston cylinder 8150, head assembly 8006 is situated in the same axial direction as steering head 8807. Advancing steering piston 8808 to the distal end of the steering piston cylinder 8150, or drawing steering piston 8808 to the proximal end of the steering piston cylinder 8150, may adjust the axial direction of head assembly 8006 to the left or the right, with respect to steering head 8807.

Figure 58:
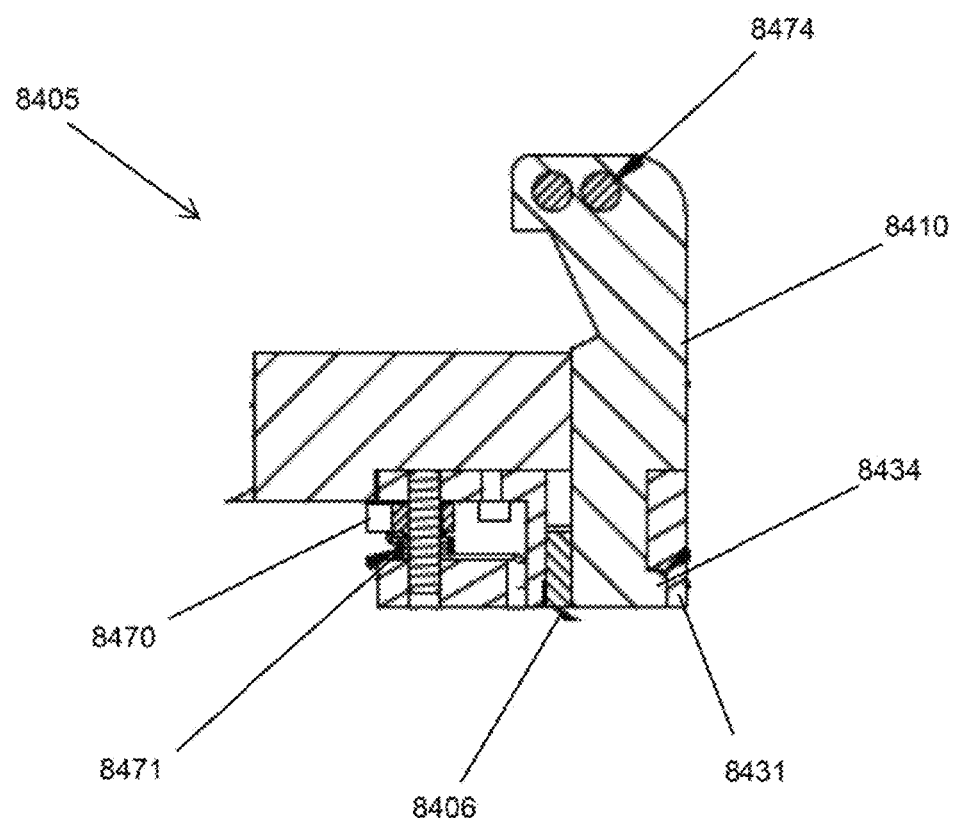
FIG. 58 is a partial view of the carriage and sled assembly.
Figure 59A:
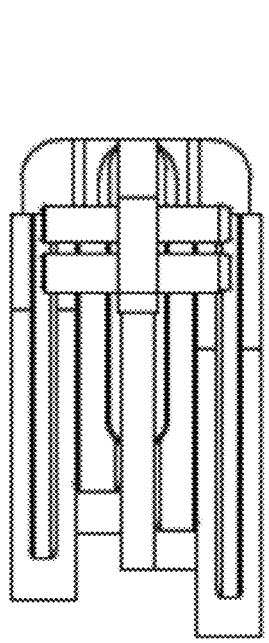
FIGS. 59A, B, and C are top, side, and bottom views of the carriage and sled assembly.
Figure 59B:
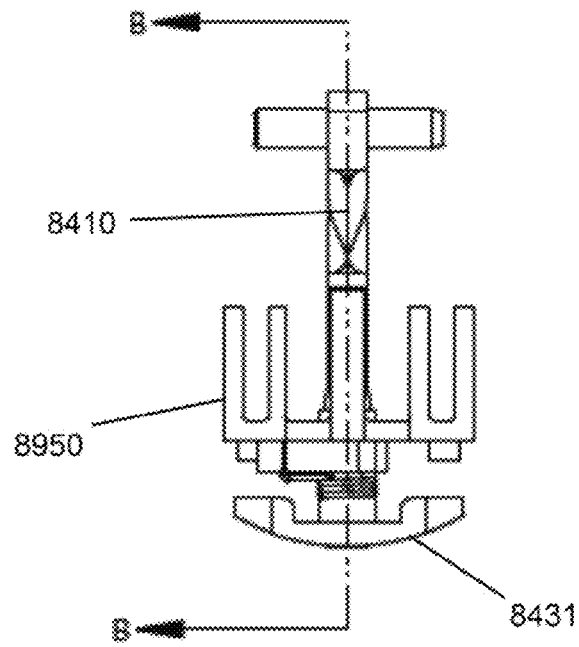
Figure 59C:
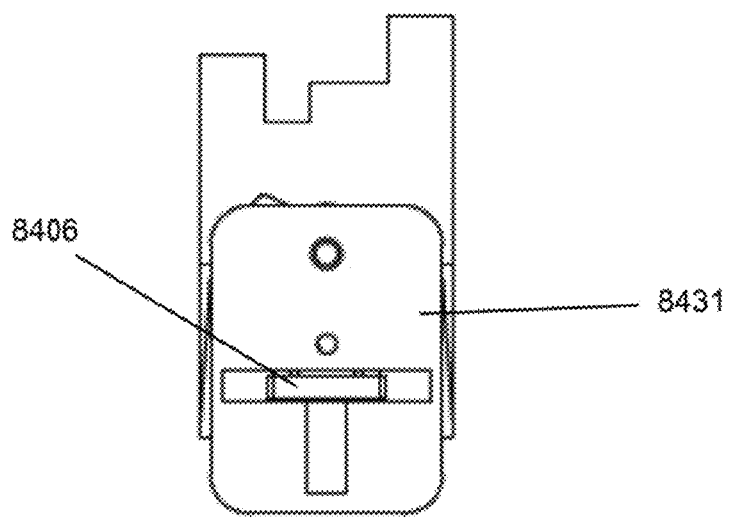

It is desirable to provide a release mechanism, in the event a failure occurs during operation of the device. Accordingly, the assembly of the sled and force transfer bar may be further arranged as illustrated in FIGS. 56A to 59C. In place of first jaw engagement portion 8420 having flanges 8422 and 8426, in this example embodiment, dowel pins 8421 engage carriage 8405 with anvil 8205. Further, in place of second jaw engagement portion 8430 having rounded flange 8432, sled base 8431 engages carriage 8405 with housing 8105. Force transfer bar 8410 fits into receptacle 8433 of sled base 8431, which includes a locking tang 8434 to receive a protrusion extending proximally from the bottom of force transfer bar 8410. Receptacle 8433 of sled base 8431 is large enough to receive the lower end of force transfer bar 8410, so that the protrusion extending from the bottom of force transfer bar 8410 may be put into approximation with locking tang 8434, as illustrated in FIG. 58. When force transfer bar 8410 is fully inserted into receptacle 8433 of sled base 8431, release pin 8406 is inserted from beneath the sled base 8431. Release pin 8406 is sized to eliminate the clearance available to the force transfer bar within the receptacle of the sled base, holding force transfer bar 8410 in place against locking tang 8434 of sled base 8431.

If there is a failure of the device during use, release pin 8406 may be removed. Upon removal of the release pin 8406, receptacle 8433 will again provide sufficient clearance for the release of force transfer bar 8410 from locking tang 8434, so that force transfer bar 8410 may be removed from receptacle 8433. By releasing the force transfer bar from the sled base, the compressing force acting against anvil 8205 (via down pins 8421) and housing 8105 (via sled base 8431) will be released, allowing the surgical device to be removed from its position in tissue.

Figure 39:
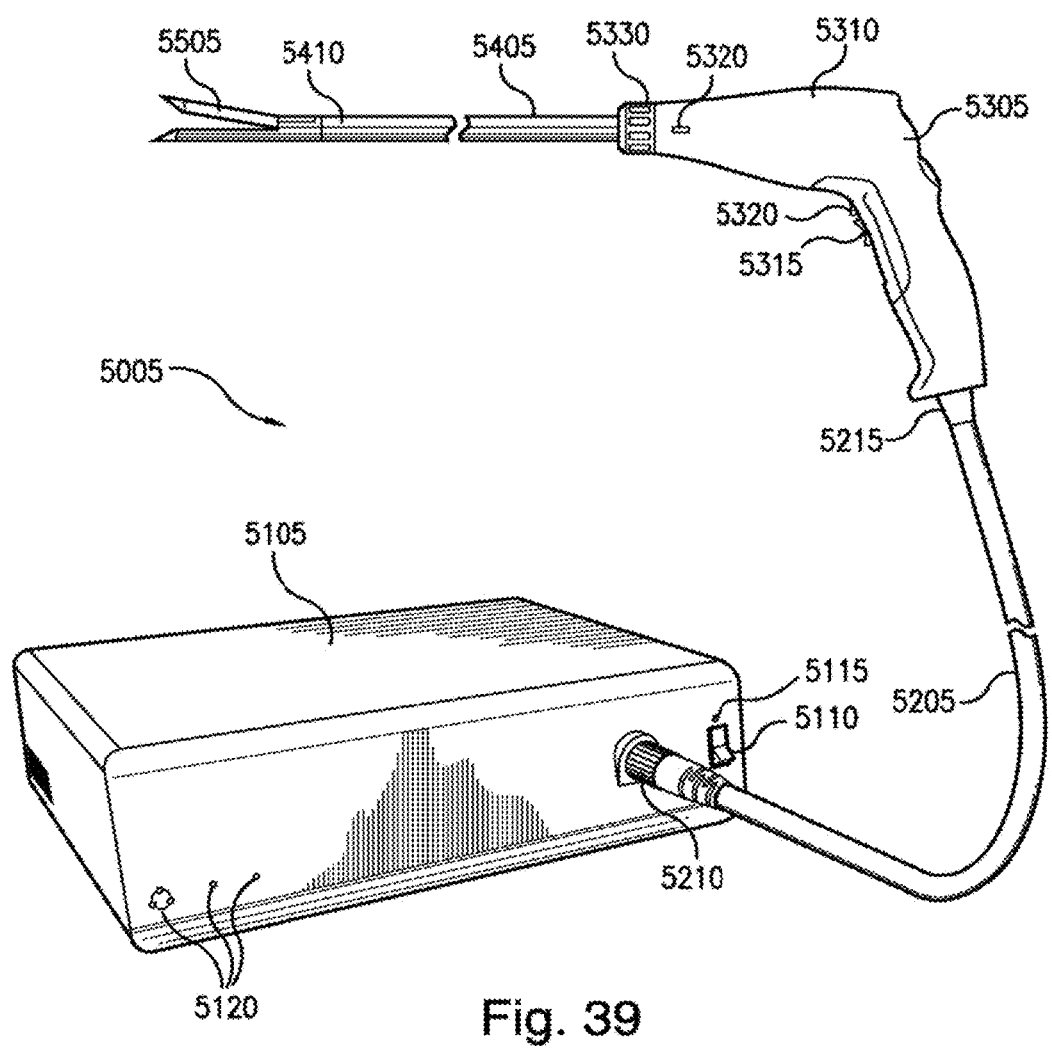
FIG. 39 shows a surgical system according to an example embodiment of the present invention.

FIG. 39 shows a surgical system 5005 that may be provided in connection with one or more of the devices 5, 1005, 3005, 8005 described above. The device includes a control module in the exemplary form of a base unit 5105 that houses one or more hydraulic controllers. The base unit 5105, which may be powered via an AC outlet and/or battery powered and has an external power switch 5110 and power-on indicator light 5110, may also include various electronics for performance of surgical procedure. Further, the base unit 5105 has a plurality of indicators 5115a that indicate the activity status and failure and ready states of the system 5005 to provide visual indicators to the operator. Extending from the base unit 5105 is a flexible shaft 5205 that connects to the base unit 5105 via an interchangeable plug connection 5210. The shaft 5205 extends from the base unit 5105 to a handle 5305 configured to be held by an operator, e.g., a surgeon, to perform a surgical procedure. The handle 5305 has a housing 5310 and a pair of electronic switches 5315 and 5320. The switch 5315 is a rocker switch configured to actuate closure and opening of opposed jaws of an end effector 5505, and the switch 5300 is configured as a trigger to control a cutting and stapling procedure of the end effector 5505. The end effector 5505 may be any of the devices 5, 1005, 3005, 8005 described above, such that the rocker switch controls the opening and closing of the anvil 205, 1205, 3205, 8205 with respect to the housing 105, 1105, 3105, 8205 and the trigger switch 5320 controls the axial movement of the carriage 405, 1405, 3405, 8405 with respect to the housing 105, 1105, 3105, 8105. In the alternative, as described herein with respect to device 8005, the opening and closing of the anvil 8205 may be controlled by the axial movement of the carriage 8205, and therefore a separate control for the opening and closing of the anvil 8205 may not be necessary.

Extending from a distal end of handle 5310 is a rod 5405, formed of polyoxymethylene (e.g., Delrin™) or any other suitable material such as, e.g., anodized aluminum. At the end of the rod 5405 is a flexible tube 5410 that extends from the rod 5405 to the end effector 5505. The interior of the tube 5410 is in communication with the interior of the rod 5405. In this regard, the plurality of hydraulic tubes associated with the end effector, e.g., device 5, 1005, 3005, 8005 (e.g., hydraulic tubes 705a, 705b, 705c, and 705d) extend from the interior of the base unit 5105 though the flexible shaft 5205, through the handle 5305, through the rod 5405, through the flexible tube 5410 and into the end effector 5505, e.g., the device 5, 1005, 3005, 8005 in the manner set forth herein. Thus, the device 5, 1005, 3005, 8005 may be operated as an end effector 5505 and hydraulically controlled by controllers in the control module 5105, e.g., in response to control signals from the switches 5320, 5315. Although the hydraulic controllers are disposed in a base unit 5105, it should be understood the controllers may be disposed at any suitable location, in accordance with additional example embodiments.

Although the switches 5315, 5320 are electronic switches, it should be understood that purely mechanical switches may be provided.

The shaft 5205 is provided with a strain relief 5215 formed of cast elastomer or any other suitable material at the connection to the handle 5305. Further, the housings 5310 of the handle 5305 may be formed by joining two cast halves (e.g., left and right halves).

At the distal end of the housing 5310 of each handle 5305 is a button 5325 and a knob 5330. The knob 5330 is rotatable about the longitudinal axis of the rod 5405 to actuate a movement of the end effector 5505 via bending of the flexible tube 5410, such as, e.g., the pivoting of the device 3005 as illustrated in FIG. 22B and/or a pivoting into the reverse direction. Any suitable motion or motions of the end effector 5505 may be configured to be actuated rotation of the knob 5330. The button 5325 has a default non-depressed position in which the knob 5330 is locked against rotation. When the knob is depressed by the operator, the operator is then able to rotate the knob 5330.

The flexible tube 5410 may include a stainless steel mesh inner tube which may be bonded on either end thereof. The tube 5410 may house one or more hinges for movement of the end effector 5505. Further, a portion of heat sink may be provided to cover and/or seal the edges of the flexible tube 5410, e.g., at the connection between the flexible tube 5410 and the rigid rod 5405.

Figure 40:
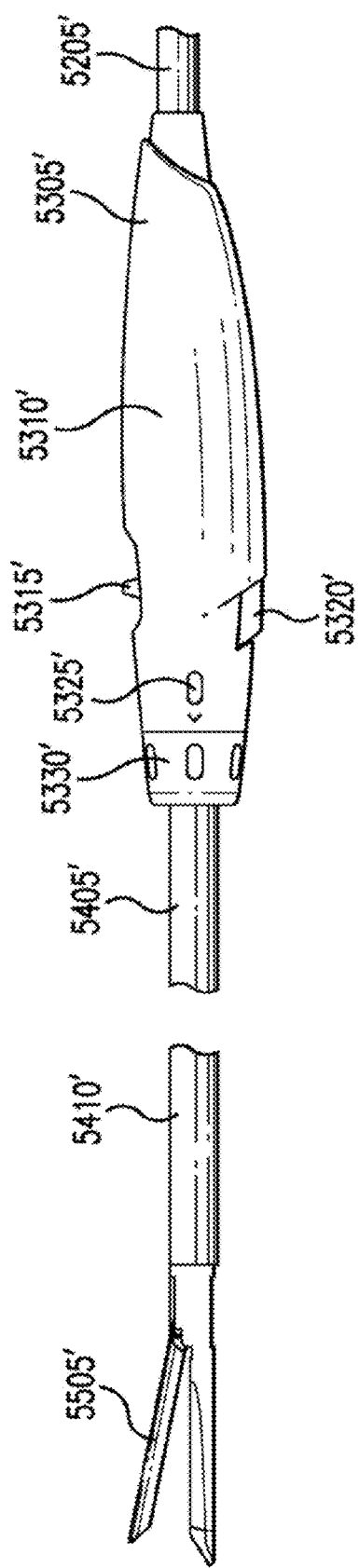
FIG. 40 shows a handle for use in connection with the surgical system of FIG. 39.

FIG. 40 shows another handle 5305' that may be provided in a system that is identical to the system 5305 described above except to the extent indicated otherwise. Further, like or analogous elements are provided with reference numbers that are the same as the reference numbers of FIG. 39, but followed with the character ' (prime). The system of FIG. 40 differs from the system of FIG. 39 in that the handle 5305' is provided in place of the handle 5305 in an additional example embodiment. The handle 5305' functions in the same manner as the handle 5305 and includes the same features as the handle 5305 unless indicated otherwise.

The handle 5305' differs from the handle 5305 it is has a straight handle, as opposed to the pistol-grip form of the handle 5305 in an additional example embodiment. The handle 5305' also differs in that it includes a slider switch 5305' in that it includes a slider switch 5315' instead of the rocker switch 5315 of the handle 5305 to open and close the jaws of the end effector 5505, e.g., the device 5, 1005, 3005, 8005. The shaft 5405' extending from the distal end of the handle 5305' is formed of black anodized machined aluminum or any other suitable material such as, e.g., polyoxymethylene (e.g., Delrin™).

Figure 41A:
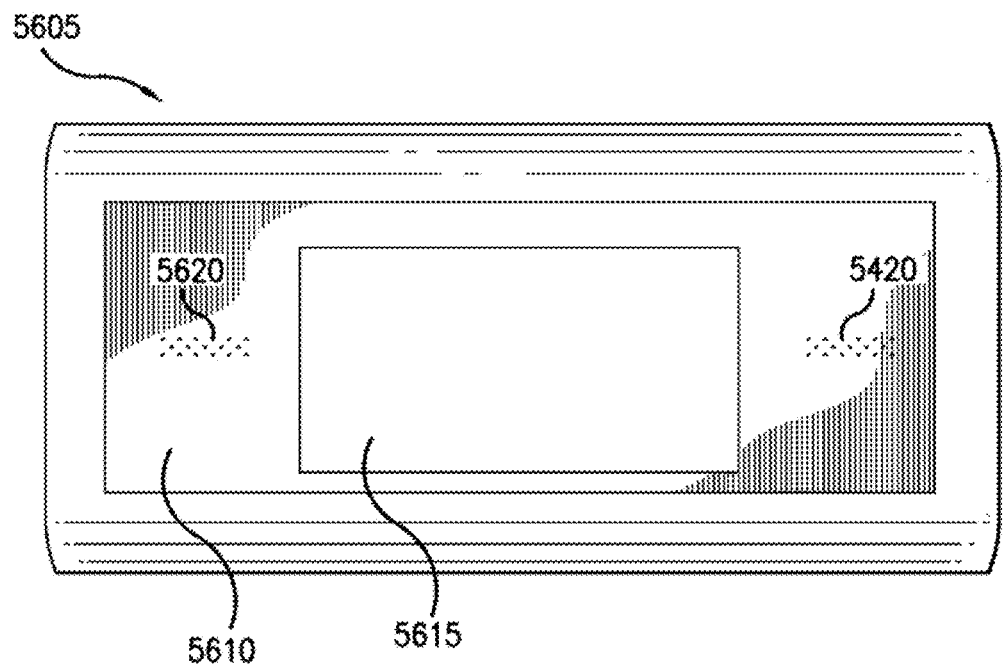
FIGS. 41A and 41B show a console for use in connection with the surgical system of FIG. 39.
Figure 41B:
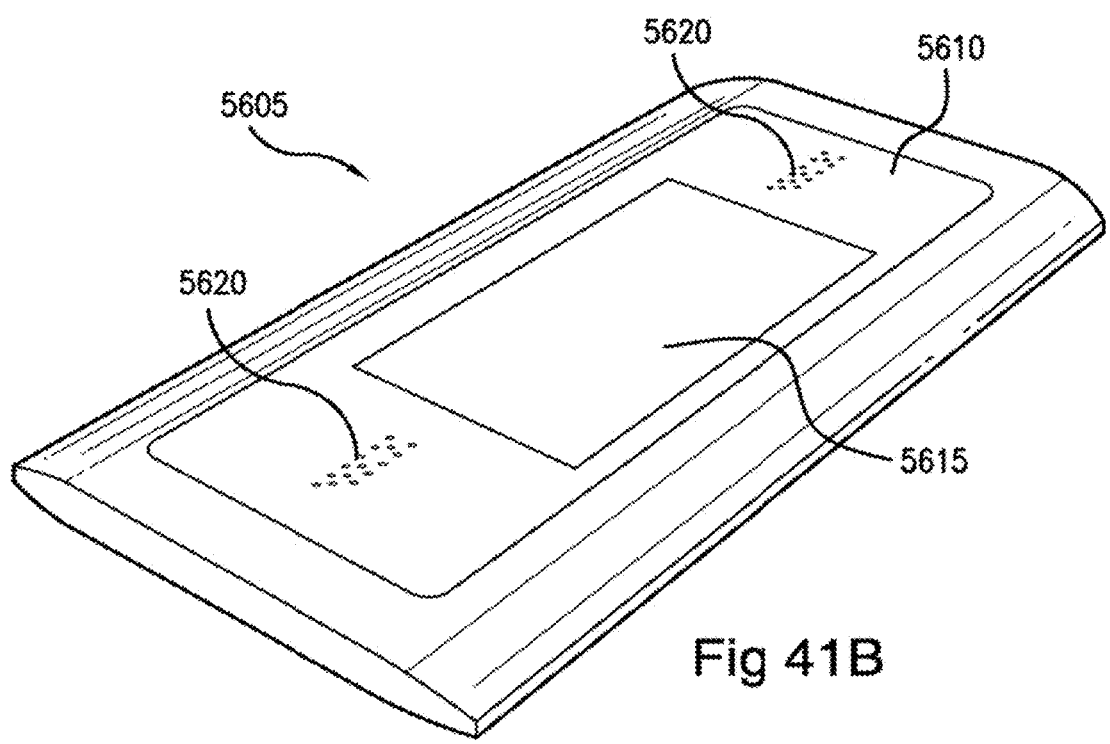

FIGS. 41A and 41B show a console 5605. The console 5605 may be used as part of or in connection with the system 5005. The console 5605 includes a top panel 5610 that includes a display 5615, e.g., an LCD screen or other suitable graphical display, as well as a pair of speakers 5620 configured to output monaural and/or stereo audio. The display 5615 and/or the speakers 5620 may be configured to display information and/or alerts to the operator in connection with the procedure being performed with the end effector 5505 (e.g., the device 5, 1005, 3005, 8005) of the system 5005. For example, the display 5615 may be configured to show status information, system health information, end effector parameters (e.g., the opened or closed state of the jaws of the end effector 5505 and and/or the state of a cutting and/or stapling such as described in connection with devices 5, 1005, 3005, 8005), feedback information (e.g., sensed pressure, temperature, or other parameters), and/or any other suitable information. Moreover, the display 5615 may be configured to show still and/or video images that may be obtained, e.g., from an endoscopic camera. In this regard, the console 5605 may be used in combination with an endoscope and/or a monitor to perform procedures under vision.

Further, the console 5605 may be used by the operator to input control signals such as operating parameters that may be used to control the other components of the system 5005, such as, e.g., the end effector 5505 and/or the base unit 5105.

The console 5605 may communicate with the base unit 5105 and/or any other component(s) of the system (e.g., the handle 5305 and/or the end effector 5505) via any suitable communication mechanism. For example, the communication mechanism may involve hard-wired and/or wireless transmissions.

Figure 42:
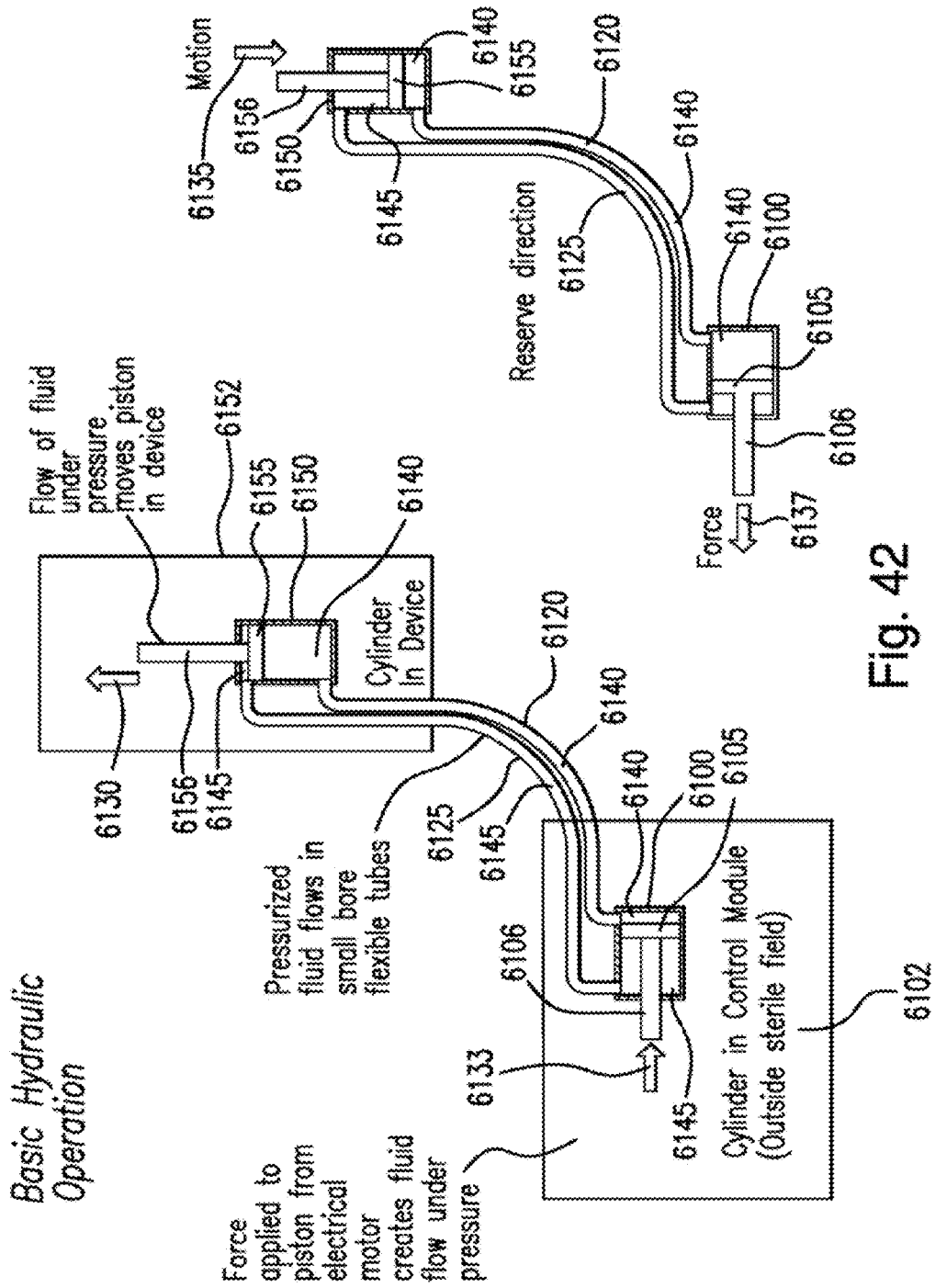
FIG. 42 schematically illustrates the hydraulic operation for exertion of force and motion in a first direction and in a second direction opposite the first direction.

FIG. 42 schematically illustrates hydraulic operation for exertion of force and motion in a first direction 6130 and in a second direction 6135 opposite the first direction 6130. In this regard, the actuation of a hydraulic control piston 6105 in a corresponding hydraulic control cylinder 6100 actuates a hydraulic actuation piston 6155 in a corresponding hydraulic actuation cylinder 6150.

The example arrangement of FIG. 42 provides two continuous sealed volumes of hydraulic fluid 6140, 6145 (e.g., saline or other suitable liquid). The first sealed volume 6140 is separated from the second sealed volume 6145 by the control piston 6105 and the actuation piston 6155.

Referring to the arrangement on the left side of FIG. 42, a force 6133 is applied to the control piston 6105, via control piston shaft 6106, thereby pressurizing the first fluid volume 6140. The force may be applied by any appropriate mechanism, e.g., an electric motor, solenoid, and/or any other suitable device. Since the components of the system, including the small bore flexible tubes 6120, 6125, are relatively non-expandable, the force is substantially transferred to the portion of the first volume of hydraulic fluid 6140 in the actuation cylinder 6150. The pressure increase in the first volume 6140 acts on the face of the actuation cylinder 6150 contacting the first volume 6140. In this regard, the force exerted on the actuation piston 6145 by the first volume 6140 is generally equal to the pressure of the fluid 6140 multiplied by the area of the piston 6140 exposed to the pressurized fluid 6140 when viewed along the axis of the actuation chamber 6150. The application of the force 6133 causes the pressure in the first fluid to be sufficiently greater than the pressure of the fluid of the volume 6145 that the actuation piston 6155 moves in the direction 6130 due to a net force exerted on the piston 6155 in the direction 6130. As the control piston 6106 and the actuation piston 6155 move within their respective cylinders 6100, 6150, the pressurized fluid of the first volume 6140 flows in the tube 6120 in a direction from the control cylinder 6100 toward the actuation cylinder 6150, and the fluid of the second volume 6145 flows in the tube 6125 in a direction from the actuation cylinder 6155 toward the control cylinder 6100.

As shown on the right-side portion of FIG. 42, the piston 6155 is actuated in the reverse direction 6135 in an analogous manner by a force 6137 in the direction opposite the force 6133 to pressurized the second volume 6145 and cause the fluids of the first and second volumes 6140, 6145 to flow in the tubes 6120, 6125 in directions opposite the directions described above with regard to the forward actuation.

In the schematic illustration of FIG. 42, the hydraulic control cylinder 6100 and the hydraulic control piston 6105 are disposed in a control module 6102, which may be outside the sterile field of a surgical procedure, while the hydraulic actuation cylinder 6150 and the hydraulic actuation piston 6155 are disposed in a device 6152, with the tubes 6120, 6125 interconnecting the control module 6102 and the device 6152. For example, referring to system 5005 described above, the hydraulic control cylinder 6100 and the hydraulic control piston 6105 may be housed in the base unit 5105 while the hydraulic actuation cylinder 6150 and the hydraulic actuation piston 6155 are disposed in the end effector 5505 (e.g., the device 5, 1005, 3005, 8005). For example, where the end effector 5055 is one of the devices 5, 1005, 3005, 8005, the actuation mechanism of FIG. 42 may be provided to actuation the anvil pistons 305, 1305, 3305 and the ratchet pistons 605, 1605, 3605, 8605. Thus, the control module 5105 may operate two control piston arrangements, one to control the anvil piston 305, 1305, 3305 and one to independently control the ratchet piston 605, 1605, 3605, 8605.

Although the pistons 6105 and 6145 are show as being substantially the same diameter, it should be understood that the relative diameters may be selected to provide any desired hydraulic leverage. Pistons 6105 and 6145 having the same diameter will match the input force and displacement on piston 6145 with the same corresponding output force and displacement on piston 6105. If desired, the force and displacement of the output piston 6105 may be leveraged against the force and displacement applied to the input piston 6145, according to the ratio of the area of the pistons. That is, if input piston 6145 has an area five times greater than output piston 6105, than any force applied to input piston 6145 would result in a corresponding force five times greater in the output piston 6105, and any displacement applied to input piston 6145 would result in a corresponding displacement five times smaller in the output piston 6105. As system may therefore be designed to apply a particular force or a particular displacement, according to the user's particular surgical needs. In other words, mechanical advantage may be attained, based on Pascal's law.

Although the example arrangement of FIG. 42 provides two continuous sealed volumes of hydraulic fluid 6140, 6145, the other example arrangements may provide one continuous sealed volume of hydraulic fluid, either 6140 or 6145. In this example arrangement, application of the force 6133 on the control piston 6105 may increase the pressure on the fluid volume 6140, or decrease the pressure on the fluid volume 6145, of the sealed volume of hydraulic fluid, depending on which fluid volume is provided. If the fluid volume 6140 is provided, application of the force 6133 pressurizes the fluid volume 6145, which translates this pressure to fluid 6140, which applies a force on actuation piston 6155. If the fluid volume 6145 is provided, application of the force 6133 draws fluid from fluid volume 6145, decreasing the pressure of the fluid volume 6145, which translates this decrease in pressure to fluid 6140, which applies a drawing force on actuation piston 6155. The force 6133 is therefore translated through the hydraulic volume, to the actuation piston 6155.

Figure 43A:
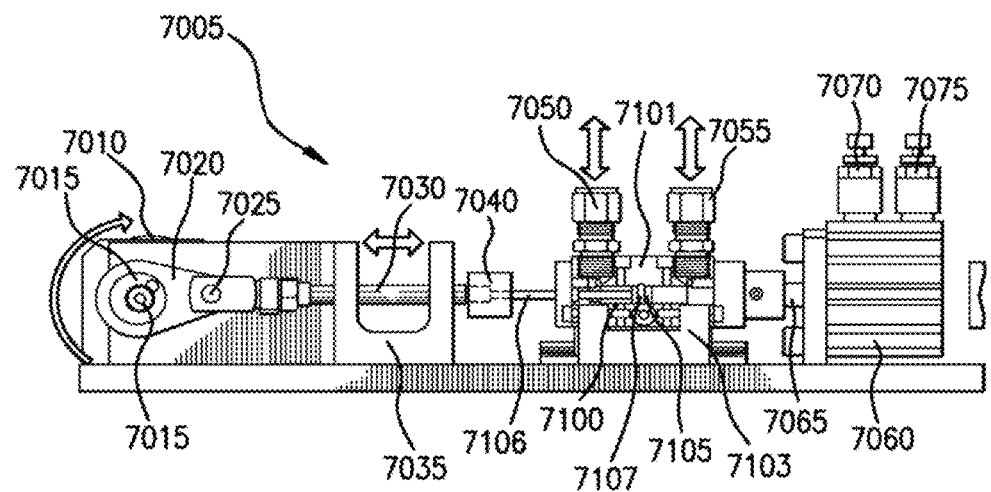

FIG. 43A shows control mechanism 7005 utilizes the same general design and actuation principle as schematically illustrated and described with regard to FIG. 42. The actuation of the forces 6133 and 6137 of FIG. 42 are provided in the mechanism 7005 of FIG. 43A by an electric motor 7010, which may be controlled by any suitable controller. The output shaft of the electric motor is coupled to a crankshaft mechanism 7015, which includes an eccentric pin 7016 that is offset from the rotational axis of the output shaft of the motor and is rotatably coupled to a link 7020, which is also rotatably coupled, via joint 7025, to an intermediate output shaft 7030. The shaft 7030 is slidably supported at two spaced axial locations by a bearing block 7035, which permits translation of the intermediate shaft 7030 along its longitudinal axis but restrains the intermediate shaft 7030 from lateral movement or rotation. Thus, when the motor 7010 rotates, the corresponding rotation of the eccentric pin 7016 causes a reciprocating axial movement of the intermediate shaft 7030. The intermediate shaft 7030 is coupled, via coupling 7040, to a control piston shaft 7106 of a hydraulic control piston 7105, which slides within a hydraulic control cylinder 7100. Thus, the reciprocation of the intermediate shaft 7030 causes the piston 7105 to axially reciprocate within the cylinder 7100.

The control piston shaft 7106, hydraulic control piston 7105, and hydraulic control cylinder 7100 are analogous to the control piston shaft 6106, hydraulic control piston 6105, and hydraulic control cylinder 6100 of the system of FIG. 22 described above and therefore function in the same manner. In this regard, tubes corresponding to the tubes 6120 and 6125 of FIG. 42 are connected to the respective sides of the cylinder 7100 via respective fluid connectors 7050 and 7055. For example, the tube 705c, 1705c, 3705c may be coupled to connector 7050 and the complementary tube 705d, 1705d, 3705d coupled to the connector 7055, or vice-versa, in order to actuate the ratchet piston 605, 1605, 3605, 8605 in the first hydraulic chamber 110, 1110, 3110, 8110. Thus, as the piston 7105 is reciprocated in the cylinder 7100 by the electric motor 7010, a corresponding reciprocating motion is actuated in the piston corresponding to the piston 6155 of FIG. 22.

Further, in order to control the range in which the piston (e.g., ratchet piston 605) is actuated (e.g., reciprocated), the range of motion (e.g., reciprocation) of the control piston is controllable via a linear actuator 7060, which is provided in the example as an air cylinder, but may be any appropriate actuator. The linear actuator 7060 moves the drive cylinder 7100 with respect to piston 7105 by moving the drive cylinder 7100 axially with respect to the motor and other fixed drive components of the system 7005. This is accomplished by pushing a cylinder block 7101, in which the cylinder 7100 is formed, along the axis of the cylinder 7100 via the axial extension or retraction of an output shaft 7065 of the linear actuator 7060. The linear actuator 7060 is driven by air input/output valves 7070 and 7075.

The cylinder block 7101 is slidably supported in a block support 7103, which limits the axial position of the block support 7101, and therefore the cylinder 7105, in both axial directions by providing positive stops corresponding to two predetermined axial positions of the cylinder 7100 with respect to the available stroke range of the piston 7105. In this regard, the movement of the cylinder between these positions effects an analogous shift in the piston being actuated. For example, the first predetermined position of the cylinder 7100 may cause the ratchet piston 605 to reciprocate in the first axial region 660, while the movement of the cylinder 7100 to the second predetermined position may cause the ratchet piston 605 reciprocate in the second axial region 670 as described in greater detail above with respect to FIGS. 10C to 10E. Thus, the actuator 7060 is configured to move the drive cylinder 7100 to two fixed positions to create two selectable zones 660, 670 of piston actuation.

Further, the hydraulic tube 705a, 1705a, 3705a, 8705a of the device 5, 1005, 3005 may be coupled to connector 7050 and the complementary tube 705b, 1705b, 3705b coupled to the connector 7055, or vice-versa, in order to actuate the anvil piston 305, 1305, 3305 in the first hydraulic chamber 110, 1110, 3110. In this regard, the motor 7010 may be controlled such that the piston is moved in a non-reciprocating manner in order to actuate the anvil piston 305, 1305, 3305.

An o-ring 7107 maintains a seal at the interface between the piston 7105 and the cylinder 7100 that separates the first and second sealed fluid volumes disposed on opposed sides of the piston 7105.

FIGS. 43B to 43E, an alternative embodiment of the base unit is illustrated. Base unit 9105 includes a bezel 9011 in which plug receptor 9008 connects the interior of base unit 9105 to the pluggable surgical device. Interchangeable plug connection 9210 includes shaft 9205 and plug body 9003.

Plug body 9003, having four single-action pistons 9016, 9026, 9036 (background, not pictured), 9046 (foreground, not pictured), may be attached to plug receptor 9008, for example, via wing nut 9007. Each of pistons 9016, 9026, 9036, and 9046 are situated in hydraulic chambers 9116, 9126, 9136 (background, not pictured), 9146 (foreground, not pictured), respectively. Push rods 9019, 9029, 9039, and 9049 (foreground, not pictured), actuated by a motor of base unit 9105, engage with pistons 9016, 9026, 9036, and 9046, respectively, to provide positive or negative force on each hydraulic chamber. Opposite the piston, each hydraulic chamber faces tubes 9216, 9226, 9236, and 9246, to translate the positive or negative hydraulic force experienced in each hydraulic chamber to the piston or pistons of the surgical device.

Pistons 9016 and 9026 form a pair of single-action pistons that provide positive and negative hydraulic forces to the ratchet pistons of the present invention. Hydraulic chambers 9116 and 9126 are in fluid connection with the complementary hydraulic chambers located distally and proximally to the double-action ratchet pistons of the surgical device. Piston pair 9016 and 9026, therefore, each complement the hydraulic forces provided by the other, to oscillate the double-action ratchet piston as needed. Pistons 9036 and 9046 may form an additional pair of single-action pistons to provide positive and negative hydraulic forces to an additional double-action piston, e.g., a steering piston or an anvil piston.

Figure 44:
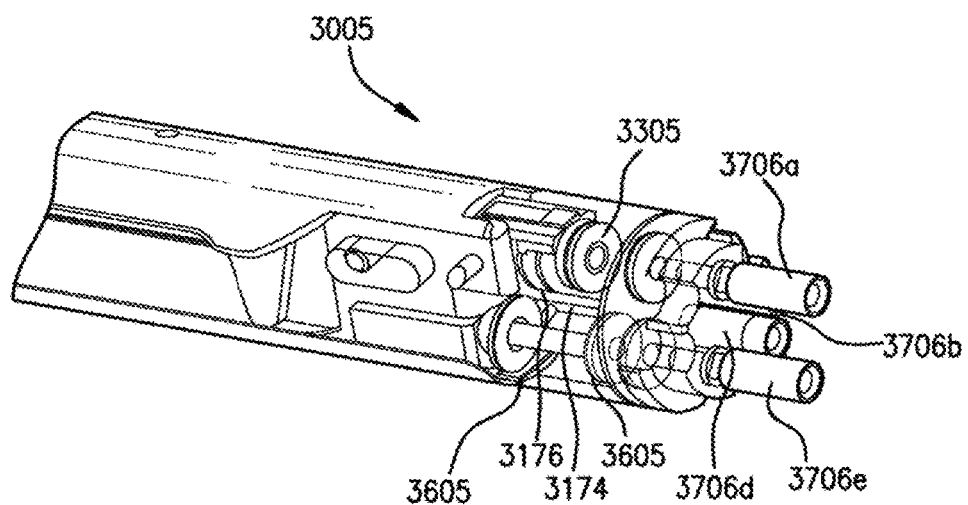
FIG. 44 is a partial internal perspective view of the device of FIG. 32A in connection with the hydraulic control hardware of FIG. 43.

FIG. 44 is a partial internal perspective view of the device 3005 of FIG. 22A in connection with the hydraulic control hardware 7005 of FIG. 43. To reciprocate the ratchet piston 7605 as indicated above, the hydraulic tube 3705c would be connected, via connector 3706c, in order transfer hydraulic fluid between the connector 7050 of the mechanism 7005 and the portion of the cylinder 3150 that is proximal to the seal formed between the piston 3605 and the cylinder 3150, and the hydraulic tube 3705d would be connected, via connector 3706d, in order transfer hydraulic fluid between the connector 7055 of the mechanism 7005 and the portion of the cylinder 3150 that is distal to the seal formed between the piston 3605 and the cylinder 3150. In this manner, the reciprocating piston 7105 in the drive cylinder 7100, which alternates in different directions to cyclically move fluid in and out of the tube connection 7050 and 7055 and tubes 3705a and 3705b. The tubes 3705a and 3705b transfer reciprocating fluid to create oscillating motion in the end effector cylinder 150. This is achieved by the fluid moving in and out of the cylinder 3150 on either side of the piston seal (formed by between the piston 3605 and the cylinder 3150 with o-ring 3620) causes the piston 3605 in the end effector 3005 to reciprocate.

The anvil piston 3305 may be driven by a respective mechanism 7005 via an analogous connection, whereby tubes 3705a, 3705b are connected to respective connectors 3706a, 3706b and 7050, 7055 to convey hydraulic fluid.

Although the reciprocating surgical devices 5, 1005, 3005, 8005 described above utilize a hydraulic actuation system to transfer force from a control module to the , it should be understood that other actuation systems may be provided, e.g., electromechanical drivers. For example, one or more solenoids (e.g., in the end effector 5, 1005, 3005, 8005 and/or any other location of the system) may be provided to reciprocate the actuating bar and/or actuate the anvil between the opened and closed positions.

Further, although reciprocating actuation mechanisms are described in the examples as having one or more teeth, it should be understood that engaging teeth may be dispensed with, and/or any other engagement mechanism, e.g., a directional friction, may be provided in addition to or as an alternative to the teeth described herein.

The arrangement of the surgical devices described herein includes a ratcheting element that is located in the housing, and not in the handle. This arrangement allows for the use of a flexible shaft, which supports remote operation of the surgical device.

Although the present invention has been described with reference to particular examples and exemplary embodiments, it should be understood that the foregoing description is in no manner limiting. Moreover, the features described herein may be used in any combination.

What is claimed is:

1. A surgical device, comprising;
a base unit having a hydraulic controller and at least one control piston;
a surgical end effector including at least one actuator piston; and
a flexible shaft having at least one tube containing hydraulic fluid in hydraulic communication with the base unit and the surgical end effector;
wherein the hydraulic controller includes an electric motor configured to drive the control piston to generate a hydraulic force;
wherein the hydraulic force is transferable from the base unit to the actuator piston of the surgical end effector through the hydraulic fluid in the at least one tube in the flexible shaft, such that the driving of the control piston by the electric motor under the control of the hydraulic controller transfers the hydraulic force from the control piston of the base unit to the actuator piston of the end effector in proportion to the ratio of the area of the control piston and the area of the actuator piston by metering the hydraulic fluid transferred by the control piston.

2. The surgical stapling device of claim 1,
wherein a first side of the control piston is in fluid communication with a distal side of the actuator piston, and a second side of the control piston is in fluid communication with a proximal side of the actuator piston; and
wherein the control piston exacts positive or negative hydraulic pressure on the distal or the proximal side of the actuator piston.

3. The surgical device of claim 2,
wherein the hydraulic controller further includes a shaft coupled to the electric motor and the control piston, the shaft configured to be linearly moved by electric motor, and to translate the motion to the control piston.

4. The surgical device of claim 1, further comprising:
a control device, including a switch, situated between the base unit and the surgical end effector;
wherein the switch is operable to selectively initiate transfer of the hydraulic force from the base unit to the actuator piston, and to selectively terminate transfer of the hydraulic force from the base unit to the actuator piston.

5. The surgical stapling device of claim 1,
wherein the hydraulic controller includes at least two control pistons, one of the at least two control pistons being in fluid communication with a distal side of the actuator piston, and one of the at least two control pistons being in fluid communication with a proximal side of the actuator piston; and
wherein each of the at least two control pistons exacts positive or negative hydraulic pressure on the distal or the proximal side of the actuator piston.

6. The surgical device of claim 5,
wherein the hydraulic controller further includes a shaft coupled to the electric motor and one of the at least two control pistons, the shaft configured to be linearly moved by electric motor, and to translate the motion to move the control piston.

7. The surgical device of claim 1, the surgical end effector comprising;
a first jaw;
a second jaw having an open position and a closed position with respect to the first jaw;
an actuating bar arranged in the first jaw and including a first set of ratchet teeth;
a housing; having at least one staple and at least one staple driving slot, situated in the first jaw; and
a carriage including a force transfer bar, a sled base, and a release pin, the force transfer bar having a protrusion for engagement with a locking tang of the sled base, the release pin configured to hold the protrusion of the force transfer bar in approximation with the locking tang of the sled base;
wherein one of the at least one actuating piston is configured to oscillatingly displace the actuating bar along a longitudinal direction of the first jaw;
wherein the carriage is selectively engageable with the first set of ratchet teeth of the actuating bar to translate the carriage in a distal direction through the housing from a proximal terminal position to a distal terminal position, and is engageable with the first and second jaw to exert a clamping force to move the second jaw from the open position to the closed position;
wherein the release pin is configured, upon removal, to permit the force transfer bar to release from the locking tang of the sled base.

8. A surgical stapling device, comprising;
a first jaw;
a second jaw having an open position and a closed position with respect to the first jaw;
an actuating bar arranged in the first jaw and including a first set of ratchet teeth;
a ratchet piston configured to oscillatingly displace the actuating bar along a longitudinal direction of the first jaw;
a housing; having at least one staple and at least one staple driving slot, situated in the first jaw; and
a carriage including a force transfer bar, a sled base, and a release pin, the force transfer bar having a protrusion for engagement with a locking tang of the sled base, the release pin configured to hold the protrusion of the force transfer bar in approximation with the locking tang of the sled base;
wherein the carriage is selectively engageable with the first set of ratchet teeth of the actuating bar to translate the carriage in a distal direction through the housing from a proximal terminal position to a distal terminal position, and is engageable with the first and second jaw to exert a clamping force to move the second jaw from the open position to the closed position;
wherein the release pin is configured, upon removal, to permit the force transfer bar to release from the locking tang of the sled base.

9. The surgical stapling device of claim 8, further comprising;

a base unit having a hydraulic controller and at least one control piston; and a flexible shaft having at least one tube containing hydraulic fluid in hydraulic communication with the base unit and the ratchet piston;

wherein the hydraulic controller includes an electric motor configured drive the control piston to generate a hydraulic force;

wherein the hydraulic force is transferable from the base unit to the ratchet piston through the hydraulic fluid in the at least one tube in the flexible shaft, such that the driving of the control piston by the electric motor under the control of the hydraulic controller transfers the hydraulic force from the control piston of the base unit to the ratchet piston of the end effector in proportion to the ratio of the area of the control piston and the area of the ratchet piston by metering the hydraulic fluid transferred by the control piston.

10. The surgical stapling device of claim 8, the carriage including at least one staple-driving wedge adapted to drive the staple through the staple driving slot against the second jaw during distal movement of the carriage through the housing.

\* \* \* \* \*